US010213645B1

(12) United States Patent
Wu et al.

(10) Patent No.: US 10,213,645 B1
(45) Date of Patent: Feb. 26, 2019

(54) MOTION ATTRIBUTES RECOGNITION SYSTEM AND METHODS

(71) Applicant: Swingbyte, Inc., Chicago, IL (US)

(72) Inventors: Ying Wu, Lincolnshire, IL (US); Nan Jiang, Lincolnshire, IL (US); Alex Pedenko, Chicago, IL (US)

(73) Assignee: SWINGBYTE, INC., Chicago, IL (US)

( * ) Notice: Subject to any disclaimer, the term of this patent is extended or adjusted under 35 U.S.C. 154(b) by 847 days.

(21) Appl. No.: 14/843,526

(22) Filed: Sep. 2, 2015

Related U.S. Application Data

(63) Continuation-in-part of application No. 14/158,005, filed on Jan. 17, 2014, now Pat. No. 9,211,439, and a
(Continued)

(51) Int. Cl.
*A63F 9/24* (2006.01)
*A63B 24/00* (2006.01)
(Continued)

(52) U.S. Cl.
CPC .......... *A63B 24/0006* (2013.01); *A63B 69/36* (2013.01); *A63B 71/0619* (2013.01);
(Continued)

(58) Field of Classification Search
CPC .. G06K 9/6262; A63B 24/00; A63B 24/0003; A63B 24/0006; A63B 2024/0009; A63B 2024/0012; A63B 2024/0015; A63B 69/36; A63B 69/3632; A63B 71/0622; A63B 2220/34; A63B 2220/40; A63B 2220/62;
(Continued)

(56) References Cited

U.S. PATENT DOCUMENTS

| 3,945,646 A | 3/1976 | Hammond |
| 5,108,105 A | 4/1992 | Shimizu |

(Continued)

FOREIGN PATENT DOCUMENTS

| EP | 0494749 A1 | 7/1992 |
| GB | 2318982 A | 5/1998 |

(Continued)

OTHER PUBLICATIONS

"Low Cost Inertial Navigation: Learning to Integrate Noise and Find Your Way" by Kevin J. Walchko, Thesis Presented to the Graduate School of the University of Florida in Partial Fulfillment of the Requirements for the Degree of Master of Science, University of Florida, 2002.

*Primary Examiner* — Michael Cuff
(74) *Attorney, Agent, or Firm* — Perry Hoffman

(57) ABSTRACT

Systems and methods for motion attribute recognition are defined using data stream pre-processing to orient, align and segment motion data before using non-parametric classification recognition to search a motion data exemplar database or using parametric classification recognition to find attributes by comparing pre-processed motion data with support vector machines. Results from the non-parametric classification recognition and the parametric classification recognition may be fused to produce a single result. Active learning and metric learning are used to improve searches of the database and comparisons to the support vector machines.

19 Claims, 43 Drawing Sheets

Related U.S. Application Data continuation-in-part of application No. 13/251,489, filed on Oct. 3, 2011, now Pat. No. 8,696,482.

(60) Provisional application No. 62/045,148, filed on Sep. 3, 2014.

(51) Int. Cl.
*A63B 71/06* (2006.01)
*A63B 69/36* (2006.01)
*G06K 9/62* (2006.01)
*G06T 7/20* (2017.01)

(52) U.S. Cl.
CPC ......... *G06K 9/6203* (2013.01); *G06K 9/6262* (2013.01); *G06K 9/6277* (2013.01); *G06T 7/2006* (2013.01); *A63B 2024/0012* (2013.01); *A63B 2220/13* (2013.01); *A63B 2220/16* (2013.01); *G06T 2207/10016* (2013.01); *G06T 2207/30221* (2013.01)

(58) Field of Classification Search
CPC .......... A63B 2220/833; A63B 2225/20; A63B 2225/50
USPC .................................... 700/91; 473/131, 223
See application file for complete search history.

(56) References Cited

U.S. PATENT DOCUMENTS

| | | |
|---|---|---|
| 5,257,084 A | 10/1993 | Marsh |
| 5,332,225 A | 7/1994 | Ura |
| 5,447,305 A | 9/1995 | Socci et al. |
| 5,453,758 A | 9/1995 | Sato |
| 5,516,105 A | 5/1996 | Eisenbrey et al. |
| 5,575,719 A | 11/1996 | Gobush et al. |
| 5,692,965 A | 12/1997 | Nighan et al. |
| 5,694,340 A | 12/1997 | Kim |
| 5,704,836 A | 1/1998 | Norton et al. |
| 5,718,639 A | 2/1998 | Bouton |
| 5,873,789 A | 2/1999 | Torriano |
| 5,941,779 A | 8/1999 | Zeiner-Gundersen |
| 6,073,086 A | 6/2000 | Marinelli |
| 6,162,123 A | 12/2000 | Woolston |
| 6,375,579 B1 | 4/2002 | Hart |
| 6,441,745 B1 | 8/2002 | Gates |
| 7,021,140 B2 | 4/2006 | Perkins |
| 7,219,033 B2 | 5/2007 | Kolen |
| 7,234,351 B2 | 6/2007 | Perkins |
| 7,329,193 B2 | 2/2008 | Plank, Jr. |
| 7,384,343 B2 | 6/2008 | Zancucchi |
| 7,536,033 B2 * | 5/2009 | Kirby .................. A63B 24/0003 382/107 |
| 7,691,004 B1 | 4/2010 | Lueders |
| 7,785,211 B2 | 8/2010 | Hackenberg |
| 7,837,572 B2 | 11/2010 | Bissonnette et al. |
| 7,959,517 B2 | 6/2011 | Lastowka |
| 8,257,191 B2 | 9/2012 | Stites et al. |
| 8,409,024 B2 | 4/2013 | Marty et al. |
| 8,608,595 B2 | 12/2013 | Ikka et al. |
| 8,821,306 B2 * | 9/2014 | Margoles ........... A63B 69/3623 473/223 |
| 8,956,238 B2 * | 2/2015 | Boyd .................. A63B 24/0003 473/223 |
| 2002/0077189 A1 | 6/2002 | Tuer et al. |
| 2002/0123386 A1 | 9/2002 | Perlmutter |
| 2003/0207718 A1 | 11/2003 | Perlmutter |
| 2005/0085309 A1 | 4/2005 | McGann et al. |
| 2005/0085311 A1 | 4/2005 | Voges et al. |
| 2005/0272513 A1 | 12/2005 | Bissonnette et al. |
| 2005/0272514 A1 | 12/2005 | Bissonnette et al. |
| 2005/0272516 A1 | 12/2005 | Gobush |
| 2006/0068927 A1 | 3/2006 | Rankin et al. |
| 2007/0135223 A1 | 6/2007 | Bissonnette |
| 2008/0020867 A1 | 1/2008 | Manwaring |
| 2009/0221379 A1 | 9/2009 | Cameron |
| 2010/0049468 A1 | 2/2010 | Papadourakis |
| 2010/0255922 A1 | 10/2010 | Lueders |
| 2011/0124429 A1 | 5/2011 | Bissonnette |
| 2011/0212791 A1 | 9/2011 | Ueda et al. |
| 2011/0300959 A1 | 12/2011 | Hasegawa et al. |
| 2011/0306435 A1 | 12/2011 | Seo |
| 2012/0088544 A1 * | 4/2012 | Bentley ................... A63F 13/06 455/556.1 |
| 2012/0108354 A1 | 5/2012 | Kamino et al. |
| 2012/0136464 A1 * | 5/2012 | Saito .................. A63B 69/3614 700/91 |
| 2013/0029791 A1 * | 1/2013 | Rose .................. G09B 19/0038 473/409 |
| 2014/0274022 A1 * | 9/2014 | Bell .................... G06Q 30/0282 455/418 |
| 2015/0018111 A1 * | 1/2015 | Nadkarni ........... A63B 69/3632 473/223 |
| 2016/0354671 A1 * | 12/2016 | Nuesmeyer ........... H04B 1/385 |
| 2017/0061817 A1 * | 3/2017 | Mettler May ........ G09B 19/003 |
| 2017/0076619 A1 * | 3/2017 | Wallach ............ G09B 19/0038 |

FOREIGN PATENT DOCUMENTS

| | | |
|---|---|---|
| JP | 2010274089 A | 12/2010 |
| SU | 814373 | 3/1981 |
| WO | WO9745176 A1 | 12/1997 |
| WO | WO0069528 A1 | 11/2000 |
| WO | WO02035184 A3 | 5/2002 |

* cited by examiner

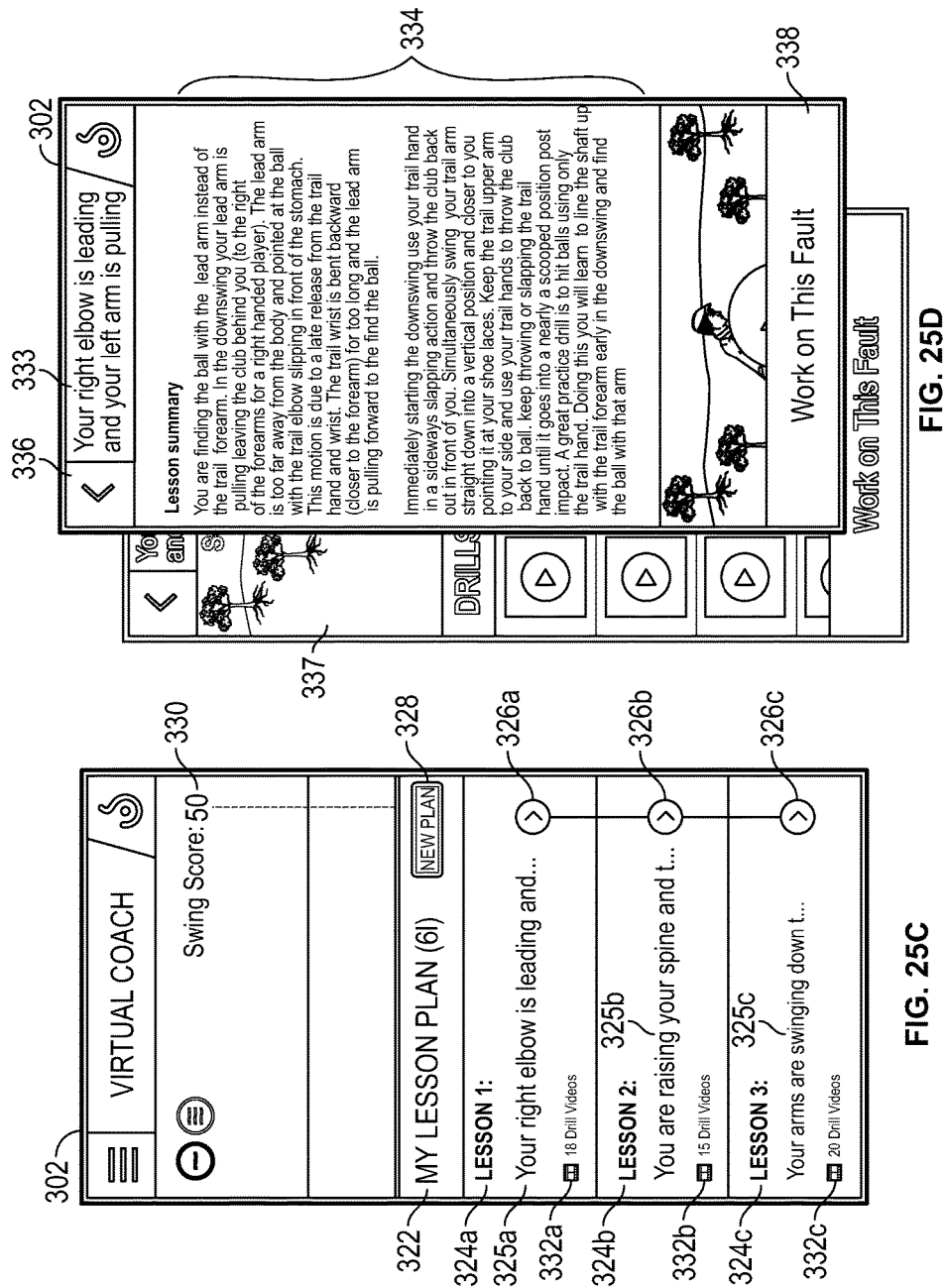

FIG. 28F

MOTION ATTRIBUTES RECOGNITION SYSTEM AND METHODS

CROSS-REFERENCE TO RELATED APPLICATIONS

This application claims priority benefit pursuant to 35 U.S.C. §§ 119 and/or 120 from U.S. Patent Application No. 62/045,148 filed Sep. 3, 2014, Ser. No. 14/158,005 filed Jan. 17, 2014, and Ser. No. 13/251,489 filed Oct. 3, 2011, now U.S. Pat. No. 8,696,482, hereby expressly incorporated herein by reference.

FIELD OF THE INVENTION

The present invention relates generally to analyzing linear and angular movement using a graphical animation of such movement and statistics related to such movement, and more particularly to analyzing a golf swing, for example, by attaching an apparatus to a golf club wherein the apparatus communicates with a mobile device, such as a smart phone or a tablet computer, and graphically shows the golf swing along with relevant statistics to help a golfer analyze and improve his or her golf swing. Laser lines may also be shown graphically for swing plane analysis.

The present invention further relates to error correction in the measurements taken. Specifically, a camera and image recognition software are used to measure the distance between a golf ball and club head at address, the orientation of the apparatus relative to the club head face, and the club head deflection throughout the swing, and these measurements are combined with data from an accelerometer and a gyroscope to create data that more accurately reflects a golf swing and corresponding laser lines. Accelerometer and gyroscope errors are also corrected using correlated optical image sensor data to produce object speed and coordinate data that is combined with the accelerometer and gyroscope data. Error correction is further accomplished by analyzing position data throughout the swing using ultrasonic and radio frequency pulses to correct errors caused by drift in gyroscope measurements and signal noise from both accelerometer and gyroscope sensors.

The present invention additionally relates to comparing real-time video of a player's shot side by side with the animation. Specifically, a camera on the tablet computer or other mobile device is aligned and used to capture and to automatically trim real-time video of the player's shot to create a video duplication of the animated view of the shot for side-by-side comparison.

The present invention also relates to recognizing motion attributes in golfers' swings, to finding faults in those swings by comparing those attributes to baseline attributes, and to coaching to improve a golfer's swing using a virtual coach.

BACKGROUND OF THE INVENTION

Over the past several years, the popularity of golf has soared, leading to a great number of inventions that allow a player to get enjoyment by playing a simulated game or to practice by using a machine to analyze a player's golf swing.

Particularly relevant to game simulation are inventions in the prior art using gesture recognition to allow a player to make realistic movements that are mimicked on a video display. For example, a player playing a simulated golf game can use a real or mock golf club to make the movements of an actual golf swing and see the mimicked swing on a video display followed by the graphical representation of a golf ball flying off a graphical tee, hopefully towards a graphical hole. U.S. Pat. No. 5,453,758, issued to Sato, for "Input Apparatus" "outputs as operator information the position specifying information obtained by detecting input apparatus's physical displacement, movement velocity, or acceleration to generate a predetermined command signal corresponding to movements of a human being for example". Sato further discloses using an oscillation gyroscope to sense angular velocity and a temperature sensor to correct errors in movement related data caused by changing temperature conditions. U.S. Pat. No. 5,516,105, issued to Eisenbrey, et al., for "Acceleration Activated Joystick" discloses a "video game user interface device that allows the user to play standard video games using realistic arm, leg and body movements which relate to the various activities portrayed in the video game being played. The device is sensitive to acceleration and outputs a signal to the video game controller when an acceleration is detected." U.S. Pat. No. 5,704,836, issued to Norton, et al., for "Motion-Based Command Generation Technology" discloses a command system that "optically monitors the movement of a subject and provides command signals to a computer system to control a graphic of a graphical user interface displayed on a monitor such as an animated character in a video game." Norton accomplishes this by using an "optical detector unit which continuously scans a subject frame in which a subject is positioned" and comparisons of scans of sub-regions in the frame to determine if the subject has moved. Once movement is detected, the graphical representation on a video screen can simulate the movement. U.S. Pat. No. 5,718,639, issued to Bouton, for "Opto-Electric Golf Club Swing Sensing System Having Vertically Offset Sensors" discloses a "video golf swing sensing system responsive to a user swinging a golf club" that "provides inputs to a video golf game operating on a personal computer having a monitor, a microprocessor, and a serial port." Bouton uses a sensing system comprising linear arrays of LEDs and photodetectors "for detecting a club head parameter by sensing light reflected off the club head." These gesture recognition apparatuses and methods in the prior art use sophisticated mapping schemes to let a user participate in simulated activities using motions that would be used in the real activity.

Particularly relevant to golf swing analysis are inventions in the prior art that measure certain characteristics of a golf swing such as club speed and position. U.S. Pat. No. 5,108,105, issued to Shimizu, for "Golf Practice Device" discloses a "golf practice device comprising a mat with at least two sensors arranged therein in the direction of a swing orbit of a head of a golf club. A swing time substantially from a start of a back swing to a point of an impact with a golf ball is calculated in response to signals output by the sensors, and the result is indicated so that a golfer can observe same and thus achieve a stable swing." U.S. Pat. No. 5,257,084, issued to Marsh, for "Golf Swing Measurement System" discloses "A technique for measuring golf swing tempo or clubhead speed for a golfer swinging a golf club through a tee area. Two parallel infrared (IR) transmitters transmit respective IR beams along predetermined lines toward the tee area. Respective IR sensors receive respective IR beams reflected from a reflector mounted to the shaft of the golf club, near the clubhead. Each IR sensor provides a respective output signal indicative of the passage of the golf club through a corresponding IR beam. Predetermined sequences of output signals from the IR sensors are detected and the differences in time between various output signals are measured to provide tempo and clubhead speed values for display on a LCD screen. The speed values can be compensated values as obtained from look-up tables." U.S. Pat. No. 5,692,965, issued to Nighan, et al., for "Golf Swing Training Device With Laser" discloses an apparatus that uses at least one laser device that provides a feedback signal to the golfer that is indicative of a position and a motion of the head during the top of a backswing of the golf club by the golfer." The laser device may also be used to project a beam that provides visual feedback to the user, such as by showing a path on the ground or the motion and position of the golf club head. U.S. Pat. No. 6,375,579, issued to Hart, for "Golf Swing Analysis System And Method" discloses a laser based system that uses a monochromatic laser projector to generate a series of light planes in space near the impact zone where the golf club impacts the golf ball and a laser-based attachment for the golf club. This system and method attempts to analyze an entire golf swing by measuring certain characteristics of a golf swing as it passes through the impact zone. U.S. Pat. No. 7,219,033, issued to Kolen, for "Single/Multiple Axes Six Degrees of Freedom (6DOF) Internal Motion Capture System with Initial Orientation Determination Capability" discloses "A highly miniaturized electronic data acquisition system includes MEMS sensors that can be embedded onto moving device without affecting the static/dynamic motion characteristics of the device. The basic inertial magnetic motion capture (IMMCAP) module consists of a 3D printed circuit board having MEMS sensors configured to provide a tri-axial accelerometer; a tri-axial gyroscope, and a tri-axial magnetometer all in communication with analog to digital converters to convert the analog motion data to digital data for determining classic inertial measurement and change in spatial orientation (rho, theta, phi) and linear translation (x, y, z) relative to a fixed external coordinate system as well as the initial spatial orientation relative to the known relationship of the earth magnetic and gravitational fields. The data stream from the IMMCAP modules will allow the reconstruction of the time series of the 6 degrees of freedom for each rigid axis associated with each independent IMMCAP module." Kolen further teaches putting an error representation on a display. U.S. Pat. No. 7,785,211, issued to Hackenberg, for "Golf Swing Trainer Having Balanced Center Of Mass" discloses a "golf swing trainer providing a resiliently flexible shaft having a first shaft end coupled to a swing element and a second shaft end coupled to a grip having a tapered external surface gripably received by the hands."

Inventions involving golf swing analysis have also involved attaching cameras to a golf club and using data produced by the camera to analyze the movement of the golf club. U.S. Pat. No. 7,536,033, issued to Kirby, for "Portable Swing Analyzer" discloses an apparatus with "an imaging system in communications with the sporting equipment to measure motion parameters. The imaging system may be located on the sporting equipment or, optionally, within the sporting equipment." The system may be used to determine the impact location of the sporting equipment with another object, the momentum transferred, the velocity of the sporting equipment and/or the angular orientation of the sporting equipment during a motion. Such determinations are accomplished by "(a) a means of taking sequential images attached to said swinging type piece of sporting equipment, the sequential images being of a background element that does not move with the sporting equipment; (b) a means of identifying a common pattern between two sequential images and calculating a displacement vector from the movement of said common pattern in communication with said means of taking sequential images; said displacement vector representing the displacement of said common pattern between said sequential images; (c) a means of interpreting said displacement vector in communication with said means of calculating a displacement vector, the interpretation providing the user a meaningful set of information concerning the use of said sporting equipment; and (d) a means of communicating to user said meaningful set of information concerning the use of said sporting equipment, in communication with said means of interpretation; whereby the user may analyze their performance in the use of said sporting equipment." Likewise, Japanese Patent number JP2010274089 discloses a golf training putter that "includes at least two or more cameras, one or more of which include the cameras at positions higher than a head in a shaft. An angle sensor is required at the same time." "[A] gyro sensor, an acceleration sensor and distance sensor are combined together. From information of the cameras, the swing orbit, a distance to the ball and an inclination between the ball and the cup are clarified."

Inventions involving golf swing analysis have also involved attaching lasers to a golf club and using the laser lines to analyze the golf swing movement of a golfer. U.S. Pat. No. 5,873,789, issued to Torriano, for "Golf Swing Training Device" discloses "A golf club shaped swing training device provides visual indication of club position during a club swinging motion. A first laser diode produces a first laser line from the upper end of the shaft and second and third laser diodes produce second and third laser lines respectively from the bottom face and the front face of the head portion of the device. Each of the laser lines emanates from the device as a concentrated beam to impinge and be readily visible on a training surface remote of the device for independently tracking movement of the shaft, the bottom face and the front face of the head portion of the device." U.S. Pat. No. 8,409,024, issued to Marty, et al., for "Trajectory Detection and Feedback System for Golf" discloses "Lining up the direction of the shot may take place in advance of the shot by positioning a laser line on the view of the virtual course. Then the calculated shot may be positioned on the virtual course based on how the actual swing and golf ball were struck. The system may allow communication connections that allow each of the players to see the results of their shots on the real or virtual course.

The prior art is deficient because it does not provide a system, apparatus or method of providing an attachment to a golf club that detects and measures the movement of the golf club through an entire swing, that displays the entire swing movement of the golf club on a graphical display along with relevant statistics, that provides coaching using theoretical and historical data with graphical and verbal feedback, and that corrects errors with great precision. The prior art is also deficient because it does not provide for swing plane analysis of an entire swing by simulating laser lines that would be reflected on the ground as if laser lights were mounted and aligned on a golf club shaft, each emitting light from a respective end of the golf club shaft. The gesture recognition techniques described above are deficient because they are merely used as input for games and simulations and are not used to record and analyze all major aspects of a full golf swing and to provide feedback and coaching to a user so that user may improve his or her golf game. The golf swing analysis techniques described above are deficient because they attempt to analyze an entire swing using only a small portion of the swing. limit the number of statistics or graphics, such as club speed or error representation, do not use a real golf club, or do not provide adequate error correction for the inertial measurements. Additionally, many inventions in the prior art require a fair amount of equipment, making them costly.

The prior art is also deficient because it lacks adequate error correction for measurements taken during an entire golf club swing. Error correction may be accomplished using a camera directed at the club head with image recognition software and data from a navigation system. The data from the camera and the image recognition software may be used to measure the distance between a golf ball and club head at address, the orientation of the apparatus relative to the club head face and the club head deflection throughout the swing and may be combined with data from the accelerometer and gyroscope to create data that more accurately reflects a golf swing.

The data from a navigation system may be used to correct errors caused by drift in gyroscope measurements and signal noise from both accelerometer and gyroscope sensors. Examples of such navigation systems are MIT's Cricket system and the system described in "Low Cost Inertial Navigation: Learning to Integrate Noise and Find Your Way" by Kevin J. Walchko, Thesis Presented to the Graduate School of the University of Florida in Partial Fulfillment of the Requirements for the Degree of Master of Science, University of Florida, 2002.

Cricket is an indoor location system for pervasive and sensor-based computing environments. Cricket provides fine-grained location information such as space identifiers, position coordinates, and orientation, to applications running on handheld devices, laptops, and sensor nodes for continuous object tracking. Cricket is intended for use indoors or in urban areas where outdoor systems like the Global Positioning System (GPS) do not work well. It can provide distance ranging and positioning precision of between 1 and 3 cm, so applications that benefit from better accuracy than the cellular E-911 services and GPS will also find Cricket useful. Cricket is designed for low-power operation and can be used as a location-aware sensor computing node (running TinyOS), to which a variety of sensors can be attached. Cricket uses a combination of RF and ultrasound technologies to provide location information to attached host devices. Wall- and ceiling-mounted beacons placed through a building publish information on an RF channel. With each RF advertisement, the beacon transmits a concurrent ultrasonic pulse. Listeners attached to devices and mobiles listen for RF signals, and upon receipt of the first few bits, listen for the corresponding ultrasonic pulse. When this pulse arrives, the listener obtains a distance estimate for the corresponding beacon by taking advantage of the difference in propagation speeds between RF at the speed of light and ultrasound at the speed of sound. The listener runs algorithms that correlate RF and ultrasound samples (the latter are simple pulses with no data encoded on them) and that pick the best correlation. Even in the presence of several competing beacon transmissions, Cricket achieves good precision and accuracy quickly.

The inertial navigation system described by Walchko uses an inertial measurement unit (IMU) and a global positioning system (GPS) to allow inertial navigation in noisy environments, such as those outdoors. The IMU uses accelerometers and gyroscopes to interpolate positions between 1 HZ GPS positions. Walchko's system corrects bias from the IMU caused by the effects of gyroscope drift, temperature, hysteresis and vibrations.

Accordingly, it would be desirable to provide a lightweight attachment to a golfer's actual golf club that detects and measures the movement of a full golf swing, that analyzes the entire golf swing, that provides comprehensive statistics for every point of an entire swing, that displays the movement of the entire swing on a graphical display with the comprehensive statistics, that displays laser lines on a graphical display that would be drawn on the ground during the entire swing as if lasers were attached and linearly aligned to the head and the tail of the shaft of a golf club for swing plane analysis, and that coaches the golfer on how to improve the swing using theoretical and historical data. This can be accomplished by attaching an apparatus of negligible weight to the shaft or top of a golf club where the apparatus comprises a 3-axis accelerometer, a 3-axis gyroscope, computer memory, a microprocessor, a transmitter, and a battery such that it communicates with a computer application running on a mobile device, such as a smart phone, tablet computer, or a laptop computer. To compensate for differences in the angles that individual golfers address a ball, a 3-axis magnetometer can be used to select the target line on which a golfer wishes to aim. Additionally, it would also be desirable to include a camera in the lightweight attachment and to use image recognition software to measure the distance between the club head and the ball at address, the rotation of the club during the swing, and the movement of the club head relative to the movement of the shaft of the club. It would further be desirable to correct bias from the accelerometers and gyroscopes caused by the effects of gyroscope drift, temperature, hysteresis and vibrations in outdoor environments using a combination of RF and ultrasound technologies to provide location information to attached host devices. Accelerometer and gyroscope error would also be desirably corrected and made more precise by determining object speeds and coordinates using image sensors in three dimensions as part of the apparatus. Another desirable feature would be to utilize a camera on the tablet computer or other mobile device to capture and to automatically trim real-time video of the player's shot to create a video duplication of the animated view of the shot for side-by-side comparison so the user may see what actions of the user may be introducing errors or corrections in the swing.

The inventions discussed in connection with the described embodiment address these and other deficiencies of the prior art. The features and advantages of the present inventions will be explained in or apparent from the following description of the preferred embodiment considered together with the accompanying drawings.

SUMMARY OF THE INVENTION

The present inventions address the deficiencies of the prior art of golf swing analysis and coaching. Particularly, a small attachment of negligible weight that is securable to the shaft of a golf club, or mountable inside a hollow golf club, is used to communicate to an application running on a mobile device, such as a smart phone, a tablet computer, or a laptop computer. The attachment uses a transmitter to send processed linear and angular movement data that defines a golf swing to a receiver on the mobile device. A computer application running on the mobile device receives the processed data, processes the data further and displays a graphical representation of the entire swing with comprehensive statistics for every point of the swing. The processed linear and angular movement data may also be used to simulate and display a graphical representation of laser lines that would be drawn on the ground if lasers were attached and linearly aligned to the head and the tail of the shaft of a golf club for swing plane analysis. The processed data is stored and later used along with theoretical data to coach a golfer on his or her swing. Error correction is used on the linear and angular movement data for accuracy and precision. Thus, unlike the prior art, a golfer can fully analyze a golf club swing at every point of the swing and make proper adjustments at any point in the swing to improve the swing.

More particularly, the present inventions include a three-axis accelerometer capable of producing and transmitting linear acceleration data, a three-axis gyroscope capable of producing and transmitting angular velocity data, a first microprocessor that receives data from the accelerometer and the gyroscope and processes the data, a first computer memory wherein the microprocessor stores the processed data, and a radio transmitter for transmitting the processed data from the first computer memory. The inventions are powered by a battery or other suitable power source. A housing is used to hold the accelerometer, the gyroscope, the microprocessor, the first computer memory, the radio transmitter, and the battery. MEMS technology may be used for the accelerometer and the gyroscope. Other suitable motion detectors may be used that provide the same functionalities as the accelerometer and the gyroscope. Flash memory may be used as the computer memory. To compensate for differences in the angles that individual golfers address the ball, a 3-axis magnetometer may be used to select the target line on which a golfer wishes to aim. Thus, a golfer may account for that golfer's natural slice or hook.

The inventions further have a portable device, such as a smart phone, a tablet computer, or a laptop computer, that includes a radio receiver, a second computer memory for storing data received by the radio receiver, a third computer memory for storing a computer program that processes the data in the second computer memory, a second microprocessor for controlling the computer program and for processing the data received by the radio receiver into graphical data and statistical data, a fourth computer memory for receiving graphical data and statistical data from the second microprocessor, and a graphics display.

The housing, which is of negligible weight so that it does not affect a golf swing, attaches to a the shaft of the golf club below the grip or at the top of the grip or inside the shaft, and, when a user swings the golf club, the accelerometer communicates linear acceleration data defining the linear movements of the golf club to the first microprocessor and the gyroscope communicates angular velocity data defining the angular movements of the golf club to the first microprocessor. The first microprocessor processes the linear acceleration data and the angular velocity data, stores the processed data in the first computer memory, and uses the radio transmitter to transmit the processed data to the radio receiver on the portable device. The radio receiver stores the processed data in the second computer memory. The computer program stored in the third computer memory is controlled by the second microprocessor to store graphical data and statistical data in the fourth computer memory and to display the graphical data and the statistical data on the graphics display as an image of the movement of the golf club along with related statistics. Using the display and the statistics, the user will be able to analyze the swing at any point and try to improve his or her golf swing. The housing may also be the hollow shaft of a golf club.

In described embodiments of the present inventions, the graphics display shows an interactive three-dimensional animation of the swing wherein the animation can be played as slowly or as quickly as a user desires, the animation can be played from any angle, and the animation can be played at any magnification. Additionally, the graphics display can show the position, orientation, and speed of the golf club at any point throughout the swing. Also, the graphics display shows metrics that allow one to analyze a golf swing such as club head speed at any point in the swing, club and ball path, tempo, top of backswing, angle of attack, relevant planes, and relevant angles. Embodiments of the inventions provide further analysis wherein the computer program compares the position of the club when the user aims with the position of the club on impact and calculates the difference in loft, lie and club face angles between the two positions to allow the user to compare what the user meant to do with what actually happened. Embodiments of the inventions also provide verbal instructions and analysis of the golf club swing.

The present inventions may also include a user input device for inputting a user's biometric data and a fifth computer memory for storing user biometric data wherein the second microprocessor controls the computer program to factor the user biometric data into the processed data.

The described inventions may also be used with a website wherein the second microprocessor controls the computer program in the third computer memory to upload the graphical data and the statistical data from the fourth computer memory to the website for personal review and for sharing with other users. Consequently, the website provides coaching based on the processed data. The website also allows a user to compare multiple swings at once using that user's history of uploaded swings, allows a user to enter biometric data and to view baseline swings for that user's body type, and allows a user to see professional and theoretical swings, which allows a user to see trends over time and get objective progress data.

Some embodiments of the present inventions include a first microprocessor that inputs, processes and outputs data, a three-axis accelerometer that outputs linear acceleration data to the first microprocessor, a three-axis gyroscope that outputs angular velocity data to the first microprocessor, and a camera that outputs real-time image data to the first microprocessor. A first computer memory receives data output from the first microprocessor, and a radio transmitter transmits data from the first computer memory. A housing, attachable to a golf club, holds the first microprocessor, the accelerometer, the gyroscope, the camera, the first computer memory, and the radio transmitter. The camera is directed at the club head. A portable device, such as a smart phone, a tablet computer or a portable computer, is used to receive the transmission from the radio transmitter. The portable device includes a radio receiver, a second microprocessor that inputs, processes and outputs data received by the radio receiver, a second computer memory that receives data output from the second microprocessor and a graphics display. A third computer memory stores a computer program in communication with one or both of the first microprocessor and the second microprocessor and instructs the one or both of the first microprocessor and the second microprocessor to process data in one or both of the first computer memory and the second computer memory into graphical data and statistical data using image recognition to process real-time image data from the camera and using position and movement recognition to process real-time movement and position data from the accelerometer and the gyroscope. Thus, the data produced by the accelerometer, the gyroscope and the camera may be processed within the housing or it may be offloaded to the portable device for processing. The offloading transmission may be via a live stream using Bluetooth or another similar protocol. These embodiments provide all the capabilities described above in addition to integrating the data produced by the camera with the data produced by the accelerometer and the gyroscope to correct for initial club head position, shaft deflection and rotation and other club head position-related characteristics. These embodiments may also provide the graphical representations, the user input capabilities and the website interactions described above. To lessen transmission trouble due to limited bandwidth, some embodiments only transmit data from the first computer memory when the accelerometer senses movement.

Further embodiments of the present inventions include a system for analyzing a golf club swing that has a multiplicity of base stations arranged in three-dimensional space relative to a horizontal plane. Each base station includes an ultrasonic transmitter that transmits an ultrasonic pulse at a frequency different than the frequency transmitted by any of the other ultrasonic transmitters in the other base stations, a first ultrasonic receiver, a first radio transmitter that transmits a radio frequency pulse, and a first radio receiver. A triangulation processor communicates with the first ultrasonic receiver and the first radio receiver and inputs the ultrasonic and radio frequency pulses from the other base stations. Triangulation is then used to determine the relative positions of the multiplicity of base stations and to build a general coordinate system. Data defining the general coordinate system is transmitted by the first radio transmitter. These embodiments also have a periodic pulse generator that periodically transmits an ultrasonic pulse using the ultrasonic transmitter and a radio frequency pulse using the first radio transmitter.

The systems in the described embodiments also include an apparatus attachable to a golf club that has a first microprocessor that inputs, processes and outputs data, a three-axis accelerometer that outputs linear acceleration data to the first microprocessor, a three-axis gyroscope that outputs angular velocity data to the first microprocessor, a second ultrasonic receiver that receives ultrasonic pulses transmitted from the multiplicity of base stations and that outputs data to the first microprocessor, a second radio receiver that receives radio pulses transmitted from the multiplicity of base stations and that outputs data to the first microprocessor and a first computer memory that receives data output from the first microprocessor. A second radio transmitter transmits data from the first computer memory. A housing, attachable to a golf club, is used to hold the first microprocessor, the accelerometer, the gyroscope, the second ultrasonic receiver, the second radio receiver, the first computer memory and the second radio transmitter. The systems in the described embodiments further include a portable device, such as a smart phone, a tablet computer or a portable computer, having a third radio receiver, a second microprocessor that inputs, processes and outputs data received by the third radio receiver, a second computer memory that receives data output from the second microprocessor and a graphics display. As with earlier described embodiments, a third computer memory stores a computer program in communication with one or both of the first microprocessor and the second microprocessor and instructs the one or both of the first microprocessor and the second microprocessor to process data in one or both of the first computer memory and the second computer memory into graphical data and statistical data using position and movement recognition to process real-time movement and position data from the accelerometer, the gyroscope and the multiplicity of base stations. These embodiments provide all the capabilities described above for systems without a camera in addition to integrating the data produced by the transmitters with the data produced by the accelerometer and the gyroscope to correct for drift from integrating the accelerometer data. These embodiments may also provide the graphical representations, the user input capabilities and the website interactions described above. To lessen transmission trouble due to limited bandwidth, some embodiments only transmit data from the first computer memory when the accelerometer senses movement.

Still other embodiments may use both the camera and the ultrasonic and RF technology described above in a single system, apparatus or method. In systems without a camera, a three-axis magnetometer capable of transmitting directional orientation data to the first microprocessor may be used to initialize the orientation of a golf club.

Further embodiments of the described inventions include an apparatus for analyzing a golf club swing that has a first microprocessor that inputs, processes and outputs data, a three-axis accelerometer that outputs linear acceleration data to the first microprocessor, a three-axis gyroscope that outputs angular velocity data to the first microprocessor, a first computer memory that receives data output from the first microprocessor, a radio transmitter that transmits data from the first computer memory, and a housing, attachable to a golf club, that holds the first microprocessor, the accelerometer, the gyroscope, the first computer memory and the radio transmitter. These further embodiments also include a portable device having a radio receiver, a second microprocessor that inputs, processes and outputs data received by the radio receiver, a second computer memory that receives data output from the second microprocessor, and a graphics display. In these further embodiments, a third computer memory stores a computer program in communication with one or both of the first microprocessor and the second microprocessor that instructs the one or both of the first microprocessor and the second microprocessor to process data in one or both of the first computer memory and the second computer memory. The computer program has a first orientation module that takes linear acceleration data and angular velocity data as input and outputs orientation data defining position and movement of a swinging golf club over a period of time. A second orientation module takes linear acceleration data and angular velocity data as input and outputs orientation data defining simulated laser lines drawn as if laser lights were mounted and aligned on a golf club shaft, each emitting light from a respective end of the golf club shaft. In these embodiments, a statistics module calculates golf swing related statistics, and a graphics module in communication with the first orientation module, the second orientation module, the statistics module and the graphics display draws graphics on the graphics display defining the movement of a golf club during a golf swing with orientation data output from the first orientation module, draws graphics on the graphics display defining laser lines drawn during a golf swing when two lasers are aligned with the shaft of a golf club with orientation data output from the second orientation module and draws statistics on the graphics display with data output from the statistics module. These embodiments may be set up so that the radio transmitter only transmits data from the first computer memory when the accelerometer senses movement.

In these embodiments, a three-axis magnetometer may be used within the housing to output directional orientation data to the first microprocessor as input for the first orientation module and the second orientation module. Also, a camera may be used within the housing to output real-time image data to the first microprocessor as input for the first orientation module and the second orientation module where the first orientation module and the second orientation module use image recognition to reduce error when defining the orientation of the golf club. The housing may be attached to the shaft of a golf club below the grip such that the camera is directed at the club head.

Also in these embodiments, the radio transmitter may be a second radio transmitter wherein the radio receiver is a second radio receiver and the embodiments further have a multiplicity of base stations arranged in three-dimensional space relative to a horizontal plane. Each base station has an ultrasonic transmitter that transmits an ultrasonic pulse at a frequency different than the frequency transmitted by any of the other ultrasonic transmitters in the other base stations, a first ultrasonic receiver, a first radio transmitter that transmits a radio frequency pulse, a first radio receiver, a triangulation processor in communication with the first ultrasonic receiver and the first radio receiver that inputs the ultrasonic and radio frequency pulses from the other base stations and uses triangulation to determine the relative positions of the multiplicity of base stations and that builds a general coordinate system, which is transmitted by the first radio transmitter, and a periodic pulse generator that periodically transmits an ultrasonic pulse using the ultrasonic transmitter and a radio frequency pulse using the first radio transmitter, wherein the housing further holds a second ultrasonic receiver that receives ultrasonic pulses transmitted from the multiplicity of base stations and that outputs orientation data to the first microprocessor as input for the first orientation module and the second orientation module, and a second radio receiver that receives radio pulses transmitted from the multiplicity of base stations and that outputs orientation data to the first microprocessor as input for the first orientation module and the second orientation module.

Further in these embodiments, the graphics module shows an interactive three-dimensional animation of the swing that can be played as slowly or as quickly as a user desires and that can be played from any angle and at any magnification and wherein the graphics display can show the position, orientation, and speed of the golf club at any point throughout the swing. The graphics module also shows metrics and graphics that allow one to analyze a golf swing, such as club head speed at any point in the swing, club and ball path, tempo, top of backswing, angle of attack, relevant planes, variation in the swing plane during the swing using laser lines and relevant angles, and wherein the computer program compares the position of the club when the user aims with the position of the club on impact and calculates the difference in loft, lie and club face angles between the two positions to allow the user to compare what the user meant to do with what actually happened.

Additionally, in these embodiments, a website may be used wherein the second microprocessor controls the computer program in the third computer memory to upload graphical data and statistical data to the website for personal review and for sharing with other users, wherein the website provides coaching based on the processed data, and wherein the website allows a user to compare multiple swings at once using that user's history of uploaded swings, allows a user to enter biometric data and to view baseline swings for that user's body type, and allows a user to see professional and theoretical swings, which allows a user to see trends over time and get objective progress data.

In these embodiments, a user input device may be used for inputting a user's biometric data wherein the second microprocessor controls the computer program to factor the user biometric data into the processed data.

A camera on the tablet computer or other mobile device may be used to align and to capture and automatically trim real-time video of the player's shot to create a video duplication of the animated view of the shot for side-by-side comparison. While video capture will begin before a player's shot begins and end after a player's shot ends, a six degrees of freedom (6-DOF) inertial measurement unit, or other motion capture device, may be used to detect the beginning of the shot and impact. The video may then be trimmed to start and end moments before and after the swing starts and ends, respectively. To reduce or eliminate video shift, motion capture techniques can be used to locate the golf ball in the camera frame and identify the frame during which the ball disappears. This frame can be used as the impact frame, and the video can be re-synchronized.

Certain embodiments of the described inventions focus on error correction and precision in the linear and angular movement data by using optical image sensors and optical correlators to generate speeds and coordinates of a moving object. These embodiments disclose a system for analyzing a golf swing that includes an apparatus for attachment to a golf club, the apparatus having a housing for attachment of the apparatus to a golf club, a power source in the housing, a three-axis accelerometer in the housing for generating linear acceleration data from the apparatus, and a three-axis gyroscope in the housing for generating angular velocity data from the apparatus. The accelerometer and the gyroscope may use MEMS or some similar technology. The golf club may also be considered part of the apparatus.

In the apparatus, these embodiments also have a three-dimensional image sensor in the housing for generating coordinate and speed data defining the coordinates and the speed of an object moving within a three-dimensional space defined by three orthogonally aligned axes. The three-dimensional image sensor includes 1) one of a combination of three linear image sensors and a combination of one two-dimensional linear image sensor and one linear image sensor for generating data defining successive optical images along three orthogonally aligned axes, 2) a plurality of optical correlators in communication with the image sensors with one optical correlator per image sensor for receiving, comparing and correlating the successive optical images and for generating data defining the correlation of the successive optical images, 3) a plurality of delay units in communication with the image sensors and the optical correlators with one delay unit per image sensor that delay the optical correlators from comparing and correlating the successive optical images until the data for comparison and correlation has been communicated from the image sensors to the optical correlators, and 4) a moving object speed and coordinate calculator in communication with the optical correlators for generating the coordinate and speed data. The three-dimensional image sensor may be contained in a field-programmable gate array. The three-dimensional image sensor may also be augmented with a microcontroller unit coupled to the one of a combination of three linear image sensors and a combination of one two-dimensional linear image sensor and one linear image sensor and in communication with the moving object speed and coordinate calculator and the radio transmitter wherein the microcontroller unit controls the power to the one of a combination of three linear image sensors and a combination of one two-dimensional linear image sensor and one linear image sensor and wherein the data from the moving object speed and coordinate calculator is processed through the microcontroller unit to the radio transmitter.

Further accuracy may be achieved where the systems recited further use a three-axis magnetometer capable of transmitting directional orientation data to the first microprocessor because initial orientation may be more accurately established.

The apparatus in these embodiments further have a first microprocessor in the housing and in communication with the accelerometer, the gyroscope and the three-dimensional image sensor for receiving the linear acceleration data, the angular velocity data and the coordinate and speed data. A first computer memory in the apparatus is used in the housing and in communication with the first microprocessor. A radio transmitter, in the apparatus in the housing and in communication with the first microprocessor, transmits the linear acceleration data, the angular velocity data and the coordinate and speed data from the first computer memory. The accelerometer, the gyroscope, the magnetometer and the three-dimensional image sensor, the first microprocessor, the first computer memory and the radio transmitter may be combined into a single motion detector.

Along with the apparatus, the system of these described embodiments include a portable device, such as an iPhone™, a laptop computer, a tablet computer and other similar devices. The portable device includes a radio receiver in communication with the radio transmitter that receives the linear acceleration data, the angular velocity data and the coordinate and speed data from the radio transmitter. The portable device also includes a second computer memory in communication with the radio receiver that stores the linear acceleration data, the angular velocity data and the coordinate and speed data. A third computer memory in the portable device is used for storing a computer program that processes the data in the second computer memory. A second microprocessor in the portable device and in communication with the second computer memory and the third computer memory inputs the angular velocity data, the linear acceleration data and the coordinate and speed data from the second computer memory and uses the coordinate and speed data to correct errors in the angular velocity data and the linear acceleration data. The second microprocessor is further in communication with the second computer memory and the third computer memory, where the second microprocessor controls the computer program to process the linear acceleration data, the angular velocity data and the coordinate and speed data received by the radio receiver into graphical data and statistical data and to transmits the graphical data and statistical data to a fourth computer memory in communication with the second microprocessor that receives and stores the graphical data and statistical data. A graphics display is used to display the graphical data and statistical data in the fourth memory as an image of the movement of the golf club along with related statistics.

Error correction in these embodiments may be further enhanced 1) when the second microprocessor is further in communication with the second computer memory and the third computer memory, where the second microprocessor inputs angular velocity data from the second computer memory, outputs data representing coordinates estimating the position of the gyroscope corresponding with a 0-error in angular velocity data, outputs values defining an error trend of the angular velocity data from the gyroscope, and uses the angular velocity data from the second computer memory to output data representing the initial orientation of the gyroscope and 2) when the second microprocessor is further in communication with the second memory and the third memory, where the second microprocessor inputs linear acceleration data from the second computer memory and outputs data representing coordinates where the accelerometer produced data that indicates a shock.

In these embodiments, as described for other embodiments, the graphical data further includes data for creating images of simulated laser lines on the graphics display. Furthermore, the portable device may further use a camera aligned to capture a three-dimensional video image of a user swinging a golf club, and the computer program may trim the video image to align and synchronize with the image of the movement of the golf club. The output is the trimmed video image and the image of the movement of the golf club side-by-side on the display.

Some embodiments of the described inventions include motion attributes recognition systems and methods, and, more specifically, described embodiments recognize faults in the movements of a golfer's swings. Consequently, further embodiments include virtual coaching systems and methods on electronic devices that recognize the faults as attributes of the golfer's imperfect swing based on the golfer's motion data and that provide feedback in the form of information and advice. Thus, a golfer may use an electronic device to receive golf swing coaching.

BRIEF DESCRIPTION OF THE DRAWINGS

The inventions will now be more particularly described by way of example with reference to the accompanying drawings. Novel features believed characteristic of the inventions are set forth in the claims. The inventions themselves, as well as the preferred mode of use, further objectives, and advantages thereof, are best understood by reference to the following detailed description of the embodiment in conjunction with the accompanying drawings, in which:

FIG. 25C shows a screen shot on a mobile electronic device of a lesson plan for correcting top faults in the golf club swings.

FIG. 25D shows a screen shot on a mobile electronic device of a lesson summary in text form and interchangeable with a lesson summary in video form.

FIG. 28F shows a screen shot for showing a swing animation and the top ten matches from the stored swings database.

DETAILED DESCRIPTION OF THE EMBODIMENTS

Figure 1A:
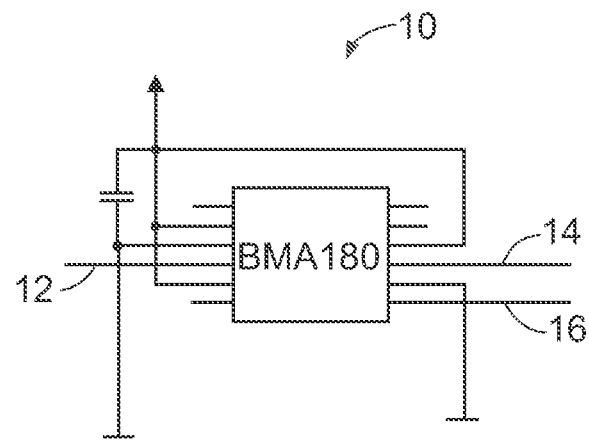
FIG. 1A shows a schematic of an accelerometer.

The described embodiment is a three-dimensional golf swing analyzer for use with an application on a smart phone, a tablet computer, a laptop computer, or other similar mobile device. The device works as an Inertial Measurement Unit (IMU) attached to the shaft of a golf club to record and transmit the accelerations undergone by the club. It captures and analyzes golf swing data using a compact and lightweight sensor that attaches to any golf club either below the grip or on the cap or is integrated into the shaft. After hitting a shot or swinging the club, players and instructors can view an interactive, three-dimensional animation of the swing with laser lines defining swing planes throughout the swing, along with key metrics, such as club head speed, path, plane, and various angles at impact. The user is able to see the key metrics for any point in the swing. The user can also play back the swing at any speed, from any angle, and at any magnification. Since the described embodiment is not based on video capture, but rather recording the actual position and orientation of the golf club at $\frac{1}{1000}^{th}$ of a second intervals, there are virtually no limits on the granularity of the playback. By comparing the position of the club when aiming with the position of the club at impact, the application calculates the difference in loft, lie and club face angles between the two positions, allowing the user to compare what the user meant to do to what actually happened. Additionally, the application computes club head speed at impact and at all other points in the swing, tempo, top of backswing, angle of attack, club head path, and other vital characteristics. The application further provides verbal instruction and suggestions to fix common defects in a swing, such as taking the club too far back and an over-the-top swing.

The data captured may also be automatically uploaded to a website where users can access and review their historical information or share it with an instructor. The website provides additional analytics by offering advanced comparison features, allowing the user to compare multiple swings at once, including his or her own history, and baseline swings for his or her body type, as well as professional and theoretical swings. This allows the user to see trends over time and get objective data about individual progress as a golfer. This also builds the foundation for an objective instructor ranking system. The website also provides users a way to send their swing data to a third party for review. This can be used for a golfer who travels to a different part of the country for the season but who still wants to receive instruction from a teacher back home.

The following definitions are used herein:
¼ way—the point in the backswing when the club is parallel to the ground for the first time
Half-way—the point in the backswing when the projection of the club onto the earth's y-z plane is perpendicular to the horizon for the first time
¾ way—the point in the downswing when the club is parallel to the ground for the first time
tobs (Top-of-backswing)—The point in the swing where the club reverses direction
Speedpoint—The point in the swing where the club attains maximum speed
Plane angle—The angle computed at any time by taking the club's Y vector in terms of the earth's coordinate system, at the current point in the swing, and the one immediately past it. The cross product of the two vectors is taken, which produces a vector orthogonal to both of them, and the normal vector of the plane defined by the two initial vectors. The plane angle is then the angle between the earth's x-z plane and the newly computed plane.
Club face to plane angle—The club's plane is computed at address. The club face to plane angle is the angle between the x-vector of the club and this initial plane.
Club face to horizon angle—This club face to horizon angle is the angle between the x-vector of the club and the x-z plane.

The following definitions are some parameters that may be derived from the output of the apparatus:
Swing tempo/club head speed at all points throughout the swing
Point of release—the point of the swing when the wrist angle is released during the downswing
Swing plane—determine the swing plane based on address and laser lines, and show deviation from it throughout the swing
Club face/loft/lie angles—the difference in angles between address and impact
Angle of attack—the angle of attack in the milliseconds preceding the impact
Launch direction and speed—the initial speed and direction of travel for the ball based on the impact data and the club used
Torque—the amount of torque generated by the swing at all points throughout the swing
Ball spin
Ball flight path
Ball flight distance The following data are observed from usage and may be used in analysis:
Location of use (via GPS in the user's phone)
Frequency of use
The following parameters are user defined and entered using the application on the mobile device:
Club used
Club deflection—Using the club information provided by the user and the observed torque, the application can calculate how much the club shaft will deflect.
User demographics such as age, sex, body type, handicap, frequency of play, etc.

FIG. 1A shows a schematic of an accelerometer 10. In the described embodiment, the Bosch™ BMA180 three-axis MEMS accelerometer 10 is used, although other accelerometers may be used. In the schematic shown in FIG. 1A, the data coming from the accelerometer 10 is controlled by a linear acceleration interrupt output 12, labeled INT1, which causes the linear acceleration related data to be output on the serial data in/out line 14 to a microcontroller (described below). The accelerometer 10 is synchronized with the microcontroller using a serial clock 16.

Figure 1B:
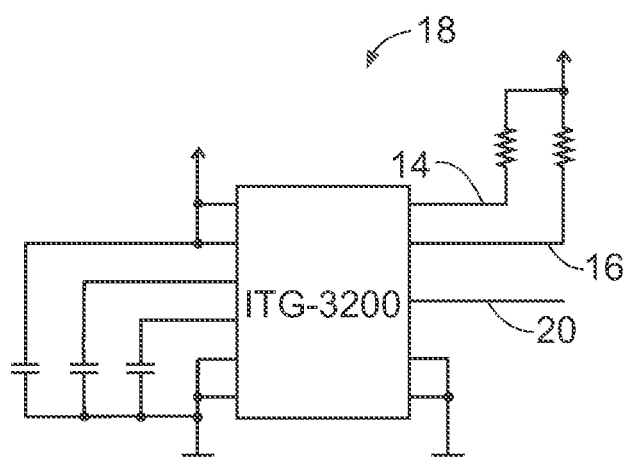
FIG. 1B shows a schematic of a gyroscope.

FIG. 1B shows a schematic of a gyroscope 18. In the described embodiment, the Invensense™ ITG3200 three-axis MEMS gyroscope 18 is used, although other gyroscopes may be used. In the schematic shown in FIG. 1B, the data coming from the gyroscope 18 is controlled by an angular velocity interrupt output 20, labeled INT2, which causes the angular velocity related data to be output on the serial data in/out line 14 to a microcontroller (described below). The gyroscope 18 is synchronized with the microcontroller using a serial clock 16. Note that the accelerometer 10 and the gyroscope 18 operate with a shared serial data bus and are multiplexed using the two interrupts.

Figure 1C:
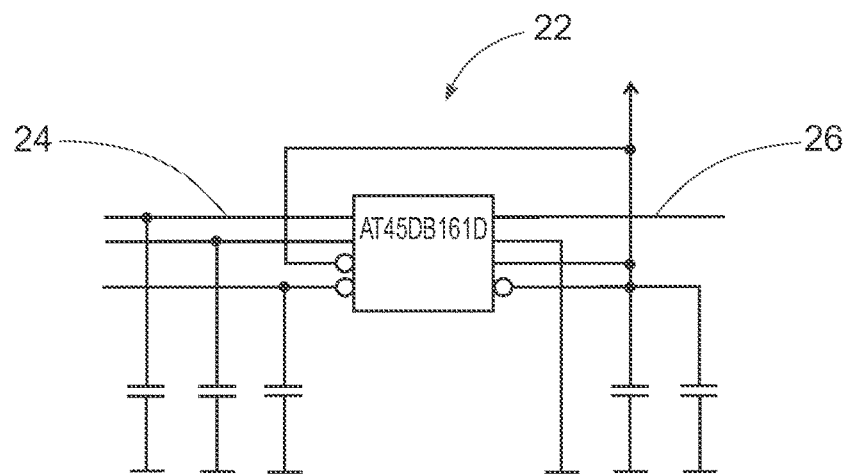
FIG. 1C shows a schematic of flash memory.

FIG. 1C shows a schematic of flash memory 22 that is used to store the data processed by the microcontroller. In the described embodiment, the Atmel™ AT45DB161D is used, although other memory may be used. In the schematic shown in FIG. 1C, processed data from the microcontroller comes in on the flash data input line 24 and, later, the data is output on the flash data output line 26 for transmission using a transmitter.

Figure 1D:
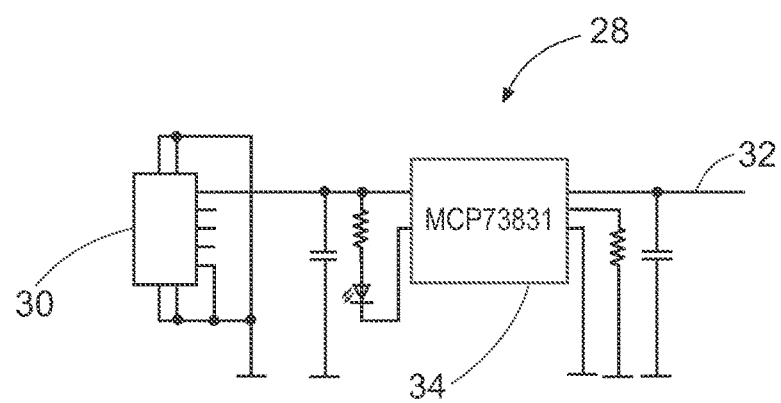
FIG. 1D shows a schematic of a battery charger.

FIG. 1D shows a schematic of the battery charger 28 that connects to a USB port 30 of the mobile device, which may be a smart phone, a tablet computer, a laptop computer, or any other similar device. The USB port 30 is used only to provide charging power to the device. FIG. 1D shows that the described embodiment uses a Microchip MCP73831 charge management controller 34, but other charge management controllers may be used. The power circuitry of the device provides charge on the battery charger line 32 to a battery 36 as shown in FIG. 1E.

Figure 1E:
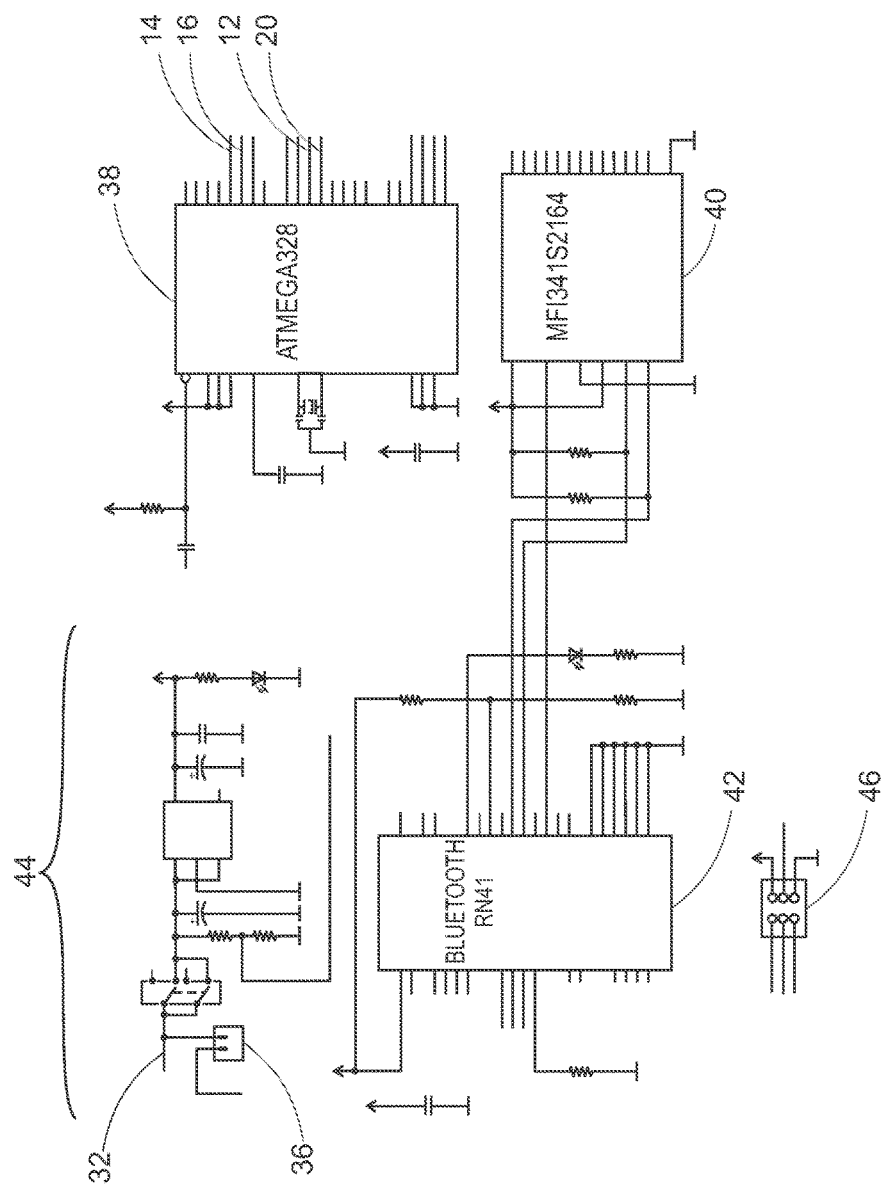
FIG. 1E shows a schematic of a microcontroller, co-processor, radio transmitter, and power control.

FIG. 1E shows a schematic of a microcontroller 38, co-processor 40, radio transmitter 42, and power control 44. This figure shows the layout of the various components utilized and reveals how the serial data in/out line 14 and the serial clock 16 come into the microcontroller 38 on the shared bus. In the described embodiment, the microcontroller 38 is an Atmel ATmega328, although other microcontrollers may be used. This figure also reveals how the linear acceleration interrupt output 12 and the angular velocity interrupt output 20 are connected to the microcontroller 38. Further shown in FIG. 1E is how a co-processor 40 is used to assist the transmission of processed data using a radio transmitter 42. In the described embodiment, the co-processor 40 is an Apple™ MFI341S2164, although other co-processors may be used. Under the control of the microcontroller 38, the co-processor 40 communicates to a radio transmitter 42 to transmit data to a mobile device. In the described embodiment, the radio transmitter 42 is a Bluetooth RN41, although other radio transmitters may be used. Although the function of the radio transmitter 42 is to transmit processed golf swing data, the radio transmitter 42 should be a device that may also be used as a receiver to allow remote updating of the firmware within the device. Lastly, FIG. 1E shows the USB connector 46 used to connect to a power source for charging the battery 36.

Figure 1F:
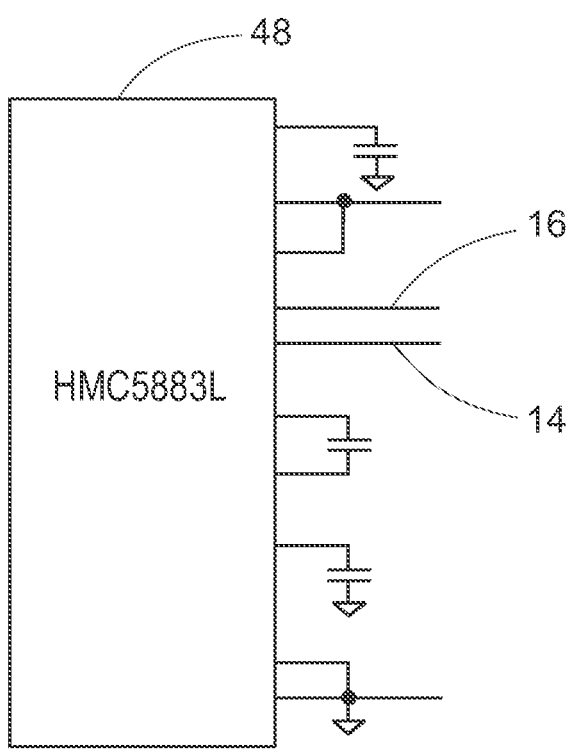
FIG. 1F shows a schematic of a magnetometer.

FIG. 1F shows a schematic of a magnetometer 48. In the described embodiment, the Honeywell™ HMC5883L digital three-axis magnetometer 48 is used, although other magnetometers may be used. FIG. 1F shows the serial data in/out line 14 and the serial clock 16 that are part of the shared serial bus. The magnetometer is used to let a user set a target line for the golf swing. This is important because each golfer displays variation in how that golfer addresses the ball and because each golfer has a different degree of natural slice or hook, including no slice or hook at all. Thus, if a golfer can choose a target line, then the actual shot can be compared to the target line for analysis and criticism. Without the target line, there is no accounting for the natural variations in how golfers address the ball. To activate this function with the magnetometer 48, a golfer starts by horizontally pointing the club, with the head down, along the desired target line, and then rotates the head of the club 180 degrees so that the club head points upward. Then, the target line will be established as the line in the direction that golf club shaft is pointing.

Figure 2A:
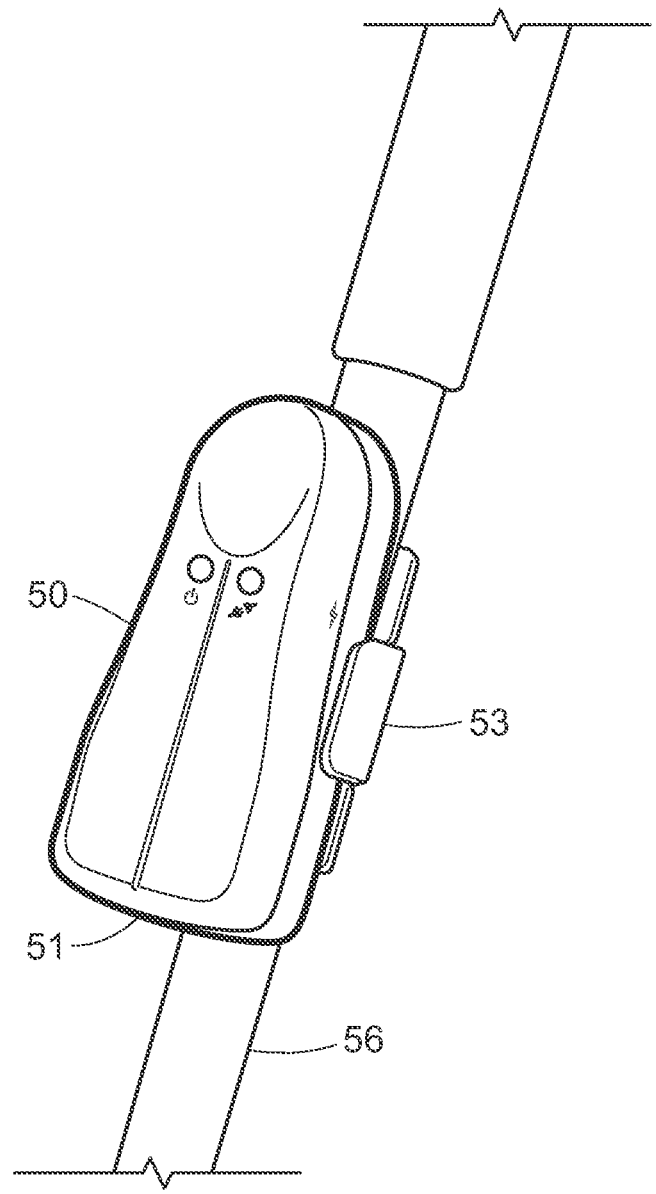
FIG. 2A shows a front perspective view of the housing attached to a golf club.
Figure 2B:
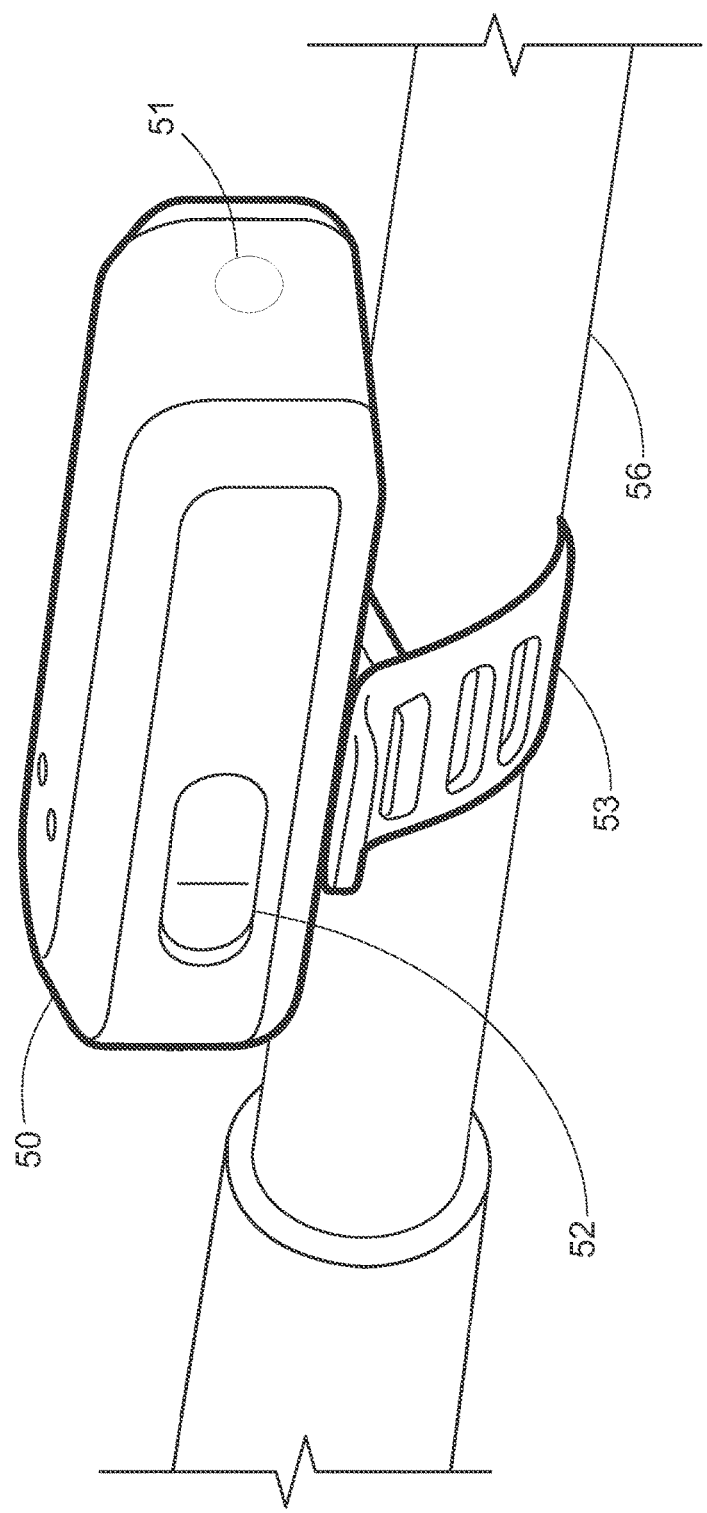
FIG. 2B shows a side perspective view of the housing attached to a golf club.
Figure 2C:
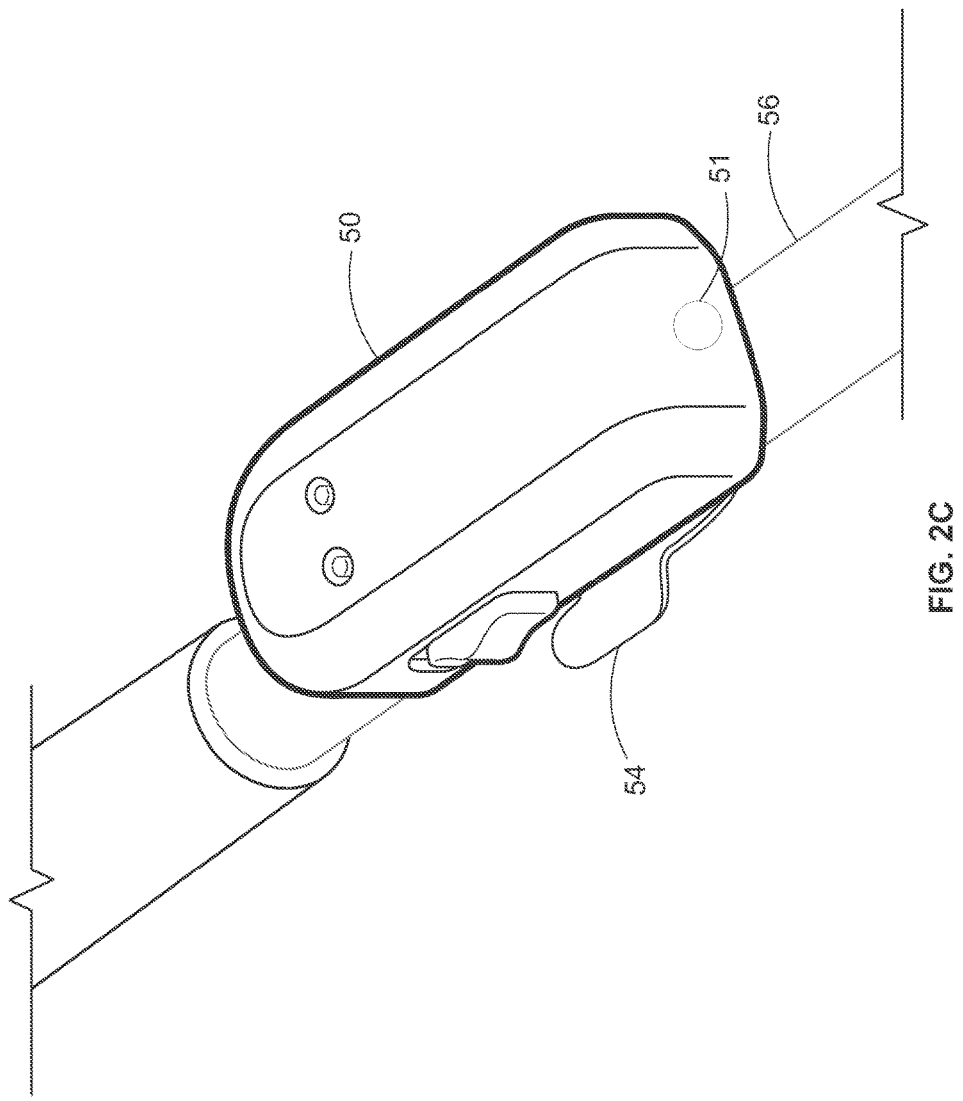
FIG. 2C shows an overhead, angled view of the housing and the strap fastener used.

FIG. 2A shows a front perspective view of the housing 50 attached to a golf club 56. This figure shows one variation on how the housing 50 may be attached to the golf club 56 using a strap 53 around the shaft of the golf club 56. FIG. 2B shows a side perspective view of the housing 50 attached to a golf club 56. Notable on this figure is the on/off switch 52, which is in close proximity to a golfer's hand and easily toggled. FIG. 2C shows an overhead, angled view of the housing 50 and the strap fastener 54 used.

Figure 3A:
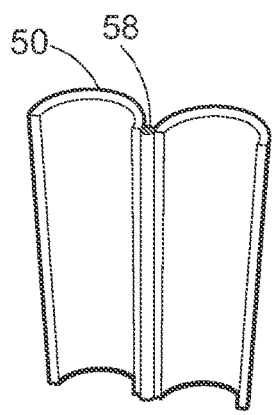
FIG. 3A shows a hinge and clasp clamp design for attaching the housing to a golf club.
Figure 3B:
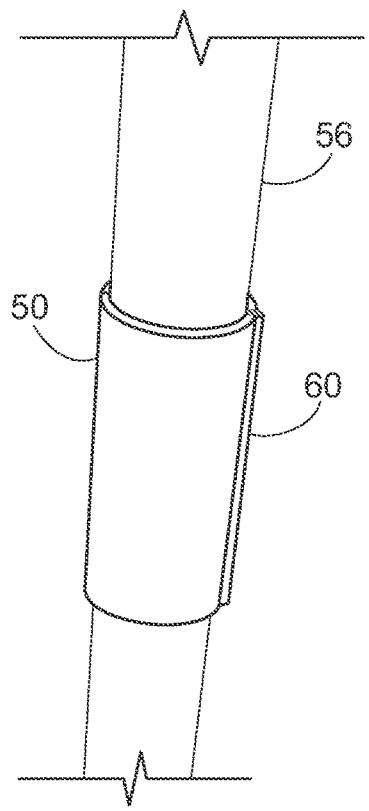
FIG. 3B shows the hinge and clasp clamp housing attached to a golf club.
Figure 5B:
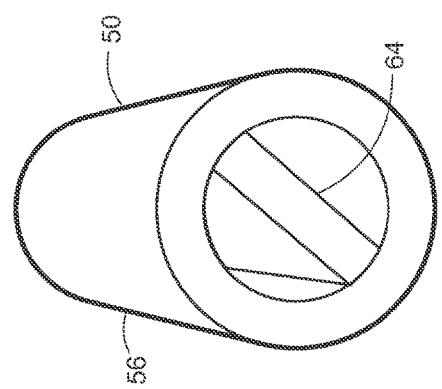
FIG. 5B shows how a hollow club shaft may be used as the housing for holding individual components.
Figure 5A:
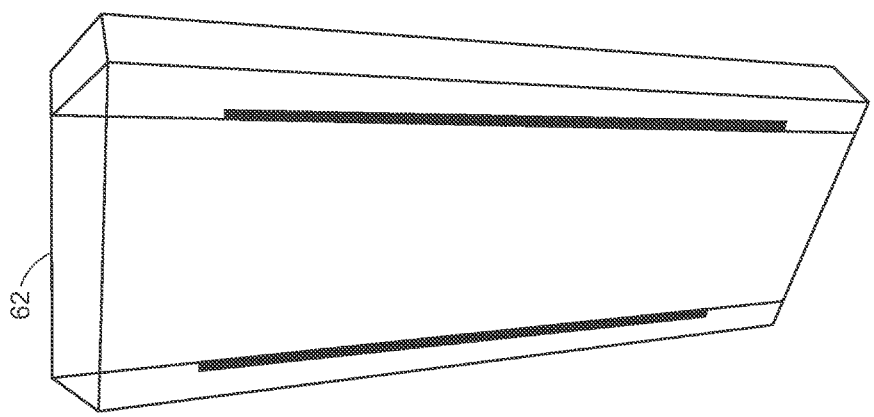
FIG. 5A shows an integrated housing for attaching around a golf club shaft.
Figure 4:
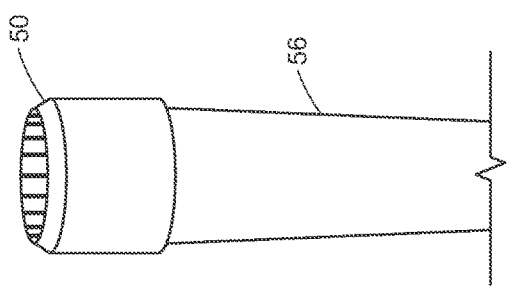
FIG. 4 shows a cap design for attaching the housing to a golf club.

FIG. 3A shows a hinge 58 and clasp clamp design for attaching the housing 50 to a golf club 56. The housing 50 is such that its body rotates around the hinge 58 to wrap around a golf club 56. FIG. 3B shows the hinge 58 and clasp clamp 60 housing 50 attached to a golf club 56. This design is made to attach to the golf club 56 below the grip so that it does not interfere with the golfer's swing. FIG. 4 shows a cap design for attaching the housing 50 to a golf club 56. In this configuration, the device may be placed inside a cap fitting housing 50 at the top of the club grip. As in the housing 50 that attaches below the grip, the device is placed to not impede the golfer's swing. FIG. 5A shows an integrated housing 62 for attaching around a golf club 56 shaft. In this configuration, the individual components of the device may be placed within a specially made grip around the club 56 shaft. FIG. 5B shows how a hollow club 56 shaft may be used as the housing 50 for holding individual components 64.

Figure 6:
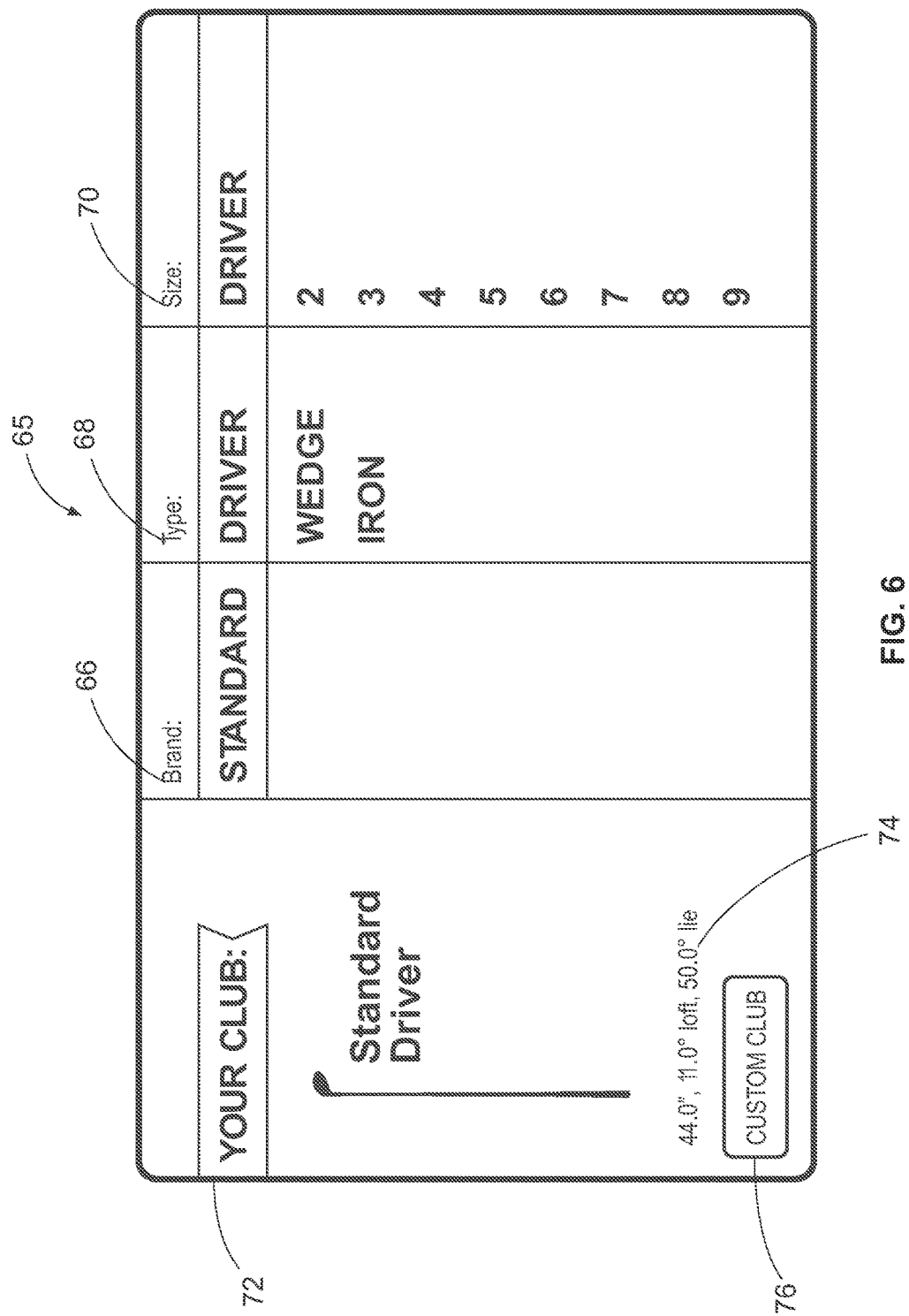
FIG. 6 shows the club selection screen for the application running on a mobile device.

FIG. 6 shows the club selection screen 65 for the application running on a mobile device. On the screen, the club brand 66 is shown and may be a standard club or a custom club. The club type 68 is labeled as a driver, a wedge, or an iron. The club size 70 will be "DRIVER" for a driver, "2" for a pitching wedge, and "3" and above for irons. A user's chosen club 72 appears on the left side of the screen. In the instance shown in FIG. 6, the user has chosen a standard driver. The club information 74, or characteristics of a standard driver, is shown towards the bottom left corner of the screen. The club information 74 is adjusted based on a user's biometrics, such as height and distance from wrist to ground. In this instance, the club is forty-four inches, with an eleven degree loft and a fifty degree lie. To use a customized club, the user may select the customization button 76. Then, the user may adjust characteristics of the club, such as length, loft, and lie.

Figure 7A:
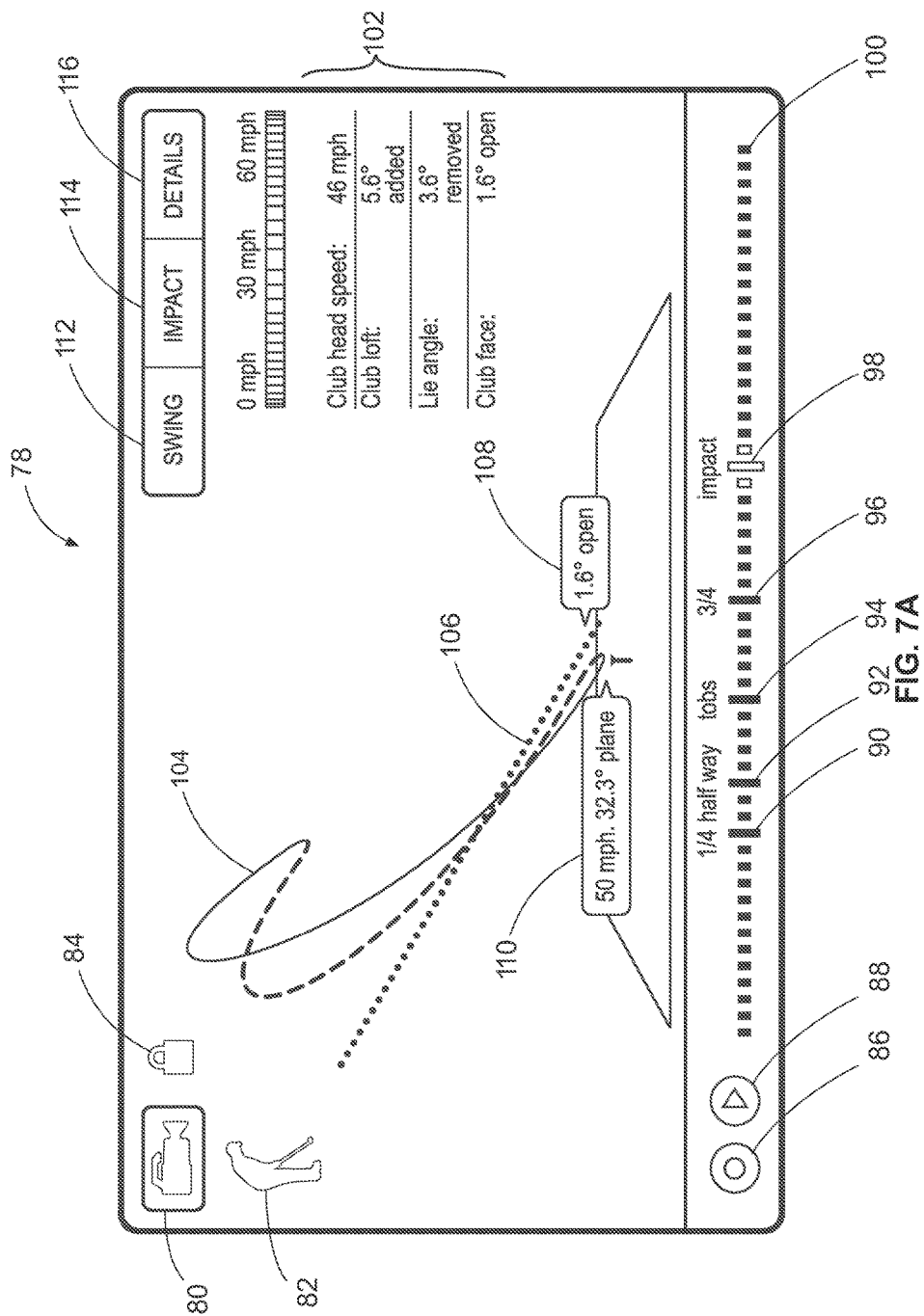
FIG. 7A shows a swing display screen for the application running on a mobile device with the outline of a full swing and summary data.

FIG. 7A shows a swing display screen 78 for the application running on a mobile device with the outline of a full swing and summary data. In general, the interface shown may be controlled with touch screen technology, using a mouse, or using some other input method. The view selector 80 is used to select one of three views, down-the-line, face on, and overhead. The current view of these three is shown by the current view indicator 82. When the locked view indicator 84 is selected, the user may change the view as if rotating a camera. To turn swing recording on and off, the user may select the recording on/off button 86. This controls whether or not the application will accept signals from the device attached to the golf club. If recording is on, then the user may swing a golf club with the device attached to the golf club and select the animation playback button 88 to see an outline of the club trajectory 104 of the swing. Along the bottom of the swing display screen 78, is the club-in-swing position bar 100, which displays the location of the club at all times, including when it crosses important points, such as the ¼ way marker 90, the half-way marker 92, the tobs marker 94, the ¾ way marker 96, and the impact marker 98. For the screen shown in FIG. 7A, the impact marker 98 is lit to show that the club trajectory 104 at impact and related statistics are shown. After impact a club-at-impact snapshot 102 is shown that shows the club speed, the club loft, the lie angle, and how much the club face is open or closed. The club trajectory 104 is shown in the center of the screen and is color-coded by trajectory speed. The club trajectory 104 is shown in conjunction with the club initial orientation 106, the club head orientation 108 at impact, and the club at impact information 110, such as club speed and club plane, so that a user may analyze the quality of the swing. The swing display screen 78 in FIG. 7A further shows that the swing display screen was selected with the swing detail button 112. For impact detail in the form of graphics and statistics, the user may select the impact detail button 114, and to see further details, the user may select the parameter detail button 116 and see further statistics, such as the speedpoint, plane angle, club face to plane angle, and club face to horizon angle, among other parameters defined above.

In order to zoom and shrink so that the user may see the club trajectory 104 and other statistics at any magnification, the user may "pinch" or "pan" the screen if it is a touch screen. The user may also increase or decrease the playback speed by moving his or her hand along the club-in-swing position bar 100 on the touch screen at whatever speed the user desires. The club-in-swing position bar 100, or progress bar, also functions as a scroll bar. A user may place a finger at any point along the bar to position the club at that point in the playback. Dragging a finger along the bar continuously repositions the club to the new playback position, allowing one to animate the club over a specific range at a specific speed.

Figure 7B:
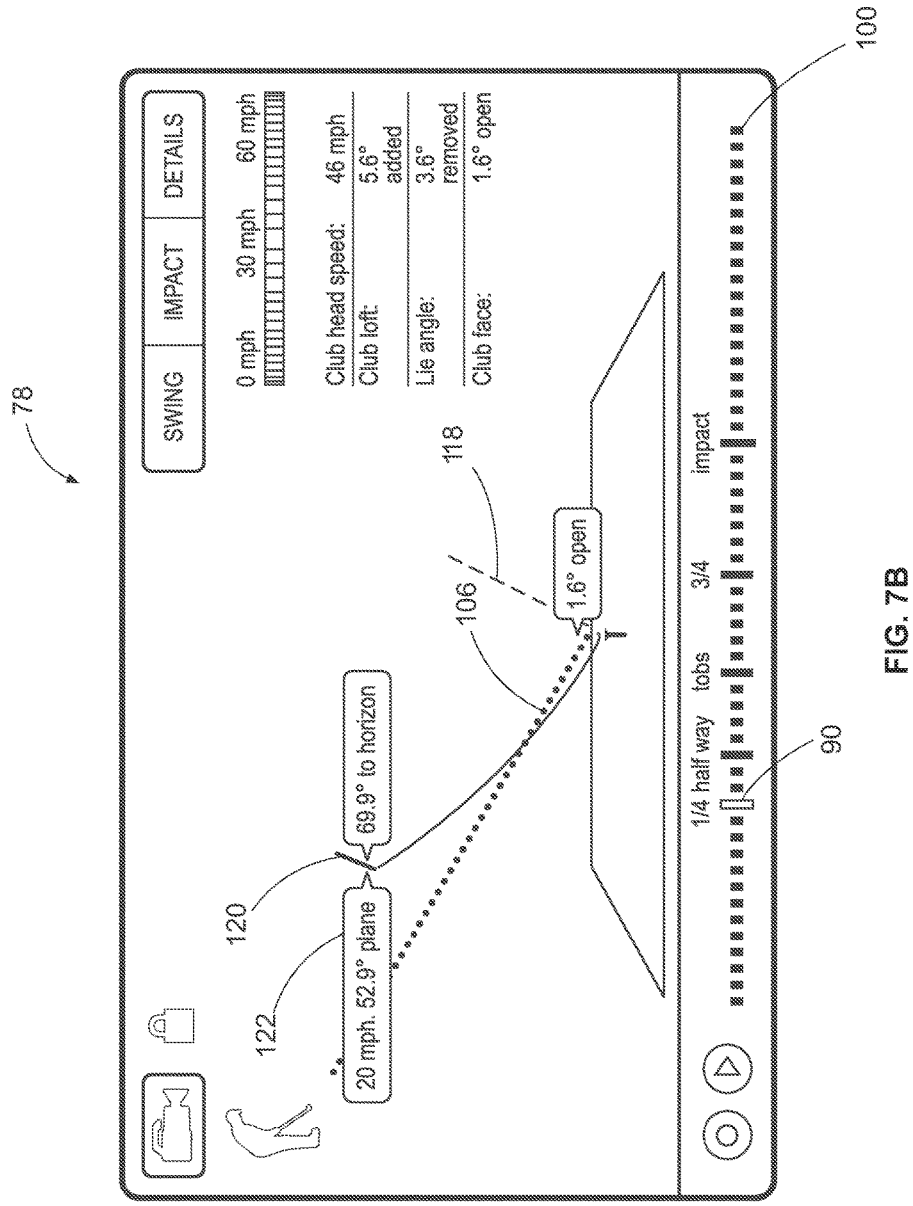
FIG. 7B shows a swing display screen for the application running on a mobile device with statistics at ¼ the way point through a swing.
Figure 7C:
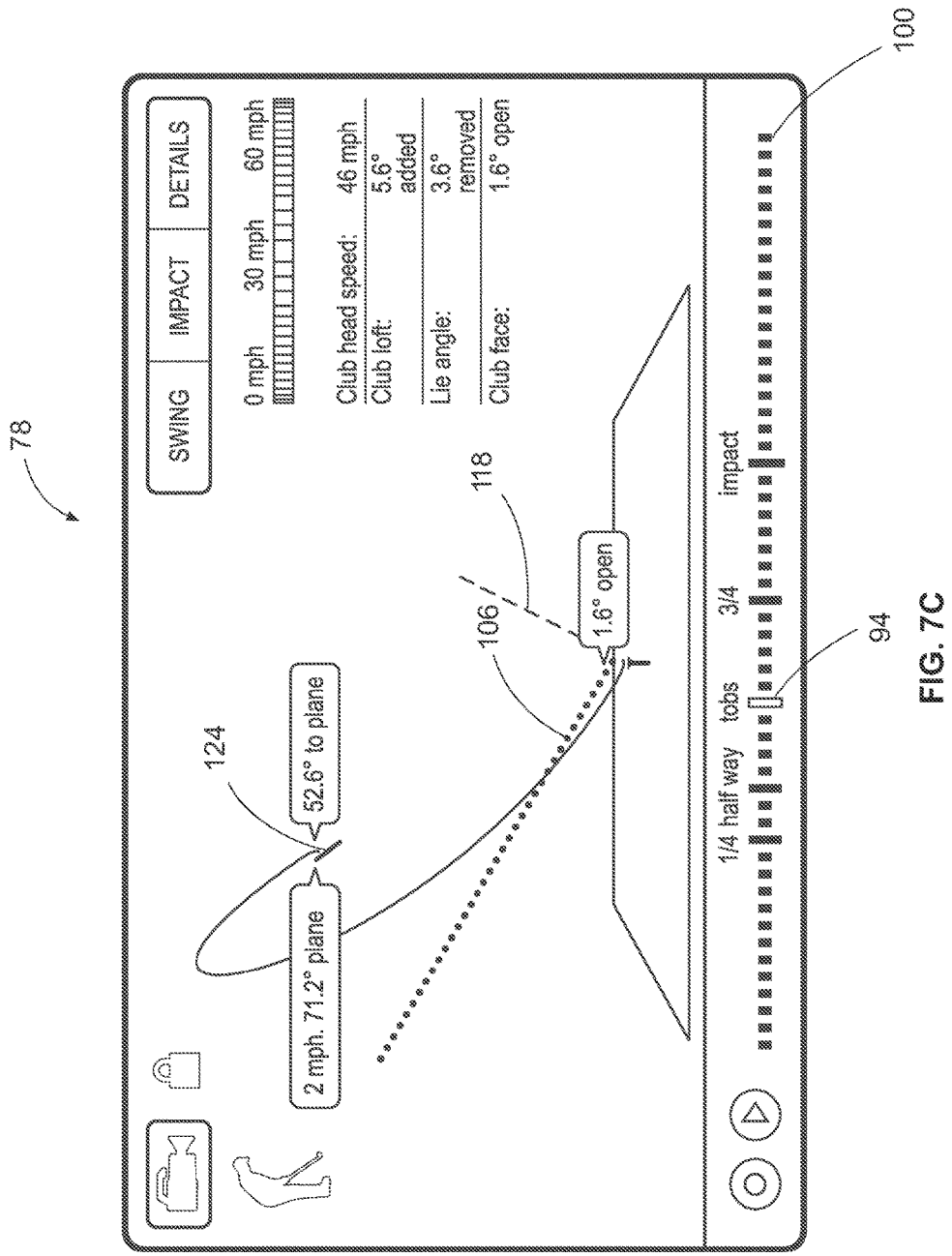
FIG. 7C shows a swing display screen for the application running on a mobile device with statistics at the top of a back swing.
Figure 7D:
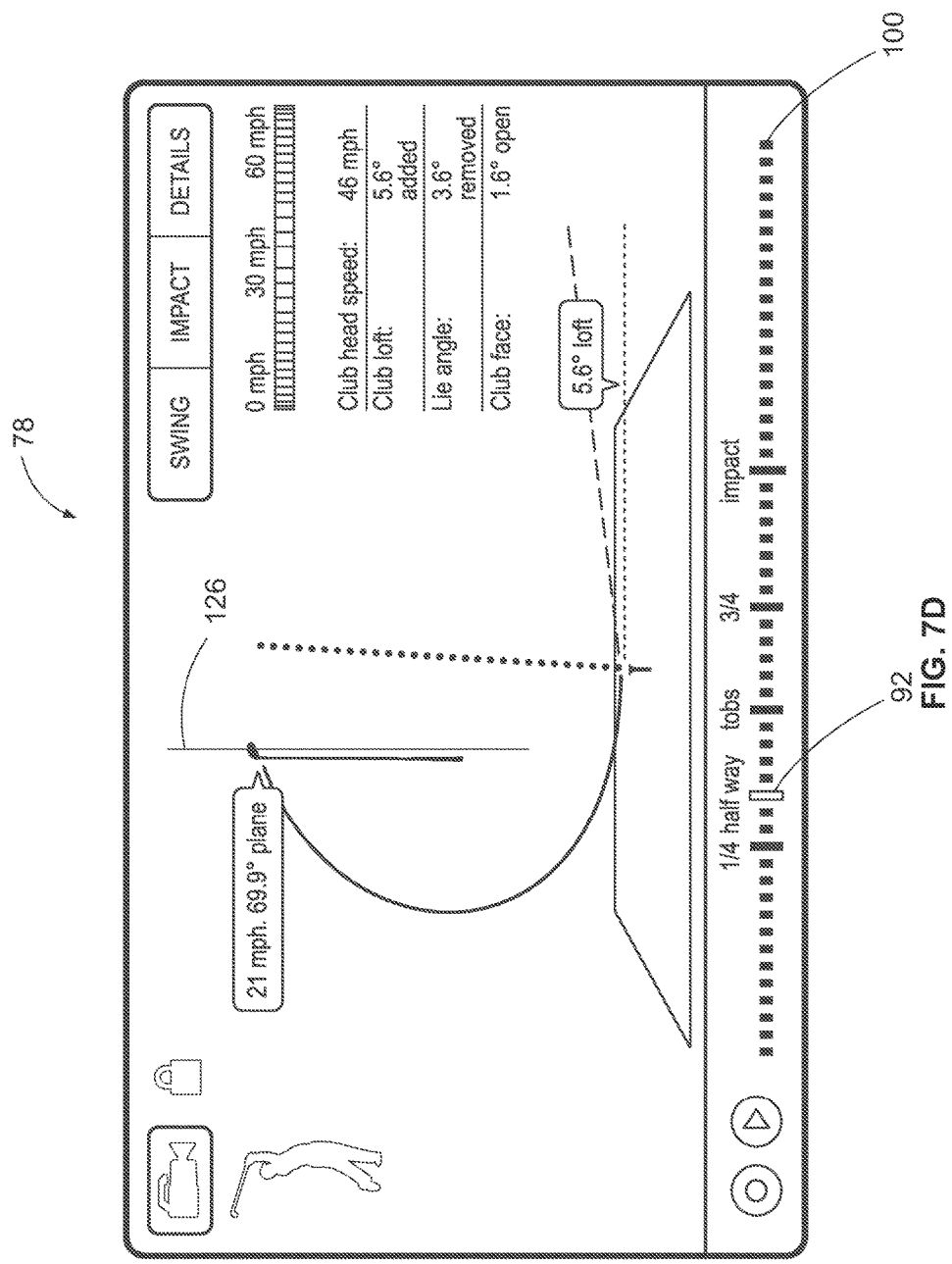
FIG. 7D shows a swing display screen for the application running on a mobile device with statistics at half-way point of a swing.

FIG. 7B shows a swing display screen 78 for the application running on a mobile device with statistics at the ¼ way point through a swing. The club-in-swing position bar 100 is lit up to the ¼ way marker 90. The ball launch direction 118 is shown for comparison along with the angle of the club face to the horizon 120 and other club at point information 122, such as club speed and club plane at a particular point. FIG. 7C shows a swing display screen 78 for the application running on a mobile device with statistics at the top of a back swing. The club-in-swing position bar 100 is lit up to the tobs marker 94. Along with other statistics previously described, the angle of club face to initial plane 124 is shown for comparison with the club initial orientation 106 and the ball launch direction 118. The user may analyze this data and make proper adjustments to improve his or her swing. FIG. 7D shows a swing display screen 78 for the application running on a mobile device with statistics at the half-way point of a swing. The club-in-swing position bar 100 is lit up to the half-way marker 92. As with earlier described screens, relevant statistics are shown for comparison and analysis. A user may use a finger or other input device to draw a free-hand line 126 across areas of the swing display screen 78 to mark characteristics of a desired swing and later compare the free-hand line 126 with the actual swing.

Figure 8:
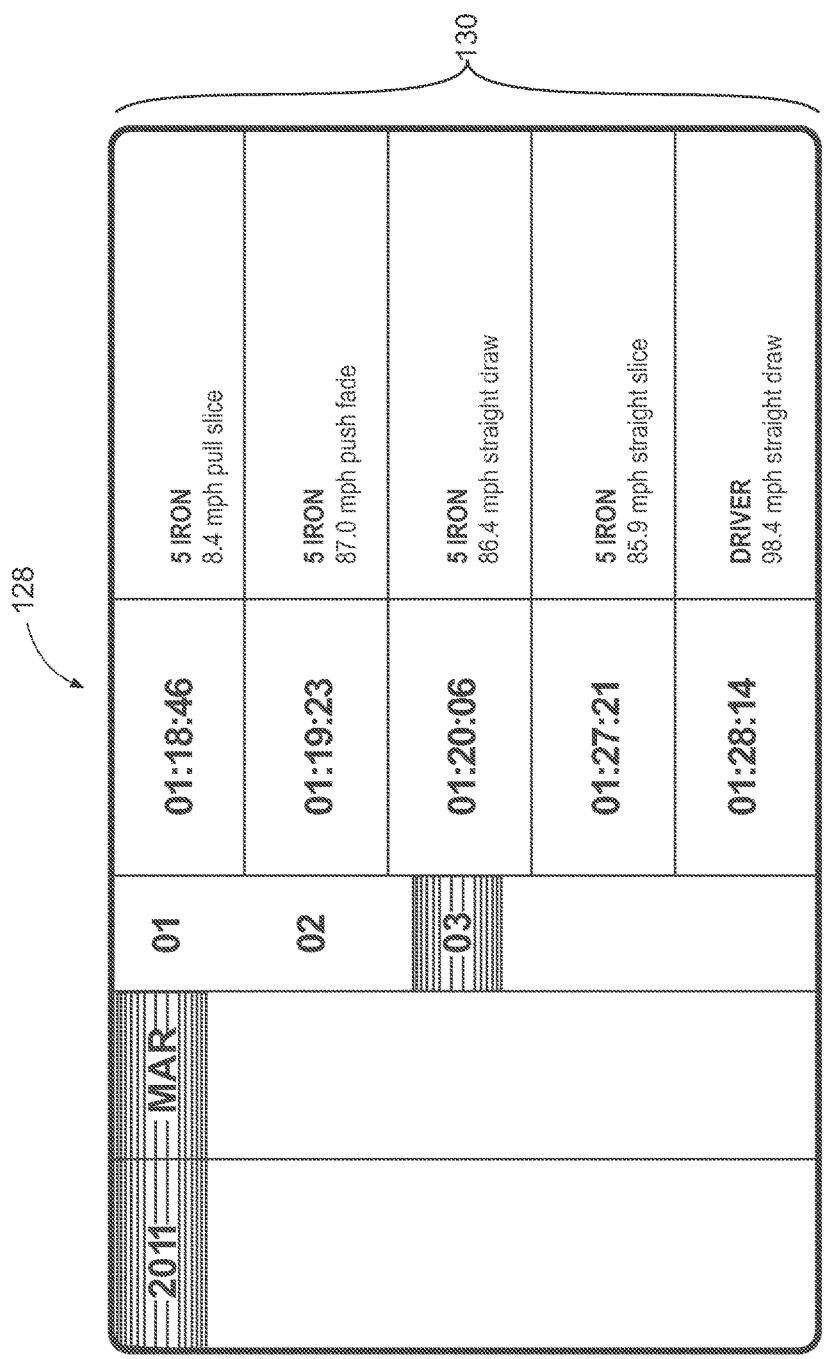
FIG. 8 shows a swing selection screen with a table of swing descriptions for a period of time.

FIG. 8 shows a swing selection screen 128 with a table of swing descriptions for a period of time. The swing selection screen 128 allows a user to view daily swing information 130 by selecting a particular date. The information shown are swing descriptions based on launch angles. Other combinations of data may be displayed.

Figure 9:
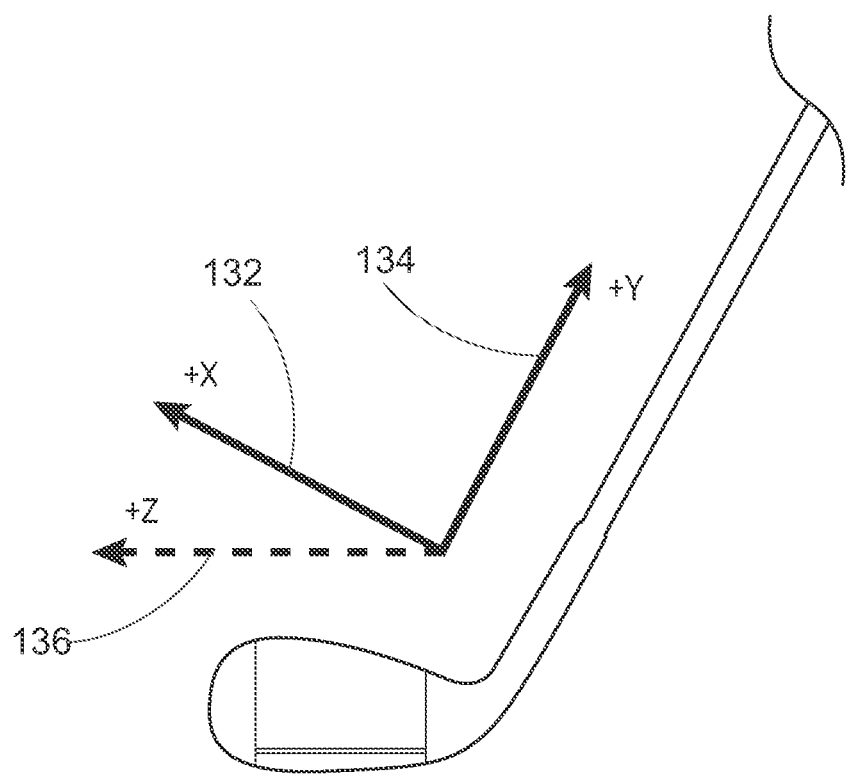
FIG. 9 shows the coordinate system used to describe the algorithm for the principles of operation.

FIG. 9 shows the coordinate system used to describe the algorithm for the following principles of operation. Using the earth as a reference point, the x-axis 132 and the z-axis 136 define the plane along the "ground". The y-axis 134 is straight out of or perpendicular to the "ground". The face-on view is the y-z plane. The down-the-line view is the x-y plane, and the overhead view is the x-z plane.

The following paragraphs describe the algorithm for the principles of operation.

A fixed right-orthogonal coordinate system $0X_g Y_g Z_g$ is selected, located at the starting position of the object. $0Y_g$ is directed at the zenith. Axes $0X_g$ and $0Z_g$ are horizontal, with $0X_g$ having an arbitrary position within the horizontal plane. A right coordinate system is associated with the object, the axes of which coincide with the fixed coordinate system in the initial position. The angular position of the object in the fixed coordinate system is determined by Euler angles $\alpha$, $\beta$ and $\gamma$, with transitions defined from the fixed coordinate system axes.

The relationship between the angular velocities of the object's orientation and angular velocities of the object's rotation in the associated axes is defined by $$\dot{\beta} = \omega_y \sin\gamma + \omega_z \cos\gamma;$$

$$\dot{\alpha} = \frac{1}{\cos\beta}(\omega_y \cos\gamma - \omega_z \sin\gamma);$$

$$\dot{\gamma} = \omega_x - tg\beta(\omega_y \cos\gamma - \omega_z \sin\gamma).$$

Integration of these non-linear equations theoretically allows one to obtain the angles of orientation. However, this is impractical in light of the following calculations, and at the angle $\beta=90°$ ($\cos \beta=0$). In light of this, inertial navigation uses different methods to describe the orientation of the object. Description is most frequently accomplished using direction cosines.

With the unit vectors placed along axes of the fixed and associated coordinate systems with the same identifiers, the transition from the fixed coordinate system to the associated one is defined by the transformation $[x,y,z]^T = P[x_g, y_g, z_g]^T$, where P is a matrix of direction cosines $$P = \begin{vmatrix} P_{11} & P_{12} & P_{13} \\ P_{21} & P_{22} & P_{23} \\ P_{31} & P_{32} & P_{33} \end{vmatrix}$$

The elements of this matrix will then have the following structure:

$P_{11}=\cos \alpha \cos \beta$; $P_{21}=\sin \alpha \sin \gamma - \cos \alpha \sin \beta \cos \gamma$;

$P_{12}=\sin \beta$; $P_{22}=\cos \beta \cos \gamma$;

$P_{13}=-\sin \alpha \cos \beta$; $P_{23}=\cos \alpha \sin \gamma + \cos \gamma \sin \alpha \sin \beta$;

$P_{31}=\cos \gamma \sin \alpha 30 \sin \beta \sin \gamma \cos \alpha$;

$P_{32}=-\sin \gamma \cos \beta$;

$P_{33}=\cos \alpha \cos \gamma - \sin \alpha \sin \beta \sin \gamma$.

To obtain the current values of the matrix elements, we integrate Poisson's equation $\dot{P}=[\omega]P$, where $[\omega]$, the rotational matrix, is $$[\omega] = \begin{vmatrix} 0 & \omega_z & -\omega_y \\ -\omega_z & 0 & \omega_x \\ \omega_y & -\omega_x & 0 \end{vmatrix}$$

where $\omega_x$, $\omega_y$, $\omega_z$ are angular velocities of the rotation of the object in the associated axes. The matrix elements found through integration are used to compute the current values of the angles of orientation using $$\beta = arctg z \frac{P_{12}}{\sqrt{P_{22}^2 + P_{32}^2}};$$

$$\alpha = arctg z \frac{-P_{32}}{P_{22}};$$

$$\gamma = arctg z \frac{-P_{13}}{P_{11}}.$$

To obtain these formulae, one must use the structure of the matrix of direction cosines. The initial conditions for integrating Poisson's equation are determined during the initialization phase (initial calibration) of the inertial module.

The determination of parameters of the trajectory (linear velocities and coordinates) is done by integrating components of the relative acceleration vector in the fixed coordinate system:

$$[V_x V_y V_z]^T = \int_0^T W_g dt + [V_{x0} V_{y0} V_{z0}]^T;$$

$$[x_g y_g z_g]^T = \int_0^T [V_x V_y V_z]^T dt + [x_{g0} y_{g0} z_{g0}]^T.$$

The calculation of the components of the vector of relative acceleration is done according to $W_g = P^T W - [g]$, where W is the vector of apparent acceleration, the components of which are measured by the accelerometers of the inertial module, and [g] is acceleration due to gravity at the point of the current location of the module on the earth's surface, with components $g_x=0$; $g_y=g$; $g_z=0$;

Computing the acceleration due to gravity is done through $$g=g_1(1+\beta \sin^2\varphi+\beta_1 \sin^2\varphi),$$

where $\varphi$ is the geographic (geodesic) latitude of the location of the object:

$$\beta=0.0053172; \beta_1=0.0000071; g_1=9,78049 \text{ m/s}^2$$

The initialization procedure is done with the module immobilized in the initial position. The goal of the procedure is an estimate of the 0 values and trends of the gyroscopes, and also the elements of the matrix of direction cosines determining the initial orientation of the object. The first problem, the error values of the gyroscopes, is presented as $\Delta\omega=\Delta\omega_0+\chi t+n(t)$, where $\Delta\omega_0$ is the shift of the 0-value, $\chi$ is the speed of the trend, and $n(t)$ is the noise of the sensor. The estimate of parameters $\Delta\omega_0$ and $\chi$ is done through a method of least-squares applied to a recorded set of measurements of gyroscope values during the period of initialization. Three elements of the matrix of direction cosines of the initial orientation of the object are determined by solving the algebraic equation $W=PW_g'$, where $W_g'=[0 \ g \ 0]^T$ is the vector of the apparent acceleration of the object in the immobilized system of coordinates during initialization. From this, $$P_{12}(0) = \frac{\overline{W}_x(0)}{g}; P_{22}(0) = \frac{\overline{W}_y(0)}{g}; P_{22}(0) = \frac{\overline{W}_z(0)}{g},$$

where $\overline{W}_x(0)$, $\overline{W}_y(0)$, $\overline{W}_z(0)$ are the average values of the apparent accelerations of the object during the period of initialization. The formulae for determining the remaining elements of direction cosines are found from equations determining its structure given that $\alpha=0$.

Some additional considerations are that the system relies heavily on noise filtering algorithms to improve the device's accuracy over time. Additional correction is performed by assuming that the starting point of the club face is at the location of the ball, and that the club passes through that point again on the down-swing. The precise time that the club is passing through this location is determined by locating a shock value in the accelerometer data. The trajectory of the club is then corrected based on this information, reducing the error by more than 50%.

Error correction may also be accomplished two additional ways. First, camera-augmented, six degrees of freedom (6-DOF) club motion capture, calibration and analysis may be used to correct error introduced from assuming that the starting point of the club face is at the location of the ball, and that the club passes through that point again on the down-swing. All measurements referenced are made with an image recognition algorithm. Referring back to FIG. 2A, FIG. 2B and FIG. 2C, a camera 51 is built into the bottom of the apparatus, pointing down the golf club 56 shaft and at the club head. The camera 51 is used to measure the distance between the golf ball and the golf club 56 head at address. This information is then used to improve error correction of the swing trajectory over a system that assumes that the golf ball, and thus the point of impact, is exactly at the point of address. If the user addresses a few inches behind the golf ball, this diminishes the usefulness of the current algorithm. However, the camera can detect how far the ball is relative to the club face and compensate for this distance using the algorithm, thus removing the limitation created by assuming that the point of impact is the same as the point of address. The camera 51 may also be used to note the orientation of the apparatus relative to the golf club 56 face. This removes the need to precisely position the apparatus on the golf club 56. The camera 51 will also measure club head deflection throughout the swing, removing the need to extrapolate such information. Since the golf club 56 head moves slowly relative to the golf club 56 shaft, no more than ten miles per hour at the maximum, a 30 fps camera is sufficient to capture the motion. The camera 51 may also be used to see what part of the golf club 56 makes contact with the ball, requiring a higher shutter speed.

The camera 51 will work in one of two modes. It will either capture and analyze data directly on the device, or it will send a live stream to the mobile device via Bluetooth or some other protocol to offload processing. Since the Bluetooth link has limited bandwidth, sending the live stream may be governed by the onboard accelerometer. When according to the accelerometer the golf club 56 is stationary, no data will be sent. When motion starts, then data is sent from that point until the point of impact.

The data produced will be used for two things. First, it will track the rotation of apparatus on the golf club 56 shaft relative to golf club 56 face. This is done by contour mapping the image and then locating the leading edge. Once the leading edge is located, the leading edge information is combined with the club lie information, corrected for the amount of distortion that would be introduced to the camera 51 and used to measure the angle of the leading edge of the golf club 56 head face.

In order to determine the angle of rotation between two images of similar objects, such as the golf club 56 head face at various points throughout a golf club 56 swing, gradient histograms are compared. The gradient of a rasterized image at a point is a vector, defining the direction and magnitude of the maximum change of its value. For an image, the underlying "value" is the color value at a point. This is analogous to the gradient of a function of two variables. A large value of the modulo of the gradient at a point is often an indication that the point is on a boundary of some shape.

Figure 10A:
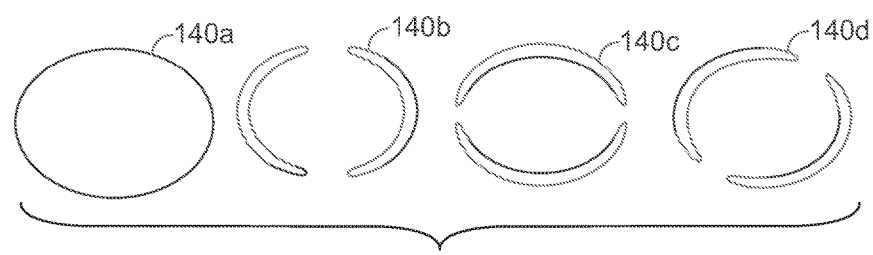
FIG. 10A shows an arbitrary shape that is first gradient mapped and then rotated by 45 degrees.

In the ideal case, a gradient function is completely defined through its partial derivatives. In the case of images, partial derivatives obtained, for example, using the Sobel or Shaar operator define the gradient very roughly. As a result, one may calculate the gradient at a point through directional derivatives. The direction in which the derivative obtains its maximum value will be the direction of the gradient. The value will be the modulo of the gradient. Sobel and Shaar operators allow one to calculate the derivative of an image in two directions, horizontal and vertical. To calculate the derivative in a different direction, we can simply rotate the image by the necessary angle and use one of these operators as shown in FIG. 10A. FIG. 10A shows an arbitrary shape that is first gradient mapped and then rotated by 45 degrees. In FIG. 10A, the first image 140a shows an arbitrary shape detected by the camera. The second and third images 140b and 140c show the images gradient mapped. The fourth image 140d shows the gradient mapped images rotated by 45 degrees.

Because it would be too cumbersome to compute derivatives in all directions, one may rely on preset accuracy requirements. If one needs accuracy to 1 degree, one must compute 180 derivatives. If one needs accuracy to 15 degrees, then one only needs 12 derivatives. Therefore, at every point of the image, one has a set of derivative values in the various directions. Using this set of derivatives, one may deduce whether a given point is on the border of some curve or not with the curve potentially being the edge of some shape or object. There may be a large number of ways to set the criteria for edge detection. In the described embodiment, the simplest method is used, although other methods may also be used. If there are two orthogonal directions, one of which has a very small derivative value and the other a very large, then the point in question is a boundary point and the tangent to this edge has the direction of the smaller derivative.

Figure 10B:
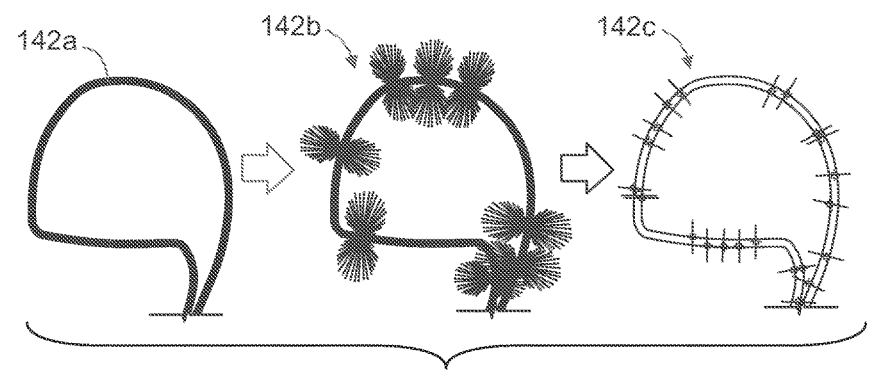
FIG. 10B shows an illustration of an outline of a golf club head with the boundaries located and the direction of the gradients calculated.

In the described embodiment, one must detect shapes and their boundaries. Therefore, one must start by selecting all the boundary points of interest with the minimal contrast level defining a boundary being modified by the overall contrast of the image. If the overall brightness of the image is too low, the contrast threshold must be adjusted. That is, the color difference between two points considered a boundary must be adjusted. FIG. 10B shows an illustration of an outline of a golf club head with the boundaries located and the direction of the gradients calculated. For every point, one has the direction of its gradient, and the modulo value is no longer needed. Image 142a shows an illustration of the outline of a golf club head. Using the described algorithm, each point is in the set of boundary points is located as illustrated in image 142b. Next, the direction of the gradients is computed as shown in image 142c.

Figure 10C:
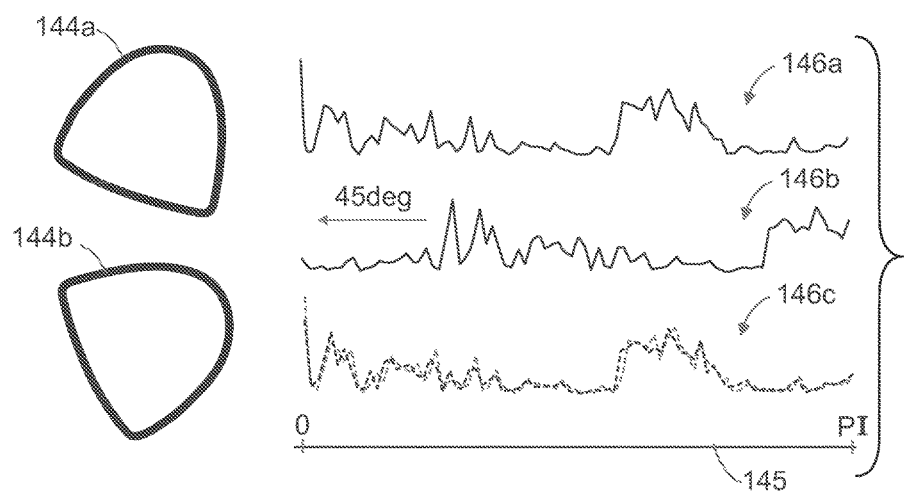
FIG. 10C shows a histogram of gradients on a golf club head.

Next, one must construct the histogram of these directions. The idea is that a rotation of the object on an image by some angle leads to the histogram of gradients shifting cyclically. This is true if the image contains nothing but the target object. It is helpful to remember that histograms of gradients are periodic functions, such that a and α+180 are equivalent. Therefore, subsequent analysis and transformations of the histogram should account for this cyclical nature. It is also worth noting that histograms are invariant with respect to the size of the image. Multiple ways to compare histograms may be used. In the described embodiment, a simple convolution is used. The point at which the convolution takes on its largest value is the phase shift at which the two histograms are maximally similar. FIG. 10C shows a histogram of gradients on a golf club head. The primary image of a golf club head 144a is shown with its corresponding first histogram 146a in an initial orientation. The secondary image of a golf club head 144b is shown in an orientation rotated 45 degrees with its corresponding second histogram 146b. The third histogram 146c shows the first histogram 146a and the second histogram 146b overlaid to show the shift and the similarity of the histograms. The horizontal axis 145 in FIG. 10C shows the histogram measured in radians.

Figures 11A, 11B:
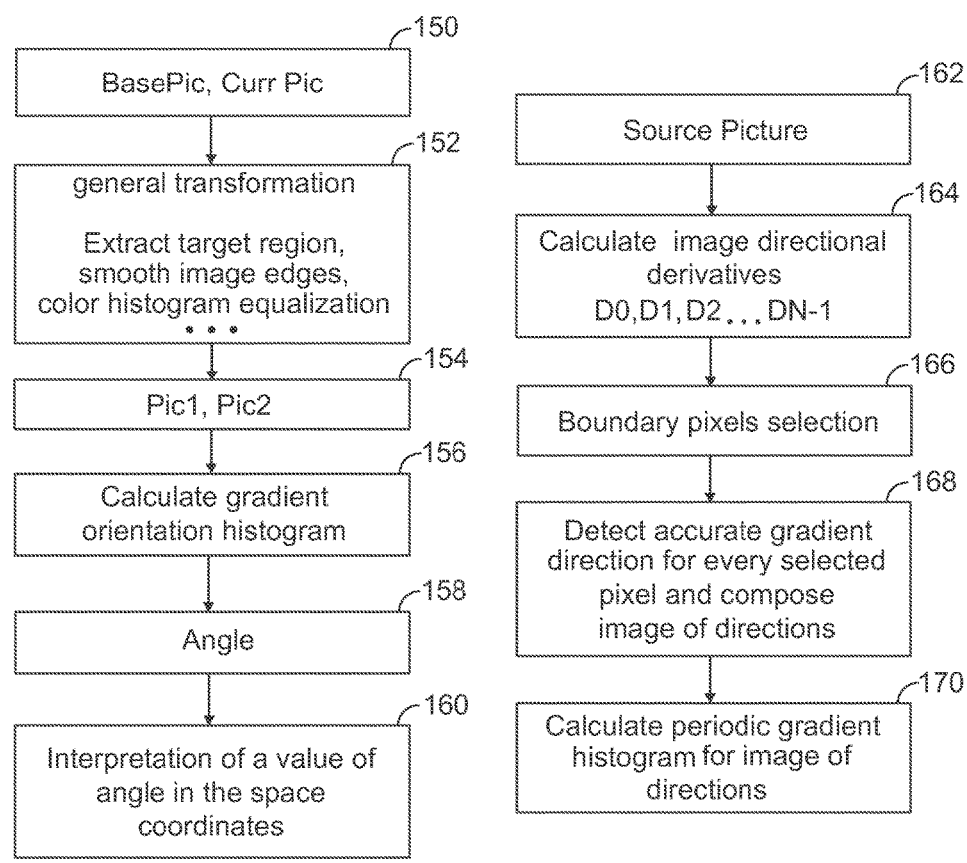
FIG. 11A shows a flow chart of the process of computing gradients in all directions and determining the relative rotation of the image.
FIG. 11B shows a flow chart of the process for calculating a gradient orientation histogram.

FIG. 11A shows a flow chart of the process of computing gradients in all directions and determining the relative rotation of the image. Step 150 shows the starting variables, where the variables BasePic and CurrPic are the base image and the current image. The process in step 150 starts by comparing the current image with a base image that was recorded at an earlier time. Step 152 shows a general transformation wherein the target region of an image is extracted, the image edges are smoothed and color histogram equalization is performed to provide a clean image. In step 154, Pic1 and Pic 2 are the variables output from the process in step 152 and represent the clean images corresponding to the variables BasePic and CurrPic from step 150, respectively. Then, the gradient orientation histogram is calculated in all directions in step 156 to determine the relative rotation of the images. In step 158, the angle measuring the relative rotation of the images is output. In step 160, the value of the angle in the space coordinates is interpreted. In other words, step 160 adjusts the output angle for visual distortions created from varying club lie angles.

FIG. 11B shows a flow chart of the process for calculating a gradient orientation histogram that is represented in step 156 of FIG. 11A. In step 162, the source picture is the image supplied for analysis. In step 164, the image directional derivatives are calculated in all directions. In an exemplary embodiment, 180 derivatives are calculated to achieve precision of 1°. In step 166, the boundary pixels of the golf club head are selected to determine the boundaries based on the calculated directional derivatives. In step 168, the accurate gradient direction for every selected pixel is detected and an image of directions is composed. Finally, in step 170, a periodic gradient orientation histogram is calculated for the accurate gradient direction for every selected pixel detected in step 168.

The second method of error correction in the described embodiments uses navigation data to track the position of the golf club throughout the swing. One of the main problems with motion tracking using accelerometer and gyroscope data is that the position data has to be retrieved by integrating the accelerometer data twice, which generates error that grows quadratically as a function of time. This means that drift accumulates over time, and position data beyond a few seconds of capture are inaccurate. For the first few seconds, however, such data are quite accurate. Conversely, ultrasound positioning systems like the MIT Cricket system are stable over time, but imprecise with measurements that are less than or equal to a few centimeters. The described embodiment uses accelerometer data and gyroscope data and corrects for drift using the ultrasound positioning system approach.

Using the ultrasound positioning system approach, three or more portable base stations that emit an ultrasonic pulse and an RF pulse simultaneously are arbitrarily placed at different (x,y,z) coordinates relative to the receiver so that they are arranged in three-dimensional space relative to a horizontal plane, that is, at different distances and heights. The base stations go through a startup procedure wherein they communicate via RF to determine relative placement, and each base station emits an ultrasonic pulse while the others listen. All base stations that are aware of each other will then go through a triangulation process to determine their relative positions. Each base station uses the amount of time it took to hear the pulse from the other base stations to determine the distance from the other base stations. This data is used to build a general coordinate system, which is sent to the apparatus attached to the golf club.

Once calibrated, the base stations emit an RF and ultrasonic pulse at the same time. Each one will do this on slightly different frequencies so that the receiving party can tell which base station is transmitting. The apparatus will be equipped with the appropriate RF and ultrasonic receiver and will be able to determine its distance from all the portable base stations without having to expend energy to broadcast its own position. This position data can then be used together with the motion data produced by the accelerometer and gyroscope to measure real-time position and motion more accurately.

The apparatus will have a full 6 DOF capability based on the accelerometer and the gyroscope. The algorithm for computing position and orientation will use the accelerometer and gyroscope information and will incorporate the ultrasonic pulses to correct for drift in the manner described in "Low Cost Inertial Navigation: Learning to Integrate Noise and Find Your Way" by Kevin J. Walchko, Thesis Presented to the Graduate School of the University of Florida in Partial Fulfillment of the Requirements for the Degree of Master of Science, University of Florida, 2002, which uses GPS data to correct accelerometer and gyroscope data rather than ultrasound data.

Figure 12:
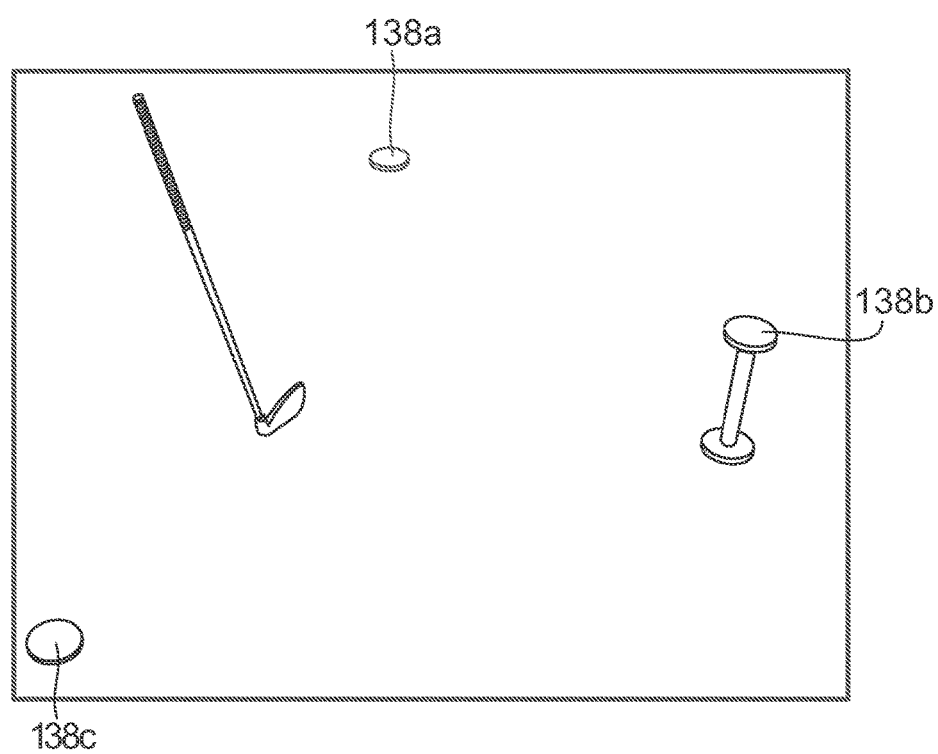
FIG. 12 shows a perspective view of a multiplicity of ultrasonic and RF base stations used to correct accelerometer integration drift.

FIG. 12 shows a perspective view of a multiplicity of ultrasonic and RF base stations used to correct for accelerometer integration drift. A multiplicity of base stations 138a-138c are arranged in three-dimensional space relative to a horizontal plane. Each base station 138a-138c includes an ultrasonic transmitter that transmits an ultrasonic pulse at a frequency different than the frequency transmitted by any of the other ultrasonic transmitters in the other base stations 138a-138c. Each base station 138a-138c also includes a radio transmitter that transmits a radio frequency pulse. An ultrasonic receiver and a radio receiver are also used in the base stations 138a-138c with a triangulation process to determine the relative positions of the multiplicity of base stations and to build a general coordinate system, which is transmitted to the apparatus. A periodic pulse generator periodically transmits an ultrasonic pulse using the ultrasonic transmitter and a radio frequency pulse using the first radio transmitter so that the apparatus can track the golf club motion throughout the coordinate system.

Figure 13A:
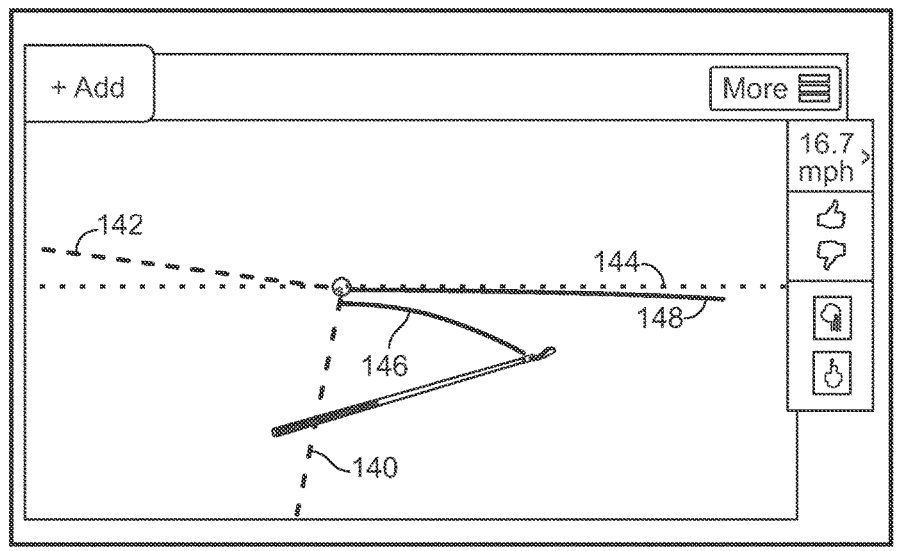
FIG. 13A shows initial orientation lines, lines showing the start of a backswing, and laser lines showing the start of a backswing.
Figure 13B:
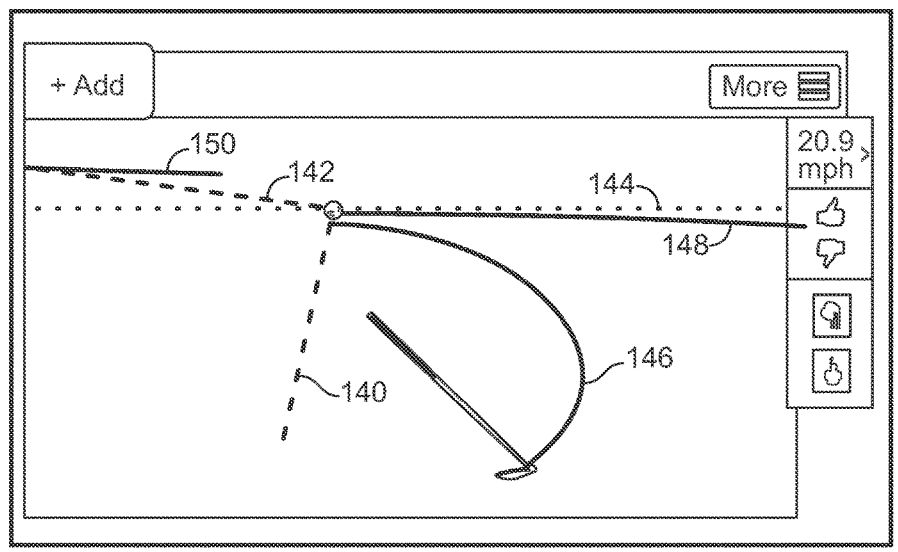
FIG. 13B shows initial orientation lines, lines showing most of a backswing, and laser lines showing a backswing while simulating laser lines from both the bottom and the top of the club shaft during the golf club swing.

Other graphics that may be useful to analyze a golfer's swing are laser lines. Laser lines are a way to visualize how a golfer's swing plane changes throughout the swing. Given a fixed, flat virtual playing surface, laser lines are the intersection of an infinite segment in which the club lies and the plane of the playing surface. In other words, if the club had a laser emitter in both ends, laser lines would capture the pattern the laser would draw on the ground during a swing. FIG. 13A shows initial orientation lines, lines showing the start of a backswing, and laser lines showing the start of a backswing. The club shaft at address 140, the club face direction 142 and the target line 144 are all shown to depict the player's initial approach when lining up for a shot. The outline of the backswing 146 shows that the player has taken a fraction of a backswing. The club head laser line from the backswing 148 is shown as if a laser light shone from the bottom of the club shaft and drew a line on the ground. FIG. 13B shows initial orientation lines, lines showing most of a backswing, and laser lines showing a backswing while simulating laser lines from both the bottom and the top of the club shaft during the golf club swing. Again, the club shaft at address 140, the club face direction 142 and the target line 144 are all shown to depict the player's initial approach when lining up for a shot. The outline of the backswing 146 shows that the player has taken more of a backswing than that shown in FIG. 13A. The backswing shown in FIG. 13B shows how the club head laser line from the backswing 148 is drawn to a point where the bottom of the club shaft no longer points toward the ground. Shortly thereafter, the top of the golf club points toward the ground and the club tail laser line from the backswing 150 appears.

Figure 14:
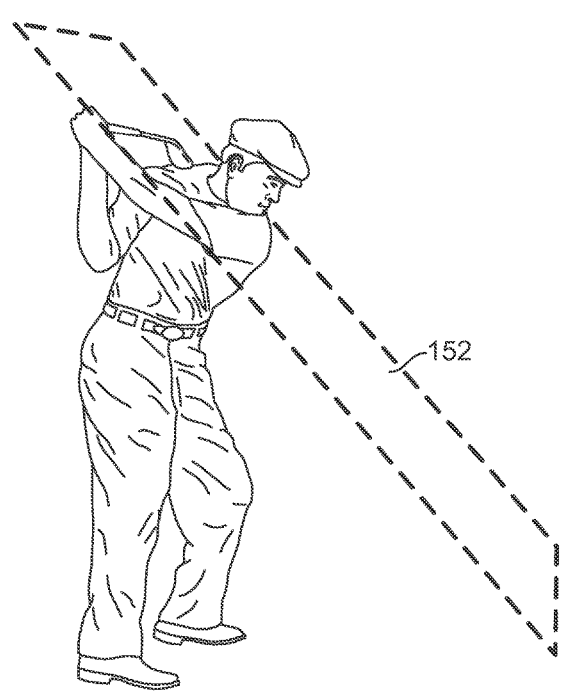
FIG. 14 shows a swing plane measured during a player's swing.

A golf swing plane is the plane in which the club travels throughout the swing. Mathematically, if the club shaft at time t is taken as vector $v_t$, and $v_{t1}$ at time t1 immediately subsequent to time t, then the vector normal to the swing plane is defined as the cross product $v_t \times v_{t1}$. Because this definition is time-dependent, it follows that the plane is something that changes throughout the swing. FIG. 14 shows a swing plane 152 measured during a player's swing. Swing plane 152 is a popular golf teaching concept, typically visualized as a literal pane of glass as shown in FIG. 14. A swing plane 152 is useful for two separate concepts, 1) efficiency of power delivery, and 2) spin imparted at impact. The direction of travel of the club, relative to the clubface, and the ball determine the amount of clockwise, or counter-clockwise spin imparted on the ball. The variability in the swing plane 152 throughout the swing relates to how much energy the golfer focuses on accelerating the club and how much energy is lost from rotating the club about an axis other than the normal vector of the initial plane. Laser lines are a visual representation of both of these elements.

Figure 15:
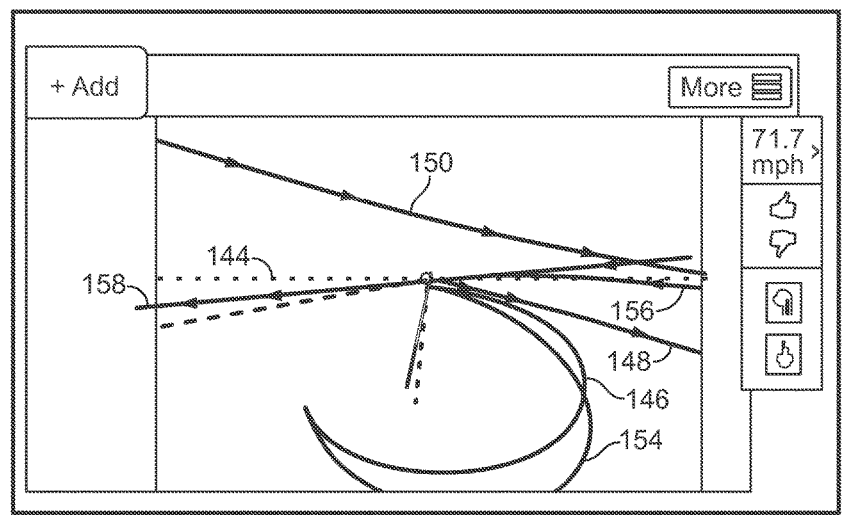
FIG. 15 shows a swing display screen with the outline of a full swing and laser lines drawn from the head of the club and the tail of the club during the full swing.

FIG. 15 shows a swing display screen with the outline of a full swing and laser lines drawn from the head of the club and the tail of the club during the full swing. This figure shows the swing capture of an average golfer viewed from above. The outline of the backswing 146 and the outline of the forward swing 154 show the movement of the golf club head throughout the swing. The club head laser line from the backswing 148 and the club tail laser line from the backswing 150 display lines that a laser would draw on the ground from the head and the tail of the shaft of the golf club during a backswing. The club head laser line from the forward swing 156 and the club tail laser line from the forward swing 158 display lines that a laser would draw on the ground from the head and the tail of the shaft of the golf club during a forward swing. This figure shows that the plane orientation was significantly inside the dotted target line 144 on takeaway, was redirected at the beginning on the down swing with the club tail laser line from the forward swing 158 starting on the outside of the target line 144, and was redirected again toward the end. The substantial variability in the orientation of the plane lines means that this is a very inefficient swing. Further, because the club face direction is not parallel to the club head laser line from the forward swing 156, the ball will start with a counter-clockwise spin, and will curve to the left of its starting direction. A more professional swing has lines that are closer together, and much straighter.

Figure 16A:
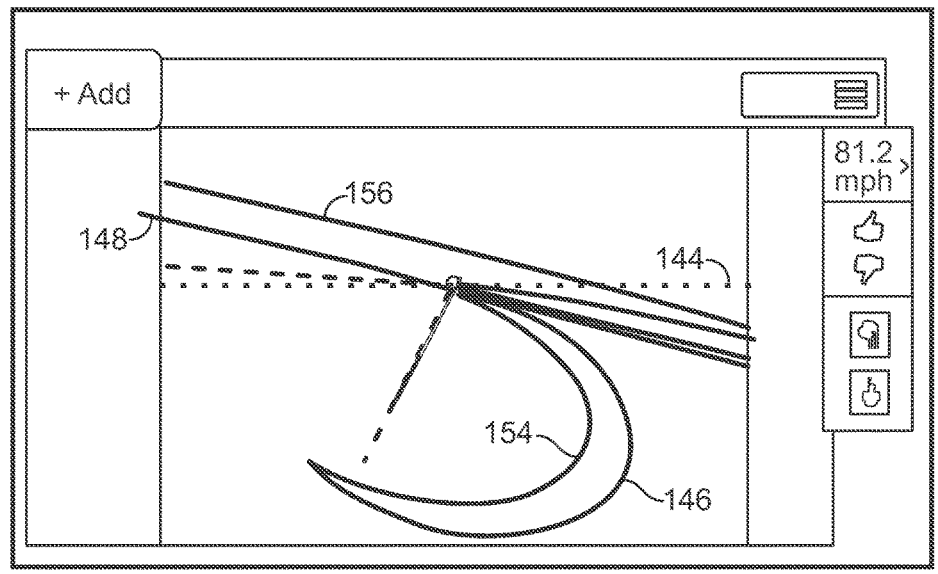
FIG. 16A shows a swing display screen with the outline of a full swing and laser lines drawn from the head of the club and the tail of the club during the full swing where the swing will cause the golf ball to be hooked to the left.
Figure 16B:
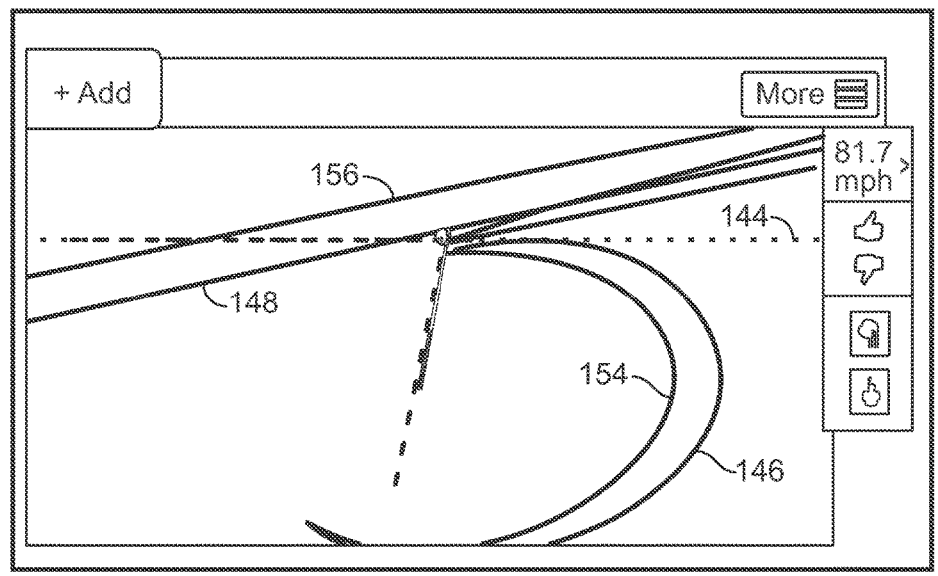
FIG. 16B shows a swing display screen with the outline of a full swing and laser lines drawn from the head of the club and the tail of the club during the full swing where the swing will cause the golf ball to be sliced to the right.

FIG. 16A shows a swing display screen with the outline of a full swing and laser lines drawn from the head of the club and the tail of the club during the full swing where the swing will cause the golf ball to be hooked to the left. As shown before, the outline of the backswing 146 and the outline of the forward swing 154 show the movement of the golf club head throughout the swing. Here, power delivery is much more efficient, but the laser lines are not parallel to either the target line 144, or the club face at impact. That is, the club head laser line from the backswing 148 and the club head laser line from the forward swing are parallel to each other but not parallel to the target line 144. As depicted, the ball will curve left. FIG. 16B shows a swing display screen with the outline of a full swing and laser lines drawn from the head of the club and the tail of the club during the full swing where the swing will cause the golf ball to be sliced to the right. Once again, the outline of the backswing 146 and the outline of the forward swing 154 show the movement of the golf club head throughout the swing. Here, as in FIG. 16A, power delivery is also much more efficient that the swing in FIG. 15, but the laser lines are not parallel to either the target line 144, or the club face at impact. That is, the club head laser line from the backswing 148 and the club head laser line from the forward swing are parallel to each other but not parallel to the target line 144. As depicted, the ball will curve right.

Some described embodiments may use a camera on tablet computer or other mobile device to take video of the player's shot and further use the external sensor data to automatically trim the video to start shortly before the player addresses the ball and to end shortly after impact. A stand-alone camera may also be used. A 6DOF inertial measurement unit, or any other motion capture device, may be used to capture motion data at the same time as the video is captured. After the beginning of a golf swing is identified and impact is detected using the motion sensor, the video may be trimmed to start and end moments before and after the swing starts and ends. Although it is possible for the video to shift out of synchronization with the motion sensor data because of timing differences in the capture, motion capture techniques may be used to locate the golf ball in the camera frame and to identify the frame during which the ball disappears. This frame may then be used as the impact frame, and the video may be re-synchronized. Additionally, motion blur analysis may be applied approximately every two seconds to correct this drift. Then the system may be self-correcting whereby the video data and the 6DOF data may be used to correct each other.

One issue for IMU-based motion capture is that it is not tied to a particular absolute coordinate system. Data is captured relative to the starting point of the motion, and it is impossible to identify how this motion is oriented relative to some absolute point. In golf and other sports this is a problem because the parameters of the motion are important relative to the target. The camera orientation may be used to establish a target line for the shot and to create a useable coordinate system. This may occur using a number of steps. First, using the method described above, video of the golf swing is captured and synchronized with the 6DOF data. Second, once the video is captured, the golf club is identified in the first camera frame, either via an image recognition algorithm or via human input. Third, the angle between the golf club and the bottom of the camera frame on the mobile device is recorded. This is the angle of the projection of the three dimensional golf club onto the plane of the camera. Fourth, the three dimensional scene captured through the motion sensors is simultaneously rotated continuously until the angle between the projection of the golf club onto the camera plane and the bottom of the camera frame is equal to that observed in the video. This process is repeated for several frames during the beginning of the golf swing, where the golf club is moving slowly enough to be visible. Doing this decreases distortion effects, and allows the algorithm to detect not just the magnitude of rotation, but also the direction of the rotation.

Figure 17:
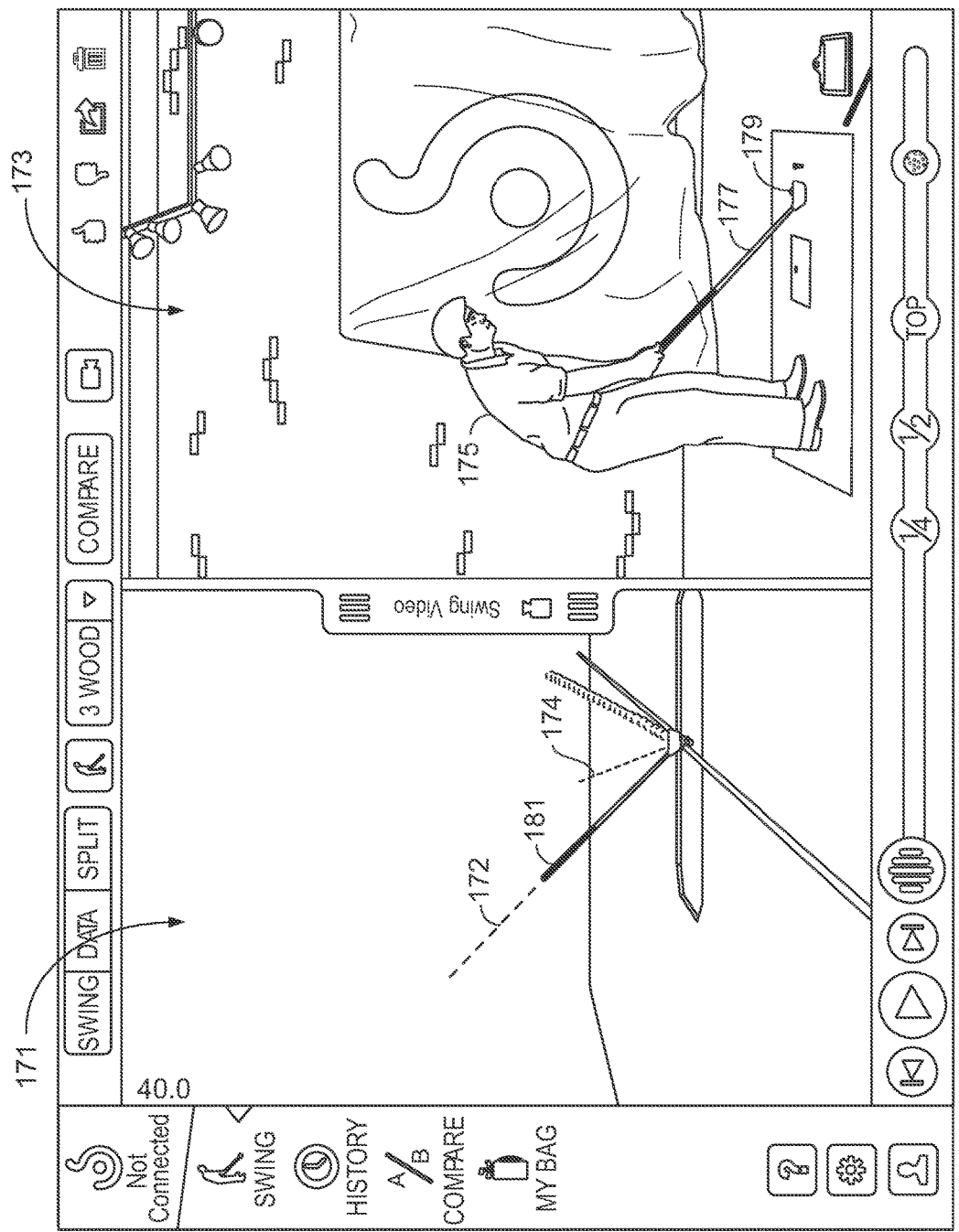
FIG. 17 shows a split screen view of an animation frame and a corresponding video frame of the player addressing the golf ball for a shot.

FIG. 17 shows a split screen view of an animation frame 171 and a corresponding video frame 173 of the player 175 addressing the golf ball for a shot. In the animation frame 171, the line 172 is parallel to the club shaft at address. The line 174 is where the club face points at address. In the video frame 173, a video of the player 175 is shown addressing the ball 179 with a real club 177. The position of the real club 177 in the video frame 173 matches the position of the virtual club 181 in the animation frame 171.

Figure 18:
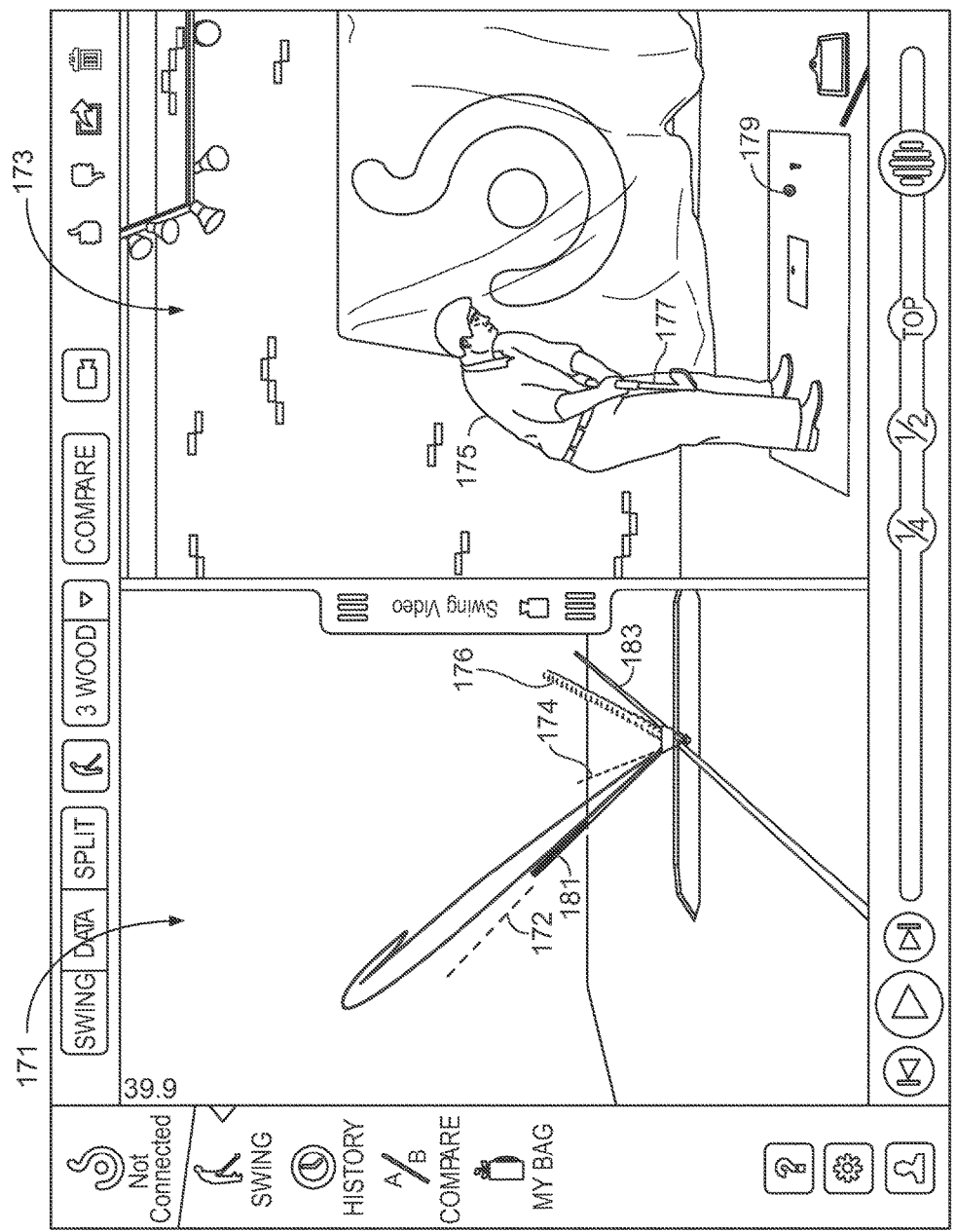
FIG. 18 shows a split screen view of an animation frame and a corresponding video frame of the player in mid-swing.

FIG. 18 shows a split screen view of an animation frame 171 and a corresponding video frame 173 of the player 175 in mid-swing. Again, in the animation frame 171, the line 172 is parallel to the club shaft at address, and the line 174 is where the club face points at address. The line 176 shows where the club face points at impact. As can be seen, the player's 175 shot is not aligned with the player 175 projected shot 183 at address. The video shown alongside the animation allows the player 175 to identify points of error in the swing and to adjust the swing accordingly. In the video frame 173, a video of the player 175 is shown with the player 175 in mid-swing with a real club 177. The position of the real club 177 in the video frame 173 is used to calculate the projected shot 183 based on the position of the virtual club 181 in the animation frame 171. In the animation frame 171, the entire projected swing is shown.

Figure 19:
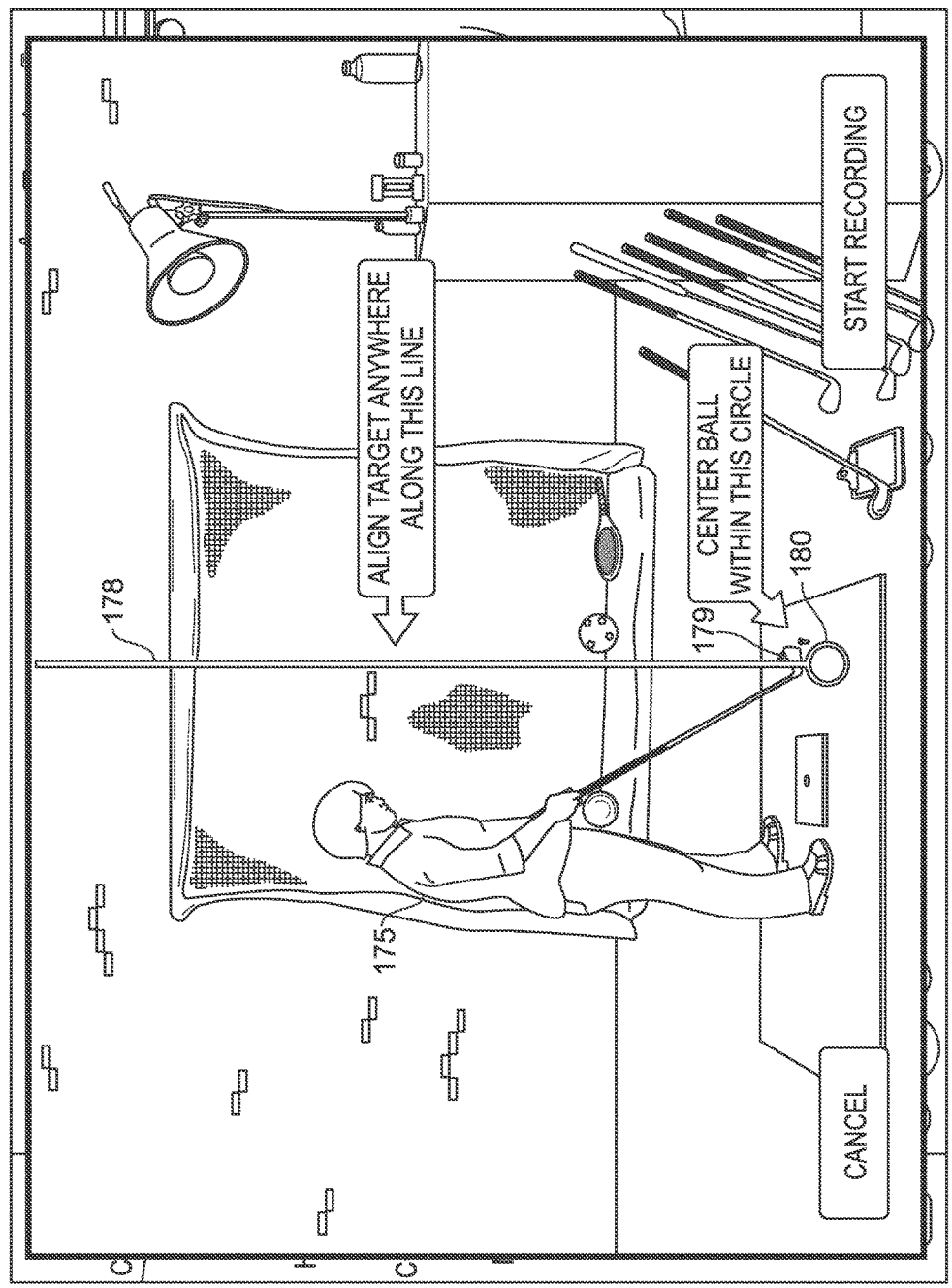
FIG. 19 shows how the player must align the camera on a smart device with the position of the ball before the shot.

FIG. 19 shows how the player 175 must align the camera on a smart device with the position of the ball 179 before the shot. The target line 178 is shown pointing in the direction that the ball 179 will travel if the intended club face impact point and the angle of the club face at address is the same as the actual club face impact point and the angle of the club face at impact. In order for the player 175 to have an accurate video when aligned with the animation, the ball 179 must be aligned within the center of the ball alignment circle 180, which will appear on the screen of the mobile device or tablet computer that has the camera. That is, when the camera, which is on the mobile device or tablet computer, is placed to prepare for video capture, the stationary ball 179 must be shown within the center of the ball alignment circle 180.

Further error correction occurs in described embodiments by using image sensors to determine moving object speeds and coordinates. These embodiments provide accurate and fast determinations of device motion parameters. The following description is the process for estimating the movement of an object for one coordinate axis. The process must be repeated for three orthogonal axes. For one axis, a linear image sensor is used. First, the linear image sensor is used to capture two image frames. A line is selected in the first image frame, and the corresponding line is selected from the second image frame. The selected lines will be parallel to the coordinate axis used. Second, the two selected lines are compared and an autocorrelation function for those signals is determined. Third, where Q is a threshold autocorrelation value unique to each image system and determined during calibration, if the value of the autocorrelation function is greater than Q, the instantaneous speed parameter of an object in the image can be determined by:

$$V = k \cdot R,$$

where k is the calibration coefficient and R is the autocorrelation function. The instantaneous speed parameter of the device itself can be easily determined using the value of the focal length of the image sensor. In other words, the final result is determined by multiplying the instantaneous speed of the image by the focal coefficient. This formula is accurate only where constant time intervals between frames are used for correlation and can give accurate determinations (pixel precision) for large image shifts. Fourth, where Q is greater than the value of the autocorrelation function, the instantaneous speed parameter of an object in the image can be determined by:

A) determining the values of dispersion between two lines using the following formula:

$$D = M\{[y(x) - y(x-\chi)]^2\},$$

where y(x) is the meaning of the signal from one line, y(x−χ) is the meaning of the signal from another line, and M is the mathematical expectation; and B) determining the value of the image shift using the following formula:

$$S = \Delta_m (D_{-1} - D_1) / [2(D_{-1} - 2D_0 + D_1)]$$

where D0 is the dispersion value of the current line and the previous line, D−1 is the dispersion of the previous line and the current line shifted one pixel to the left, D1 is the dispersion value of the previous line and the current line shifted one pixel to the right, and $\Delta_m$ is the size of pixel.

This expression yields a sub pixel precision estimating image shifts with theoretical accuracy of approximately 0.002 pixels and accuracy of approximately 0.005 pixels in practice.

These results can be transformed to device speed using the expression:

$$V = k' \cdot S / \tau$$

where τ is the interval of correlation, and k' is the coefficient based on focal length. This allows better precision of the device speed estimation than data based on gyroscopes and accelerometers alone. From a standard image sensor it is possible to get data for a 2-axis image.

This above-described process may be adapted for use with any number of axes. For example, to determine the instantaneous device speeds on three axes, X, Y and Z, in a rectangular coordinate system with a frequency of about 1000 Hz., a described embodiment will have 3 linear image sensors, one linear sensor for each axis. The embodiment must also have a specialized calculator block for speed determination based on FPGA, ASIC or another like microprocessor device. In practice, linear image sensors have frame rates 300 to 1000 times faster than standard image sensors, which produces clearer images. Thus, signals from linear image sensors are very fast and both parts of the described process may be used to measure both sub pixel image shifts and larger shifts to provide even more accuracy.

Figure 20:
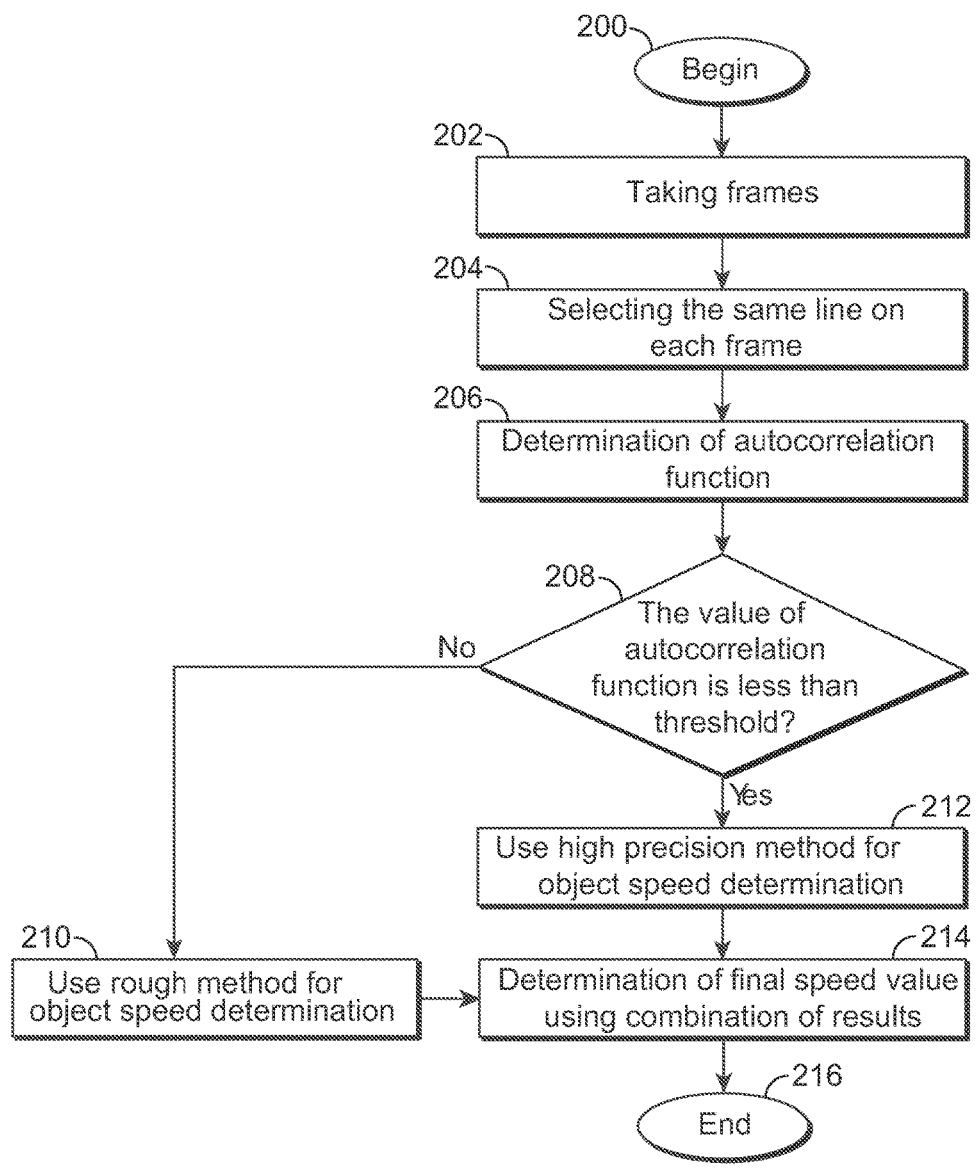
FIG. 20 shows a flow chart of the process for calculating the speed of moving objects using optical image sensors.

FIG. 20 shows a flow chart of the process for calculating the speed of moving objects using optical image sensors. In step 200, the process begins by capturing two image frames with the optical image sensor in step 202. In step 204, the same line on each frame is selected, and in step 206, the autocorrelation function is determined. In step 208, the value of the autocorrelation function is compared to the threshold. If the value of the autocorrelation function is not less than the threshold, step 210 uses the rough method for object speed determination. If the value of the autocorrelation function is less than the threshold, step 212 uses the high precision method for object speed determination. In step 214, the value of the autocorrelation function using the rough method for object speed determination and the value of the autocorrelation function using the precision method for object speed determination are combined for greater accuracy. In step 216, the process ends.

Figure 21:
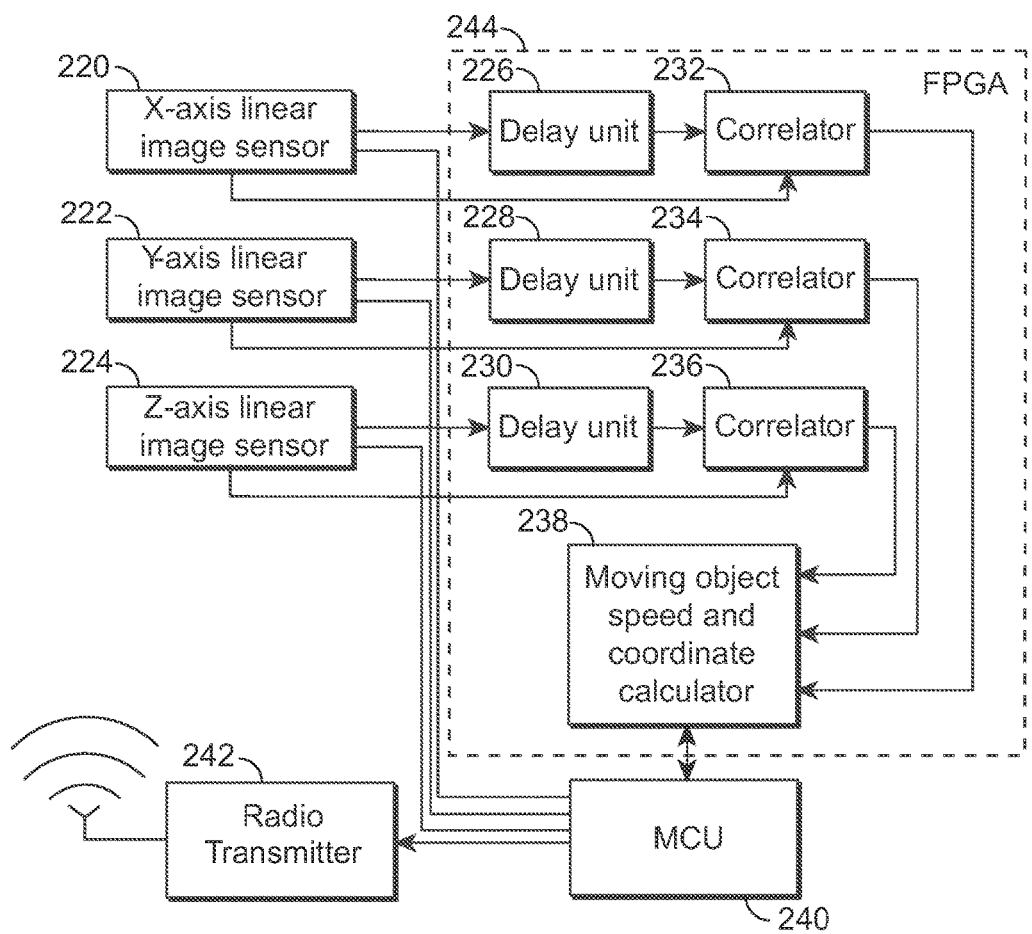
FIG. 21 shows a block diagram of the hardware used for object speeds and coordinates determination based only on readings from optical image sensors.

FIG. 21 shows a block diagram of the hardware used for object speeds and coordinates determination based only on readings from optical image sensors. In this embodiment, the optical image sensors used are three linear image sensors 220, 222, 224 that are orthogonally placed relative to each other so that one is an X-axis linear image sensor 220, one is a Y-axis linear image sensor 222, and one is a Z-axis linear image sensor 224. The X-axis linear image sensor 220 is in communication with a delay unit 226 and an optical correlator 232. The delay unit 226 is in communication with the X-axis linear image sensor 220 and the optical correlator 232 so that the delay unit 226 delays the optical correlator 232 from comparing and correlating the successive optical images until the data for comparison and correlation has been communicated from the X-axis linear image sensor 220 to the optical correlators 232. The Y-axis linear image sensor 222 is in communication with a delay unit 228 and an optical correlator 234. The delay unit 228 is in communication with the Y-axis linear image sensor 222 and the optical correlator 234 so that the delay unit 228 delays the optical correlator 234 from comparing and correlating the successive optical images until the data for comparison and correlation has been communicated from the Y-axis linear image sensor 222 to the optical correlators 234. The Z-axis linear image sensor 224 is in communication with a delay unit 230 and an optical correlator 236. The delay unit 230 is in communication with the Z-axis linear image sensor 224 and the optical correlator 236 so that the delay unit 230 delays the optical correlator 236 from comparing and correlating the successive optical images until the data for comparison and correlation has been communicated from the Z-axis linear image sensor 224 to the optical correlators 236.

In FIG. 21, the output from the optical correlator 232, the optical correlator 234 and the optical correlator 236 is input into a moving object speed and coordinate calculator 238 to calculate speed and coordinate data in three dimensions. Note that in this example, the delay unit 226, the delay unit 228, the delay unit 230, the optical correlator 232, the optical correlator 234, the optical correlator 236 and the moving object speed and coordinate calculator 238 are contained on a field-programmable gate array (FPGA) 244. The speed and coordinate data in three dimensions is output into a microcontroller unit (MCU) 240 where necessary processing, if any, is performed. Output from the MCU 240 is transmitted from a radio transmitter 242 to be received by a portable device, such as a smart phone, a tablet computer and the like. Also note in this example that the MCU 240 is coupled to the X-axis linear image sensor 220, the Y-axis linear image sensor 222, and the Z-axis linear image sensor 224. This is arranged so that the MCU 240 may control the power to the X-axis linear image sensor 220, the Y-axis linear image sensor 222, and the Z-axis linear image sensor 224 when power conservation is a concern.

Figure 22:
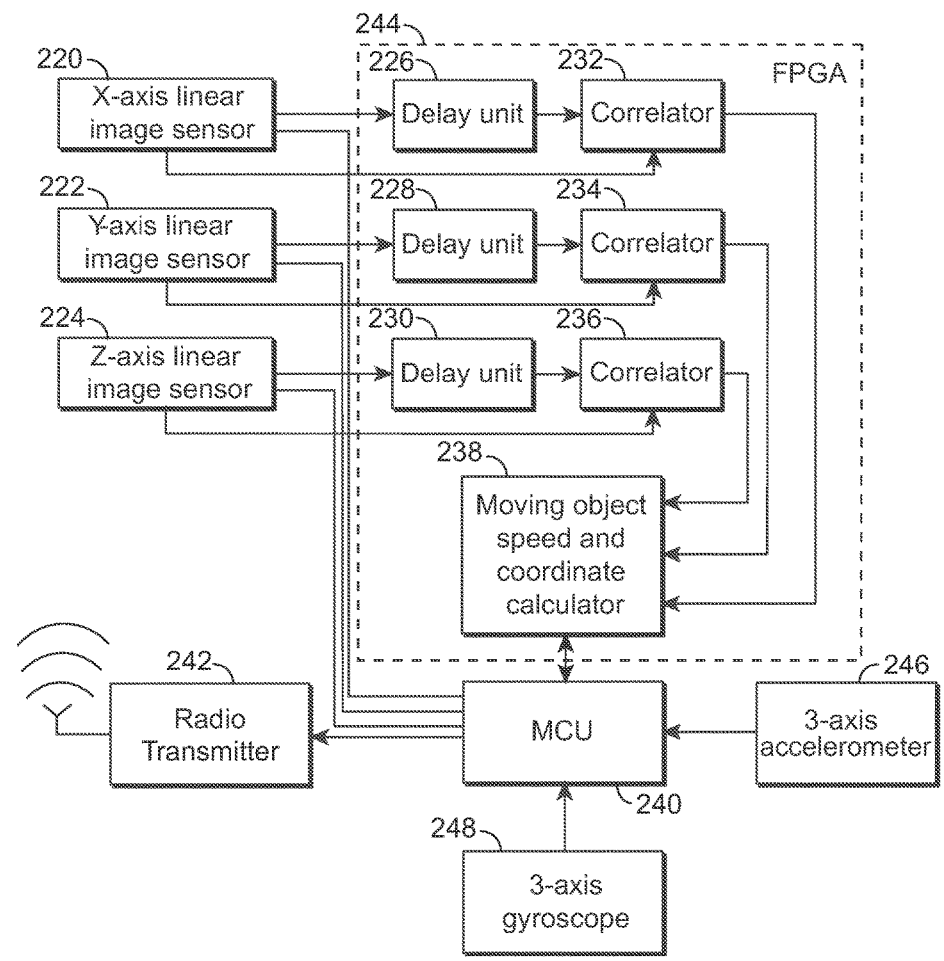
FIG. 22 shows a block diagram of the hardware used for object speeds and coordinates determination based on readings from optical image sensors, an accelerometer and a gyroscope.

FIG. 22 shows a block diagram of the hardware used for object speeds and coordinates determination based on readings from optical image sensors, an accelerometer and a gyroscope. As with FIG. 21, in this embodiment, the optical image sensors used are three linear image sensors 220, 222, 224 that are orthogonally placed relative to each other so that one is an X-axis linear image sensor 220, one is a Y-axis linear image sensor 222, and one is a Z-axis linear image sensor 224. The X-axis linear image sensor 220 is in communication with a delay unit 226 and an optical correlator 232. The delay unit 226 is in communication with the X-axis linear image sensor 220 and the optical correlator 232 so that the delay unit 226 delays the optical correlator 232 from comparing and correlating the successive optical images until the data for comparison and correlation has been communicated from the X-axis linear image sensor 220 to the optical correlators 232. The Y-axis linear image sensor 222 is in communication with a delay unit 228 and an optical correlator 234. The delay unit 228 is in communication with the Y-axis linear image sensor 222 and the optical correlator 234 so that the delay unit 228 delays the optical correlator 234 from comparing and correlating the successive optical images until the data for comparison and correlation has been communicated from the Y-axis linear image sensor 222 to the optical correlators 234. The Z-axis linear image sensor 224 is in communication with a delay unit 230 and an optical correlator 236. The delay unit 230 is in communication with the Z-axis linear image sensor 224 and the optical correlator 236 so that the delay unit 230 delays the optical correlator 236 from comparing and correlating the successive optical images until the data for comparison and correlation has been communicated from the Z-axis linear image sensor 224 to the optical correlators 236.

As in FIG. 21, in FIG. 22, the output from the optical correlator 232, the optical correlator 234 and the optical correlator 236 is input into a moving object speed and coordinate calculator 238 to calculate speed and coordinate data in three dimensions. Note that in this example, the delay unit 226, the delay unit 228, the delay unit 230, the optical correlator 232, the optical correlator 234, the optical correlator 236 and the moving object speed and coordinate calculator 238 are contained on a field-programmable gate array (FPGA) 244. The speed and coordinate data in three dimensions is output into a microcontroller unit (MCU) 240 where necessary processing, if any, is performed. Output from the MCU 240 is transmitted from a radio transmitter 242 to be received by a portable device, such as a smart phone, a tablet computer and the like. Also note in this example that the MCU 240 is coupled to the X-axis linear image sensor 220, the Y-axis linear image sensor 222, and the Z-axis linear image sensor 224. This is arranged so that the MCU 240 may control the power to the X-axis linear image sensor 220, the Y-axis linear image sensor 222, and the Z-axis linear image sensor 224 when power conservation is a concern.

The example in FIG. 22 demonstrates how the speed and coordinate data from the moving object speed and coordinate calculator 238 is combined with linear acceleration data from a three-axis accelerometer 246 and angular velocity data from a three-axis gyroscope 248 in the MCU 240 and transmitted from the radio transmitter 242 to be received by a portable device, such as a smart phone, a tablet computer and the like. Very often, when using data based on accelerometer and gyroscope output, there is a need to correct the error to the output caused by drift and other factors. To correct the error to the accelerometer and gyroscope output, the data from the optical image sensors may be used. In many cases, the video correction is not needed often, and the MCU 240 can turn off the power to the linear image sensors 220, 222, 224. Variations of the above embodiments may be realized in various forms, including as a single system on one chip or with the calculator block on one silicon crystal.

Figure 23:
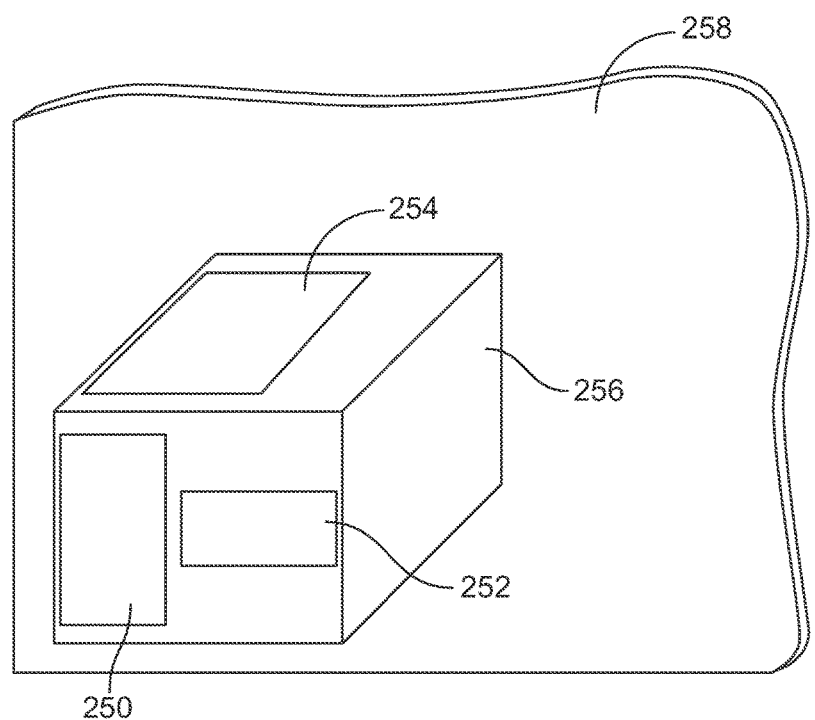
FIG. 23 shows a perspective view of linear image sensor construction on a printed circuit board.

FIG. 23 shows a perspective view of linear image sensor construction on a printed circuit board 258. A linear image sensor 250, a linear image sensor 252, and a linear image sensor 254 are mounted orthogonally to each other on a mounting block 256, which is attached to the printed circuit board 258. The orthogonal arrangement of the linear image sensor 250, the linear image sensor 252, and the linear image sensor 254 show the arrangement used for a rectangular coordinate system in three-dimensional space. This arrangement requires very little space on the printed circuit board 258.

Having the right swing is important to golfers. It not only gives the most powerful, effective and accurate hits to the ball, but also minimizes the risk of body injury. The swings of amateur golfers tend to exhibit many typical faults. There are around 60 kinds of typical swing faults. A swing of an amateur golfer may include several such faults simultaneously. Traditionally, a coach needs to evaluate the swings and to develop a training program to correct these swing faults. This is expensive.

Embodiments of the present inventions provide inertial sensor data of swings by recording the linear acceleration, and the angular velocity of a swinging club at a temporal sampling rate of approximately 850 Hz. On average, a swing lasts about 1.5 seconds. Thus, each swing produces approximately 1,500 time-stamped motion vectors for each swing. Based on the vectors, the 3D trajectory of a golf ball struck by the recorded swinging club may be solved.

Embodiments of the inventions also include motion attributes recognition systems and methods, and, more specifically, described embodiments recognize faults in the movements of a golfer's swings. Consequently, further embodiments include virtual coaching systems and methods on electronic devices that recognize the faults as attributes of the golfer's imperfect swing based on the golfer's motion data and that provide feedback in the form of information and advice. Thus, a golfer may use an electronic device to receive golf swing coaching.

Embodiments of the present inventions further allow users to submit their swing data to a service, such as a data collection service through the cloud for example, where the service may collect motion data for a large number of swings, in the millions for example. Where the collected swing data is associated with video, some pro golfers may be able to view the videos, to evaluate the swings, and to detect the typical faults in the video swings. However, most golfers may not be able to evaluate the swings for faults based on watching videos, and neither pro golfers nor amateur golfers are able to detect faults based on inertial data directly. Therefore, it is desirable that embodiments of the present inventions recognize swing faults using a learning machine, or system, to interpret the collected golf swing inertial data. Such systems, or methods implementing such systems, shall have the intelligence to recognize swing faults from inertial data, to analyze the swing based on all the data and faults, and to evaluate the swing and suggest a course of action for improvement.

The described embodiments of the motion attribute recognition systems and methods recognize sixty-five distinct faults, separated into the following four categories: 1) Impact & Follow-through faults; 2) Downswing faults; 3) Backswing faults; and 4) Address faults.

The Impact & Follow-through faults include the following motion attributes:
  body stops rotation
  right hip not far enough forward/does not finish fully on left leg
  reverse "C"
  upper finishes nearer target than lower
  arms swinging down target line
  excessive wrist/hand blocking
  left elbow up & behind lacking width
  arms & club out to in too low & left
  excessive wrist/hand rotation
  excessive wrist/hand throw & slap
  club face exits rolled over & too closed The Impact & Follow-through faults also include selecting for each of these faults, whether or not the golfer's swing was within one plane or within two planes. The user must choose one or the other.

The Downswing faults include the following motion attributes:
  raising spine & thrusting hips
  body weight not sufficiently on left leg (bump)
  hip slide & shoulder tilt
  hips backing up
  upper body not turned from the top/insufficient turn
  head moving towards target
  shoulders turning from the top
  stand up body turn
  right elbow leading/left arm pulling/outer circle
  in to out arm swing
  casting from the top
  arms thrown out away from body/out to in The Backswing faults include the following motion attributes:
  flat turn
  excessive right side turn/hip turn outraces shoulder turn
  insufficient turn excessive head movement behind ball
raising spine
shoulder tilt/hip slide
not moving behind ball
reverse pivot/upper body moves towards target
right elbow down in front/left arm rolling up away/club head inside too quick
arms too inside
arms too outside
arms/club too flat
club laid off
both arms in front
arms above plane at the top
right elbow up & behind lacking width/left arm bent
club across the line
club face too closed at top
club face too open at top The Address faults include the following motion attributes:
spine too upright/excessive knee bend
bent over too much
spine tilt away from target/"K" position
spine tilting towards target
aim too far left
aim too far right
shoulders & hips closed
shoulders open to hips
too far away from ball
too close to ball
stance too narrow
stance too wide
right foot flared out excessively
left foot flared out excessively
left foot perpendicular to the target line
ball too far forward
ball too far back
grip too strong
grip too weak
hands held too high
hands held too low
hands too far behind ball
hands too far ahead of ball The collected motion data may be stored and used within a motion attribute recognition system so that the individual attributes may be recognized, related to a portion of the swing, weighted, related to a method of improvement, and presented to a golfer with a lesson on the golfer's electronic device on how to improve his or her swing. The lesson may include animated swings with statistics, video replay, text instruction, and all the features described above. Essentially, a golfer may have an instant virtual coach whenever desired. Additionally, because of the popularity of golf and because current data aggregation methods would allow the collection of data from an enormous number of swings, in the millions or more, it would not be practicable to have golf pros evaluate every swing and correct their own observations when mistaken. Rather, the described systems and methods may use machine learning techniques to analyze and to use the raw data.

Figure 24:
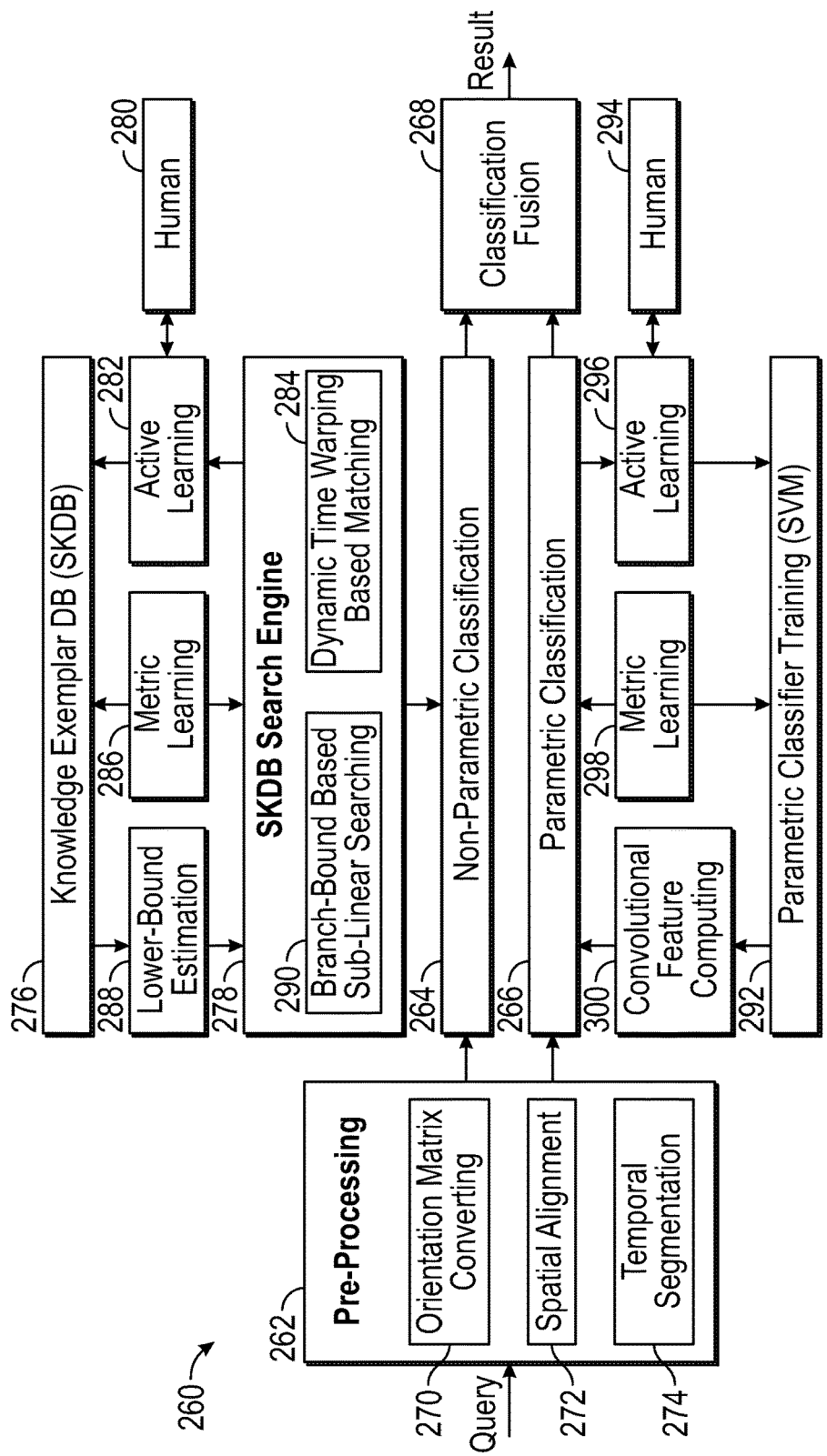
FIG. 24 shows a system block diagram for a motion attribute recognition system.

FIG. 24 shows a system block diagram for a motion attribute recognition system. The motion attribute recognition system 260 has four main components. The first component is a pre-processing component 262; the second component is a non-parametric classification 264 component; the third component is a parametric classification 266 component; and the fourth component is a classification fusion 268 component.

The pre-processing component is used to normalize swing data so that data from one swing may be compared to data from one or more different swings. This normalization is needed for at least two reasons. First, the motion data is received as raw sensory data from motion measuring components, such as accelerometers, gyroscopes, magnetometers, etc., and a swing is a spatial-temporal sequence. At each instant, a swing has a set of fifteen instantaneous spatial observations, including the 3D Cartesian coordinates of the golf club, the 3D orientation of the club, the club head speed, the club face angle within the plane of travel (PoT), and the angle of PoT to the ground. The vectors representing these instantaneous features are useful to estimate PoT, and most machine learning methods rely on vectorized data. However, because some of these instantaneous features are computed over a very small time interval, they can be inaccurate. Second, different swings exhibit different time duration. Some swings are longer than others. On one hand, some swings may be faster than others. On the other hand, swing data contain some indefinite periods of time at the beginning of the swing and after the ball has been struck. Thus, because of the different swing time durations, the swing data cannot be represented directly with vectors. Nevertheless, properly pre-processing the raw data allows accurate orientation between and among data from large numbers of swings so that separate motion attributes may be recognized using the calculated PoT and the vectorized data and so that data from different individual swings may be compared.

The pre-processing component 262 has three major steps: 1) converting from an orientation matrix 270; 2) spatial alignment 272; and 3) temporal segmentation 274.

The orientation matrix converting 270 occurs because in the received form of the raw data, the 3D orientation of the club head is represented by a 3×3 rotation matrix R, and thus a 9-dimensional vector. When comparing two orientations and/or interpolating two orientations, it is inconvenient to use a rotation matrix because the Frobenius norm of the difference between two rotation matrices may not be the best choice to measure the similarity of the two orientations, as the measurements are inaccurate especially when the two orientations are very close. Additionally, although a rotation matrix is not the only representation for orientation, and one may also use the Euler angles, computing Euler angles from a rotation matrix may be inaccurate when the rotation is tiny.

Therefore, here, a more convenient representation, called quaternion, is used for orientation. A quaternion is a 4-dimensional vector $q \in R^4$, and it represents an orientation as a rotation angle $\Theta$ over an axis represented by a unit vector u. A quaternion is written as:

$$q = [q_0, q_1, q_2, q_3]^T = \pm \left[\cos\frac{\theta}{2}, u^T \sin\frac{\theta}{2}\right]^T.$$

One important property for quaternion is that it is a unit vector, i.e., $q^T q = 1$. The relations between quaternion q and the rotation matrix R are:

$$R = \cos\theta I + \sin\theta [u]_x + (1 - \cos\theta) uu^T,$$

which is called the Rodrigues formula. Thus, because a quaternion is a unit vector, it may be used in this formula, which operates on unit vectors.

There are several ways to measure the distance between two rotations using quaternion. Here the following is used:

$$D(q_1, q_2) = 1 - |q_1^T q^2|$$

It can be verified that this is a distance metric, and $D(q_1, q_2) \in [0, 1]$.

A quaternion is very convenient for interpolating orientations. The resulting quaternion is just the normalized convex linear interpolation of two known quaternions. Interpolating two quaternions of the same axis results in a quaternion of the same axis. This is much more convenient than using the rotation matrix for rotationally aligning and comparing data from different swings.

The purpose of spatial alignment 272 is to rotate the action data, such as golf swing data, around the y-axis (vertical to the ground plane defined by the xz-plane), so that the starting plane for all actions are aligned. To do so in the golf swing data, one must estimate the two planes of travel (PoT).

When estimating the two planes of travel of the club, the instantaneous angle of the PoT to the ground is obtained by taking the cross-product of club head position at two consecutive frames. This method can be inaccurate when the two vectors are fairly close to each other, e.g., when in the beginning of the swing and when the club head reaches the top position. Using more club head positions can be more helpful.

Some studies on golf swings seem to imply that estimating the travel plane(s) of the club may be useful to identify the swing as a one-plane swing or a two-plane swing. In a one-plane swing, the club during the golfer's backswing and the club during the golfer's downswing travel in the same plane, and in a two-plane swing, the club during the golfer's backswing and the club during the golfer's downswing travel in different planes.

Here, the following method to estimate the PoT is used: 1) first, segment a swing into several segments based on top of backswing (TOBS), impact, quarter and three-quarters locations of the swing; 2) for each segment, collect data matrix $D=[x_s, \ldots, x_e]$, where $x_s$ and $x_e$ are the starting and ending features of this segment; and 3) perform 2D reconstruction of D as these features should reside on a 2D plane in 3D. This can be done by performing singular vector decomposition (SVD) on D and discarding the subspace corresponding to the smallest singular value, or other methods of dimension reduction may be used; 4) for any two segments, one may compute the largest principal angle between the two 2D sub-spaces represented by the two 2D reconstructed data matrices; and 5) one may also easily obtain the angle of PoT to the ground as well. As more data samples are used, this method gives more reliable and robust estimation to the plane of travel.

Vectorizing the swing data is important because most machine learning methods act on vector space, i.e., the data needs to be represented as a vector. However, as swings may have different time durations, they cannot be directly treated as vectors. But, if one just takes the initial step of chopping the sequence into a fixed number of segments, and, if for each segment, one takes the average vector of the feature vectors over this segment to represent it, the swing data will cluster so that the motion attributes may be recognized. For example, if one takes 200 segments, and uses only one (x, y, z) Cartesian coordinate for each segment, then one ends up with a 600-D vector for a swing. In other words, every point in this 600-D space $R^{600}$ is a swing. When the swings are distributed in the space $R^{600}$, they are separately clustered for left-handed and right-handed golfers.

The purpose of temporal segmentation 274 is to locate the actual segment of the movement in a temporal action sequence. This is performed by locating and ignoring the non-informative segments before and after the movement. Specifically, this is done by: 1) locating the non-moving segment before the movement by finding the start of the motion data to determine the thresholds of the motion; and 2) locating the non-informative segment after the movement by using the "impact" time stamp from the motion data.

In sum, the pre-processing takes the raw swing data, in which swings have varying temporal lengths, and normalizes it for comparison by orienting each swing in the same rotational space, by finding the swing planes and orienting the swings to share a starting plane, by vectorizing the swings and plotting the 2D data in 3D space to locate motion attributes, and by segmenting the swing so that the data space only includes data taken from the time the swing starts until impact. Once the pre-processing has been accomplished, the swing data is ready for comparison and analysis.

The non-parametric classification 264 component consists of three major blocks, the swing knowledge exemplar database (SKDB) 276, the SKDB search engine, and the non-parametric classification 278.

The SKDB 276 consists of a large set of annotated actions, each action with its own features after pre-processing the raw sensory data and its action attributes. Specifically, for a swing action exemplar, its action feature is a sequence of 10-dimensional vectors, or spatial features, and its attributes are a subset of 104 different golf swing attributes. For golf swings, there are five types of spatial features that provide ten dimensions. X-Y-Z coordinates provide three dimensions. The orientation quaternion provides four dimensions. The instantaneous angle of the club head within the traveling plane provides one dimension. Impact provides one dimension. The instantaneous angle of the traveling plane to the ground provides one dimension.

To obtain a high-quality SKDB 276, active learning is used. As it is infeasible to have a golf instructor, or human 280, tag a huge number of swings, the gain from the efforts of the golf instructors should be maximized. That is, the active learning in the defined embodiments combines human intelligence and machine intelligence. The SKDB search engine 278 automatically identifies informative swings for the human instructors to annotate and spots inconsistencies in the human knowledge, and the humans 280, who may be instructors, provide tagging information to train the SKDB search engine 278. This combination of SKDB search engine 278 and human 280 input provides the active learning 282 for the SKDB 276. In the described embodiments, three schemes for active learning 282 are used.

The first scheme is spotting inconsistency. As several golf instructors will be used to provide annotations, or tagging information, for the swings, they may have different opinions on some swings. In addition, a human 280 instructor may miss tagging some attributes for some swings but may provide such attributes for other similar swings. All such scenarios create inconsistencies in the tagging. To spot the inconsistencies, the defined embodiments perform pair-wise checks for all tagged swings and find those that have small swing distances but have significantly different tags. Such a subset of tagged swings gets sent back to human 280 instructors to review. The second scheme involves discovering typical swings. Typical swings have certain swing patterns. To discover such typical patterns, a large number of untagged swings are collected, e.g., 5,000 or more, and subjected to k-Medoids clustering. The medoids, or the cluster centers, are the typical swings. Human 280 instructors are used to tag this set of typical swings. The third scheme involves identifying confusing swings. Confusing swings are those located on the boundaries of different clusters. After the k-Medoids clustering is performed, the set of swings on the cluster boundaries are identified. Instructors will then tag those set of swings on the cluster boundaries. Thus, interactions between the defined systems and instructors will iterate.

To select a set of N swing exemplars, the k-Medoids clustering algorithm is used to find representative actions for the action clusters. Using a k-Means algorithm must compute the centroid, or the mean, of each cluster. In some case, however, the data space may be a manifold. In that situation, there may be constraints among the elements of the data vector, and thus the Euclidean mean of a set of data may violate these constraints. Thus, the mean would not be a valid data sample. In contrast to k-Means, k-Medoids chooses data points themselves as the cluster centers, called medoids. This allows arbitrary distance measurements for data points, while the k-Means algorithm only allows Euclidean distance measurements. Thus using k-Medoids is more robust to noise and outliers than k-Means because it minimizes the sum of pair-wise dissimilarities instead of the sum of Euclidean distances.

A medoid is defined as the data point in a cluster for which the average dissimilarity to all other data points within this cluster is minimized. The most common realization of k-Medoids clustering is the Partitioning Around Medoids (PAM) algorithm, which operates as follows: 1) Step 1 involves initialization and randomly selecting k of the N data points as the medoids; 2) Step-2 involves labeling by associating each data point to its closest medoids; 3) Step-3 involves swapping V medoids m, and V non-medoids data point o to compute the total cost of the configuration and to select the configuration with the lowest cost; and 4) Step-4 involves repeating Step-2 and Step-3 until convergence.

The SKDB search engine 278 is the core component of the defined systems. The SKDB search engine 278 searches the SKDB 276 and finds a set of "similar" swing exemplars that match the input swing action data when querying in this application. The innovations lie in two aspects, finding a good match of action data in the SKDB 276 using the SKDB search engine 278 and performing a fast search when the SKDB 276 is large. Finding a good match of action data in the SKDB 276 involves dynamic time warping based matching 284 (DTW), and performing a fast search of the SKDB 276 involves metric learning 286.

After spatial alignment is done, temporal alignment must be applied to handle the different time durations of the swings that have been temporally segmented. Temporal alignment is also called temporal registration. For two swings, suppose one has made the correspondences of their start points and end points, respectively, temporal alignment finds the time correspondences between the two swings. That is, dynamic time warping based matching 284 is used to find the temporal alignment of two sequences, which may be of different temporal lengths, to evaluate the similarity of the two sequences by warping the time comparison to create a single time sequence for comparison, e.g. so the starts of the swings align, the tops of swings align, the points of impact align, etc. Thus, dynamic time warping based matching 284 can work on two sequences of different lengths. A time instant at one sequence can correspond to a continuous time segment of another sequence, and vice versa. Dynamic time warping based matching 284 enables local deformation (expanding or shrinking) of the sequence for matching. The solution is based on dynamic programming and is used in the described embodiments.

Suppose there are two sequences $X=\{x_1, \ldots, x_N\}$ and $Y=\{y_1, \ldots y_M\}$ where M and N are the length of the two sequences, respectively. $x_t$ is the spatial feature of X at time t. Temporal alignment is a warping path $$P=\{(p_x^t, p_y^t)\},$$

where $$p_x \in [1, N] \text{ and } p_y \in [1, M].$$

$(p_x^t, p_y^t)$ is a corresponding pair of time stamps of the two sequences. Dynamic time warping based matching 284 is targeted on finding an optimal path such that $$\min_P \sum_t d(x_{p_x^t}, y_{p_y^t})$$

where $$d(x_{p_x^t}, y_{p_y^t})$$

is the distance between the two spatial features at the two corresponding time instances (i.e., after temporal alignment). Thus, following the spatial alignment and the temporal alignment with dynamic time warp, given a sample of swing data from a recent golf club swing, the SKDB may be searched for the swing data that most closely resembles the recent sample.

For the dynamic time warping approach, the optimal time correspondence (or the warping path) is obtained, and then, the distance between two swings can be computed over this warping path. This approach turns out to be accurate, but it is computationally intensive due to its dynamic programming process. When the dynamic time warping approach is implemented in C++ or similar language, the database can be searched at acceptable speeds when the database is relatively small. Other vector space metrics may be used to measure the similarity or distance between two swings.

The following gives the pseudo code for a non-recursive implementation of DTW:

```
function [Dist, K, P]=DTW(X,Y)
% Pseudo code for dynamic time warping
% X and Y are two input sequences of length n and m, respectively
% Dist is the DTW distance
% K is the length of the warping path
% P is the warping path
% step 1: compute distance D matrix
% step 2: initialize cumulative C matrix
C=zeros(N,M);
C(1,1)=D(1,1);
for n=2:N
    C(n,1)=D(n,1)+C(n-1,1);
end
for m=2:M
    C(1,m)=D(1,m)+C(1,m-1);
end
% step 3: compute cumulative matrix
for n=2:N
    for m=2:M
        C(n,m)=D(n,m)+min[C(n-1,m), C(n-1,m-1), C(n,m-1)];
    end
end
Dist=C(N,M);
% step 4: backtracking to obtain the warping path
n=N; m=M; K=1;
P=[ ]; P(1,:)=[N, M];
while (n+m)!=2
```

```
    if n==1
        m --;
    else if m==1
        n --;
    else
        [v, index]=min[C(n-1,m),C(n,m-1),C(n-1,m-1)];
        switch index
            case 1:
                n --;
            case 2:
                m --;
            case 3:
                n --;
                m --;
        end
    end
    K++;
    P=cat(P, [n,m]);
end
Dist=Dist/K;
```

Traditional dynamic time warping methods are only concerned about warping paths with 1-dimensional sequences. The described systems and methods provide metric learning 286 to handle multi-dimensional sequences by learning the metric of the multi-dimensional spatial features.

There are two important issues in DTW: (1) the warping path, and (2) the distance measure of the spatial features. At a time instant, the swing has a 10-dimensional spatial feature, 3 for (x,y,z), 4 for the rotation quaternion, 1 for club head angle, 1 for impact, and 1 for traveling plan angle. Such 10 features are from different modalities and have different physical meanings and units, and they are not in a vector space, as a quaternion lies in a nonlinear manifold. Different weights on these modalities define different distance metrics for spatial features, and thus, lead to different warping paths. Thus, one must automatically determine the weightings of these modalities that will provide the optimal matching of the time sequence data. The methods, processes and systems implementing this is referred to "metric learning". The described embodiments provide a plausible mathematical based formulation and implementation of the metric learning.

As described above, the weighting on different modalities of the spatial features influences the distance or similarity between two swings. Different weights will lead to different warping path, and thus different swing distances. One must determine whether to give more weights to the modality of x/y/z coordinates, or to the modality of the club head orientations. One must also determine what weights to give to all the modalities in combination to get the optimal weighting This problem of finding the optimal weighting may be solved by automatically "learning" from the tagged data a set of modality weights, such that the similarity scores become higher when swings share the same attributes. In other words, under the optimal weights, similar swings are closer to each other. A gradient-based solution to find an optimal solution to the modality weight distribution is generally applicable.

First, the concept of soft nearest neighbor, a concept where a sequence sample can always be treated as the nearest neighbor of another sample with some probability, depending on their distance, is used. The further the distance between samples, the less the probability that the two samples will share an attribute. For one sample X, among all of its soft neighbors, there is a subset of samples that have the same class of a certain attribute X. For any attribute, a sample must be associated with one of two classes: having this attribute or not. The aggregation of the probabilities of this subset of neighbors evaluates the probability that this sample X will be correctly classified or not.

The analytical solution to this optimization problem is derived from a gradient-based optimization algorithm where the name of the expected, i.e., weighted average, distance of the nearest neighbor is the heterogeneous neighbor distance, and the name of the expected distance of the nearest neighbor of the same attribute class is the homogenous neighbor distance. The optimal solution is achieved when these two distances are equal. The metric learning algorithm considers all the swing attributes and can also work on a subset, or a weighted subset, of the attributes, important attributes may be emphasized.

In mathematical terms, this analytical solution of finding the optimality condition for the metric learning may be defined as follows:

Suppose there are C independent attributes (note, not classes, as each sample can have several attributes), and N samples. The spatial feature at a certain time instant is $x \in \mathbb{R}^n$, and the length of the sequence is T. Assume that all sequences have the same time duration. So, a sequence can be represented by $$X = \begin{bmatrix} x_1 \\ \vdots \\ x_T \end{bmatrix} \in \mathbb{R}^{nT}.$$

Now, define the distance between two sequences $X_i$ and $X_j$ as follows:

$$D(X_i, X_j) \triangleq \sum_{t=1}^{T} d(x_t^i, x_t^j).$$

The above definition assumes the two sequences have been aligned. As an example, the distance between two spatial features can be defined as a Mahalanobis distance as follows:

$$d(x_t^i, x_t^j) = (x_t^i - x_t^j)^T A^T A (x_t^i - x_t^j).$$

But here, consider a more general nonlinear distance of multiple independent modalities:

$$d(x_t^i, x_t^j) = \sum_{m=1}^{M} \lambda_m d_m(x_t^i, x_t^j) \quad (1)$$

where there are M modalities, and $\lambda_m$ is the weight for the m-th modality. Within each modality, the distance $d_m$ can be natively defined by using ad hoc metrics. It is clear that the set of $\Lambda = \{\lambda_1, \ldots, \lambda_m\}$ are the parameters of the new metric to be learned. Denote $D_m$ the sequence distance under a certain modality by:

$$D_m(X_i, X_j) \triangleq \sum_{t=1}^{T} d_m(x_t^i, x_t^j).$$

It is clear that:

$$D(\chi_i, \chi_j) = \sum_{m=1}^{M} \lambda_m D_m(\chi_i, \chi_j). \quad (2)$$

Now, formulate the objective for the metric learning.

For any two sequences $X_i$ and $X_j$, treat one as the nearest neighbor of the other with a certain probability:

$$p_{ij}(\Lambda) = \frac{e^{-D(\chi_i, \chi_j)}}{\sum_{k \neq i} e^{-D(\chi_i, \chi_k)}}, \text{ and } p_{ii} = 0. \quad (3)$$

Therefore, with probability $p_{ij}$, sequence $X_i$ will have the same attributes that sequence $X_j$ has. Now consider the probability that the nearest neighbor has the same class as the sample of concern i. This scenario has a set of attributes, indexed by $a \in A$. For each attribute a, the sample can be a positive class sample (i.e., has this attribute), or negative otherwise. For an attribute a, here one must compute the probability that a neighbor j shares the same class as i, i.e., if i has (or does not have) attribute a, then j also has (or does not have) this attribute. For the sample i, integrating all of its soft neighbors bearing the same class as i, its same class neighbor probability can be denoted by:

$$p_i(a, \Lambda) = \sum_{j \in \Omega_i(a)} p_{ij}(\Lambda), \text{ or } p_i(a) = \sum_{j \in \Omega_i(a)} p_{ij} \text{ for short}$$

where $\Omega_i(a)$ is the set of samples that share the same class as sample i for attribute a. The concept of $p_i(a)$ is clear: it gives the probability that sample i can be correctly classified by the nearest neighbor classifier for attribute a. An interesting case to note is: when sample i is an isolated one, i.e., it is the only one of its class and none of the rest in the dataset has the same class label (it is not uncommon in our swing tagging for some rare attributes), $p_i(a)=0$.

Overall, for a set of data, one can have the expectation that data is correctly classified for attribute a, as $$p(a, \Lambda) = \sum_{i=1}^{N} p_i(a, \Lambda) = \sum_{i=1}^{N} \sum_{j \in \Omega_i(a)} p_{ij}(\Lambda)$$

where $\Lambda$ are the metric parameters defined above. Considering all attributes, here the objective of the metric learning is to find the optimal $\Lambda^*$, such that $$\max_{\Lambda} p(\Lambda) = \sum_{a \in A} p(a, \Lambda) = \sum_{a \in A} \sum_{i=1}^{N} \sum_{j \in \Omega_i(a)} p_{ij}(\Lambda). \quad (4)$$

As an alternative formulation from the perspective of data likelihood instead of the expectation, the log likelihood is:

$$L(a, \Lambda) = \sum_{i=1}^{N} \log p_i(a, \Lambda) = \sum_{i=1}^{N} \log \left\{ \sum_{j \in \Omega_i(a)} p_{ij}(\Lambda) \right\}.$$

Then, one can define an alternative objective function as:

$$\max_{\Lambda} f(\Lambda) = \sum_{a \in A} L(a, \Lambda) = \sum_{a \in A} \sum_{i=1}^{N} \log \left\{ \sum_{j \in \Omega_i(a)} p_{ij}(\Lambda) \right\}. \quad (5)$$

To obtain the optimal solution to $\Lambda$, take the gradient-based iterative approach, $$\Lambda^{k+1} \leftarrow \Lambda^k + \epsilon \frac{\partial p(\Lambda)}{\partial \Lambda}$$

where $$\frac{\partial p(\Lambda)}{\partial \Lambda}$$

is the gradient, and $\epsilon > 0$ is the step size.

One can derive the gradient, $\forall m$, as follows:

$$\frac{\partial p(\Lambda)}{\partial \lambda_m} = \sum_{a}^{N} \sum_{i=1}^{N} \sum_{j \in \Omega_i(a)} \left\{ p_{ij} \left[ -\sum_t d_m(x_t^i, x_t^j) + \right. \right. \quad (6)$$

$$\left. \left. \sum_{k \neq i} \left( p_{ik} \sum_t d_m(x_t^i, x_t^k) \right) \right] \right\}$$

$$= \sum_{a} \sum_{i=1}^{N} \left\{ p_i(a) \left[ \sum_{k \neq i} \left( p_{ik} \sum_t d_m(x_t^i, x_t^k) \right) \right] - \quad (7) \right.$$

$$\left. \sum_{j \in \Omega_i(a)} \left( p_{ij} \sum_t d_m(x_t^i, x_t^j) \right) \right\}$$

$$= \sum_{a} \sum_{i=1}^{N} \left\{ p_i(a) \left[ \sum_{k \neq i} p_{ik} D_m(\chi_i, \chi_k) \right] - \quad (8) \right.$$

$$\left. \sum_{j \in \Omega_i(a)} p_{ij} D_m(\chi_i, \chi_j) \right\}$$

In addition, the gradient of the alternative formulation, $\forall m$ is:

$$\frac{\partial f(\Lambda)}{\partial \lambda_m} = \sum_{a} \sum_{i=1}^{N} \left\{ \sum_{k \neq i} p_{ik} D_m(\chi_i, \chi_k) - \frac{\sum_{j \in \Omega_i(a)} p_{ij} D_m(\chi_i, \chi_j)}{p_i(a)} \right\} \quad (9)$$

$$= \sum_{a} \sum_{i=1}^{N} \left\{ \sum_{k \neq i} p_{ik} D_m(\chi_i, \chi_k) - \frac{\sum_{j \in \Omega_i(a)} p_{ij} D_m(\chi_i, \chi_j)}{\sum_{j \in \Omega_i(a)} p_{ij}} \right\}. \quad (10)$$

This is quite meaningful. Note that:

$$s_m^t = \sum_{i=1}^{N} \sum_{k \neq i} p_{ik} D_m(\chi_i, \chi_k).$$

This is the average distance for the nearest neighbor regardless of class labels. One can call it unconditioned shift, or heterogeneous shift. One may also note that:

$$s_m^c(a) = \sum_{i=1}^{N} \left\{ \frac{\sum_{j \in \Omega_i(a)} p_{ij} D_m(\chi_i, \chi_j)}{\sum_{j \in \Omega_i(a)} p_{ij}} \right\}.$$

This is the average distance for the nearest neighbor of the same class. One may call it conditioned shift, or homogenous shift. So, the gradient $$\frac{\partial f(\Lambda)}{\partial \lambda_m} = \sum_a \{s_m^t - s_m^c(a)\}.$$

It is quite intuitive that the maximum is obtained when the heterogeneous shift and the homogenous shift are equal, i.e., when the nearest neighbor actually has the same class label.

Note: in practice, one must be careful when computing the conditional shift, as the denominator may be zero, $p_i(a)=0$. In this case, the sample i does not have any neighbors that share the same attribute class as i. Therefore, one must replace the homogeneous shift for the individual sample by a radius of its neighborhood domain.

Thus far, it has been shown that DTW-based swing matching gives quite promising results for attribute recognition from swing comparison. Dynamic time warping (or DTW) is an appropriate method for swing matching, compared to uniform re-sampling, hidden Markov models, and dynamic Bayesian networks. DTW-based swing matching methods are able to give satisfactory performance for swing tagging, and may significantly outperform some human instructors; also, DTW can be combined with uniform re-sampling, and it sacrifices a bit performance for the benefit of speeding up the computation; (3) different definitions of the swing distance measure influence the results of DTW, and it is an open problem to best define the distance measure. It has also been shown that metric learning is able to fine tune and enhance the performance of swing matching. The best distance measure may be automatically learned from the tagged swing data, which is called metric learning in general. Considering the multi-modality nature of the spatial features of swings, a novel metric learning algorithm best balances and weighs these multiple modalities. The new metric learning algorithm is able to converge to local optima and is able to fine tune and improve the performance of swing matching.

Computing the dynamic time warping based matching 284 (DTW based matching 284) between two action sequences is computationally intensive. Note that for each query action, one must compute the DTW based matching 284 against all exemplars in the SKDB 276. When one uses a large number of action exemplars, DTW based matching 284 becomes computationally infeasible. The solution includes two submodules, lower-bound estimation 288 and branch and bound based sub-linear searching 290.

Lower-bound estimation 288 and branch and bound based sub-linear searching 290 are used because if one computes the similarity, or distance, between the query action (e.g. golf swing) and all the action exemplars in the SKDB 276 one by one, this linear search will not be feasible. However, one may use lower-bound estimation 288 combined with branch and bound based sub-linear searching 290 for a less computationally intensive and faster way to compare a query action, or swing, with exemplars in the SKDB 276. Thus, with the goal of designing a search method that is of a sub-linear complexity (i.e., faster than a linear search), the basic idea is to estimate the lower bound distance for all exemplars with respect to the query action and safely skip those with lower bounds larger than the current best candidate met in the searching process.

To achieve sub-linear searching, one must use lower bound estimation 288 and branch and bound based sub-linear searching 290 in the search algorithm. The basic idea is to compute a tight lower bound distance for matching, i.e., $$D_{LB} < D(x, y)$$

where x and y are the two swings, and the distance between x and y is always larger than its lower bound $D_{LB}$. This enables one to reduce the number of swings searched. If it is known that a similar swing will not have a distance to the query swing further than d, then those swings that have a distance beyond the lower-bound are already larger than d and can be safely pruned because the actual distances will never be smaller than the lower bound. So, for every swing in the database, one may compute the swing's lower-bound distance with respect to the query swing.

The branch and bound based sub-linear searching 290 maintains a priority queue of swings. Each time a query swing is received for comparison, an item is popped from the queue, and the actual distance is used as the threshold, which will be compared against the lower bounds of the swing candidates. Then we can prune those swings where the lower bounds are larger than this threshold. This process is iterated until the priory queue is empty.

The most important thing in this sub-linear search is the design of the lower bound. The lower bound must be computed with a minimum cost. If much computation is involved with the lower bound, then the benefits gained will not outweigh the overhead of computing the lower bound. Then, using the calculated lower bound will not speed up the search. The lower bound must be tight. If the bound is loose, i.e. it is a trivial lower bound, the lower bound will not improve the search speed noticeably.

In the described embodiments, the lower bound estimation 288 is computed via the low-resolution swing data. There are two steps: first, the Euclidean distance is calculated based on low-resolution data. Then, one must down-sample every swing into a number of bins, N (e.g., N=150), and simply use the $L_2$ norm to compute the distance between two swings, i.e., $D_{LR}(x, y)$; and second, a constant is subtracted from it to obtain the lower bound, i.e., $$D_{LB} = \max(0, D_{LR}(x, y) - t)$$

where the offset t can be learned from training data.

Continuing with FIG. 24, non-parametric classification 264 is based on the SKDB 276 and the SKDB search engine 278. The SKDB 276 represents our human knowledge in an implicit way. Searching the SKDB 276 exemplar database to find similar cases to the input naturally provides recognition results. When more exemplars are added to the SKDB 276, the knowledge grows naturally and the non-parametric classification 264 becomes more powerful. For an input query, after pre-processing for feature extraction, the SKDB Search Engine 278 finds a set of "similar" exemplars in SKDB 276, each of which has a set of annotated attributes. The non-parametric classification 264 schemes are based on these sets of matched exemplars. Five different schemes have been designed for this system: 1) 1-NN; 2) 1-NN-soft; 3) k-NN-vote; 4) ∈-NN-vote; and 5) mixed-NN; however, the mixed-NN scheme is generally used for action attribute classification.

The designs of non-parametric classifiers are based on nearest-neighbor (NN) rules. The schemes mentioned above may be used. In the 1-NN scheme, for an input swing X, the most similar swing Y in the exemplar database (SKDB) is retrieved. The input swing will be tagged as the same set of attributes of Y. The DTW distance, as described above, is used as the swing similarity measure. 1-NN-soft is similar to the 1-NN scheme. 1-NN-soft also retrieves the most similar swing Y in SKDB, and the input swing is tagged as the same set of attributes of Y, but the difference is that 1-NN-soft assigns a confidence level w(a) to the attribute a based on the distance of Y to the input X, i.e., d(X,Y). Here, $$w(a) = \begin{cases} \exp\left(-\dfrac{d^2}{2\sigma^2}\right), & \text{if } y \text{ has attribute } a \\ 0, & \text{otherwise} \end{cases}$$

if y has attribute a otherwise.
The further the distance, the weaker the confidence level.

The k-NN-vote scheme retrieves a k number of most similar swings $\{Y_1, \ldots, Y_k\}$ from SKDB. The tags of the input swing will be the integration of the tags of these k exemplars. The distance from the input X to an exemplar Y is $d_i(X, Y_i)$. Each exemplar can be viewed as a soft nearest neighbor, with probability p $$p_i = \dfrac{\exp(-d_i/s)}{\sum_j \exp(-d_j/s)}$$

where $s = \max_i(d_i)/3$. Each exemplar casts a vote of $v_i(a)$ on the attribute a it has, where $$v_i(a) = \begin{cases} \exp\left(-\dfrac{d_i^2}{2\sigma^2}\right), & \text{if } y \text{ has attribute } a \\ 0, & \text{otherwise} \end{cases}$$

if y has attribute a otherwise.
Then the confidence w(a) for an attribute a will be a weighted sum of these votes:

$$w(a) = \sum_i v_i(a) p_i.$$

It is clear that when k=1, this algorithm degenerates to 1-NN. Here k must be determined from use. A larger k will increase the false positive rate because it will bring some more irrelevant exemplars for voting.

The ∈-NN-vote scheme allows one to specify a distance range instead of specifying the number of nearest neighbors. One can specify a distance range ∈ and find all exemplars that fall into this range for voting. The parameter ∈ can be determined pragmatically through use. The rest of the scheme is the same as k-NN-vote.

In practice, it can be quite difficult to specify the best ∈. When a smaller ∈ is used, fewer exemplars, or even none, can be found; when a larger ∈ is used, more irrelevant exemplars will bring noise. Therefore, in an implementation, one may limit the maximum number of exemplar to be $k_{max}$.

In the mixed-NN scheme, one may combine the 1-NN and k-NN schemes. In this scheme, one uses a distance range parameter ∈. First, one can find the minimum distance $d_{min}$ of the input swing to the exemplar swings in SKDB. If $d_{min} > \epsilon$, then perform 1-NN-soft; otherwise, perform ∈-NN-vote.

In general, for designing and using non-parametric attribute recognizers, one may use the following conclusions: First, when using the exemplar database, non-parametric classifiers generally demand more memory. This scheme shifts the computation from training (as in parametric classification) to searching this exemplar database, so this scheme may be computationally intensive when the database is large. When new training data are added, unlike with parametric classifiers, the non-parametric classifiers do not have to be re-trained.

Second, if there is a large SKDB, non-parametric approaches may not be suitable for mobile devices, but non-parametric approaches can be a very good choice for building a remote attribute recognition server on the Cloud. Only one SKDB must be maintained, and the search can be parallelized on multiple processors.

Third, the design of non-parametric classifiers is based on the nearest neighbor classification. In this family of classifiers, the 1-NN-soft and k-NN-vote are reliable classifiers, mainly because it is easy to set and tune their parameters. But NN-vote and mixed-NN can be equally effective if good parameters can be tuned.

Thus far, the described embodiments have several connections among the components. First, to obtain a high-quality SKDB 276, one must integrate human intelligence from human 280 golf instructors and the machine intelligence coming from the SKDB search engine 278. Second, to provide high-quality accurate action matching, metric learning 286 is performed on the SKDB 276 and applied to the SKDB Search Engine 278. Third, to provide fast and efficient searches, lower-bound estimation 288 is performed to enable sub-linear search over the SKDB 276 via the branch and bound based sub-linear searching 290. Fourth, the SKDB search engine 278 provides accurate matching results via metric learning 286 applied to the dynamic time warping based matching 284 in a computationally efficient way via the branch and bound based sub-linear searching 290. Fifth, the SKDB Search Engine 278 provides a set of similar exemplar cases from the SKDB 276 to the non-parametric classification 264 module for attribute classification.

As a parallel path, described systems and methods include a parametric classification 266 component. The parametric classification 266 component takes a query action, e.g. swing data, as input and outputs the swing data attributes.

For any attribute, the recognizer needs to make a binary decision for an input swing, i.e., this attribute is present or not in this swing. This is a binary classification problem. To recognize a set of attributes, one may use a set of such binary classifiers for each individual attribute. A classifier can be either parametric or non-parametric.

A parametric classifier is based on a parametric discrimination model (i.e., a parametric function) where parameters are estimated or learned from the set of training data. Compared to the size of training data, the number of unknown parameters is small. Once trained, a parametric classifier does not need the training data anymore and can act by itself. Thus, parametric classifiers are generally compact for their size. But the training phase can be rather long and difficult. If a wrong parametric model is used, the performance can be very bad. In addition, parametric classifiers are difficult to adapt, as they must get re-trained with the long training process based on the new training data.

A nonparametric classifier is free-form but needs to maintain a set of exemplars. This set of exemplars implicitly represents the knowledge to be learned. The higher quality the exemplar database, the better the classification performance it has. The training of a nonparametric classifier may not be intensive, but it generally needs space to store its exemplar database. If the amount of memory is a concern, it is not appropriate to use non-parametric classifiers. As memory has become less of a concern, nonparametric methods are gaining popularity, mainly because of their flexibility and adaptability. When more exemplars are added in the database, the knowledge grows, and the classifier will improve its performance. In addition, the adaptation is naturally obtained by using new exemplars.

The major part of the parametric classification 266 component is the parametric classifier training 292, also known as the support vector machine 292, or SVM 292. In machine learning, support vector machines (SVMs, also support vector networks) are supervised learning models with associated learning algorithms that analyze data and recognize patterns, used for classification and regression analysis. Given a set of training examples, each marked for belonging to one of two categories, an SVM training algorithm builds a model that assigns new examples into one category or the other, making it a non-probabilistic binary linear classifier. An SVM model is a representation of the examples as points in space, mapped so that the examples of the separate categories are divided by a clear gap that is as wide as possible. New examples are then mapped into that same space and predicted to belong to a category based on which side of the gap they fall on. In addition to performing linear classification, SVMs can efficiently perform a non-linear classification using what is called the kernel trick, implicitly mapping their inputs into high-dimensional feature spaces. More formally, a support vector machine constructs a hyperplane or set of hyperplanes in a high-dimensional or infinite-dimensional space, which can be used for classification, regression, or other tasks. Intuitively, a good separation is achieved by the hyperplane that has the largest distance to the nearest training-data point of any class (so-called functional margin), since in general, the larger the margin, the lower the generalization error of the classifier.

To separate, or discriminate, two classes, an SVM finds an optimal class boundary that gives the minimum error rate while leaving the maximum margin for both classes. Thus, it may be easily generalized, and it is able to avoid over fitting the training data to the largest extent. Over fitting is a critical concern in machine learning. A classifier giving a low misclassification rate based on training data, but a high rate on unseen testing data, over fits the training data. An over fitted classifier is unable to generalize to testing data unseen. SVM integrates both classification performance and generalization and is very successful in many applications. Also, to achieve good performance of pattern recognition, in addition to the choice of pattern classifiers, a more critical issue is the use of the right feature. Wrong features never give good performance, even when using a super powerful classifier.

Given n labeled training samples $(x_1, y_1), \ldots, (x_n, y_n)$ with each sample $x_i \in R^d$ and its corresponding labels $y_i \in \{1, -1\}$, where n is the total number of training samples, the objective of a support vector machine (SVM) is to find a hyperplane $w \cdot x + b = 0$ with parameters w and b such that the largest distance between samples with different class labels can be achieved. The hyperplane's distance to the positive training samples is defined as d+ and its distance to the negative training samples is defined as d−. The margin between positive and negative training samples can be represented as the sum of d+ and d−. As it is clear that:

$$d_+ + d_- = \frac{2}{\|w\|}.$$

Maximizing the margin equals minimizing the $\|w\|^2$.

Considering the simplest case first, assume that the given labeled training samples are linearly separable. In this case, for each training sample:

$w \cdot x_i + b \geq 1$ for $y_i = 1$ $w \cdot x_i + b \leq -1$ for $y_i = -1$.

We can conduct the unified form for all the constraints $y_i(w \cdot x + b) - 1 \geq 0, \forall i.$ And the formulation of SVM can be written as:

$$\text{minimize} \quad \frac{1}{2} \|w\|^2$$
$$\text{s.t.} \quad y_i(w \cdot x + b) - 1 \geq 0, \forall i.$$

In practice, the dual function may be used for easier processing. For a given vector α of Lagrange multipliers, the minimizer of the objective function can be written as:

$$L(w, b, \alpha) = \frac{1}{2} \|w\|^2 - \sum_{i=1}^{n} \alpha_i y_i (w \cdot x_i + b) + \sum_{i=1}^{n} \alpha_i.$$

To obtain the optimal value of parameter w, we have:

$$\frac{\partial L(w, b, \alpha)}{\partial w} = w - \sum_{i=1}^{n} \alpha_i y_i x_i$$

which may lead us to:

$$w = \sum_{i=1}^{n} \alpha_i y_i x_i.$$

Similarly, we have:

$$\frac{\partial L(w, b, \alpha)}{\partial b} = -\sum_{i=1}^{n} \alpha_i y_i,$$

and, $$\sum_{i=1}^{n} \alpha_i y_i = 0.$$

So, the dual function can be written as:

$$q(\alpha) = \inf_{w,b} L(w, b, \alpha) = \sum_{i=1}^{n} \alpha_i - \frac{1}{2}\sum_{i=1}^{n}\sum_{j=1}^{n} \alpha_i \alpha_j y_i y_i (x_i \cdot x_j).$$

So, one may convert the original SVM objective function into its dual problem in the following way:

$$\text{maximize } q(\alpha) = \sum_{i=1}^{n} \alpha_i - \frac{1}{2}\sum_{i=1}^{n}\sum_{j=1}^{n} \alpha_i \alpha_j y_i y_i (x_i \cdot x_j)$$

$$s.t. \quad \begin{cases} \alpha \geq 0 \\ \sum_{i=1}^{n} y_i \alpha_i = 0 \end{cases}$$

where in the dual function, the constraints are much simpler. Though it is still a quadratic programming problem, it is much more solvable than the original formulation of SVM.

$\alpha_i$ is the Lagrangian multiplier for the constraint contributed by $\{x_i, y_i\}$, i.e., each sample has an $\alpha_i$. Notice that there is a set of inequality constraints on $\alpha$ in the dual function. As discussed before, one can identify the set of active inequality constraints, i.e., those where $\alpha_i > 0$. Based on the active constraints, a special set of $\{x_i, y_i\}$ can be identified. They are located on the margin and are called the support vectors.

As in the discriminant function, $$f(x) = w \cdot x + b = \sum_{i=1}^{n} \alpha_i y_i (x_i \cdot x) + b$$

for the non-support vectors, i=0, the discriminant function can only rely on the support vectors:

$$f(x) = w \cdot x + b = \sum_{x_i \in \{S.V.\}} \alpha_i y_i (x_i \cdot x) + b$$

which also indicate that the decision surface (i.e., the hyperplane) is fully determined by the "support vectors" that are located on the margin. And the hyperplane has nothing to do with nonsupport vectors.

Besides considering the linearly separable case, the concept of a slack variable may be used to handle mislabeled samples. The method introduces non-negative slack variables $\xi_i$, which measure the degree of misclassification of the given labeled data.

$$\begin{cases} w \cdot x_i + b \geq 1 - \xi_i, & \text{for } y_i = 1 \\ w \cdot x_i + b \leq -1 + \xi_i, & \text{for } y_i = -1 \\ \xi_i \geq 0 & \forall i \end{cases}$$

If an error occurs, $\xi_i > 1$. So, $\Sigma_{i=1}^{n} \xi_i$ is an upper bound of the number of misclassifications.

Similar to the linearly separable case, with introducing of the slack variable, the formulation of the SVM can be slightly altered to:

$$\text{minimize } f(w) = \frac{1}{2}\|w\|^2 + C\sum_{i=1}^{n} \xi_i$$

$$s.t. \quad \begin{cases} y_i(w \cdot x_i + b) - 1 + \xi_i \geq 0 \\ \xi_i \geq 0, \forall i \end{cases}.$$

Rewrite it into the Lagrangian form, $$L(w, b, \alpha, \mu) = \frac{1}{2}\|w\|^2 + C\sum_{i=1}^{n} \xi_i - \sum_{i=1}^{n} \alpha_i(y_i(w \cdot x_i + b) - 1 + \xi_i) - \sum_{i=1}^{n} \mu_i \xi_i.$$

And its derivatives are:

$$\frac{\partial L(w, b, \alpha, \mu)}{\partial w} = w - \sum_{i=1}^{n} \alpha_i y_i x_i, \Rightarrow w = \sum_{i=1}^{n} \alpha_i y_i x_i$$

$$\frac{\partial L(w, b, \alpha, \mu)}{\partial b} = -\sum_{i=1}^{n} \alpha_i y_i = 0, \Rightarrow \sum_{i=1}^{n} \alpha_i y_i = 0$$

$$C - \alpha_i - \mu_i = 0.$$

Considering the concept of slack variable $\xi_i$, the original formulation of the SVM can be converted into the following form, $$\text{maximize } q(\alpha, \mu) = \sum_{i=1}^{n} \alpha_i - \frac{1}{2}\sum_{i=1}^{n}\sum_{j=1}^{n} \alpha_i \alpha_j y_i y_j (x_i \cdot x_j)$$

$$s.t. \quad \begin{cases} 0 \leq \alpha_i \leq C \\ \sum_{i=1}^{n} \alpha_i y_i = 0. \end{cases}$$

To create nonlinear classifiers, the kernel trick is employed in an SVM. Instead of using the dot product, the kernel trick allows the algorithm to fit the maximum-margin hyperplane in a transformed feature space by using a nonlinear kernel function. The transformed feature space is highly dimensional or even of infinite dimension. While, the classifier is a hyperplane in the highly dimensional or infinite feature space, it may be nonlinear in the original input feature space. The kernel is related to the transform $\varphi(x_i)$ by the equation $$k(x_i, x_j) = \varphi(x_i) \cdot \varphi(x_j).$$

The commonly used kernels include:

Polynomial: $k(x_i, x_j) = (x_i \cdot x_j)^d$

Hyperbolic tangent: $k(x_i, y_j) = \tan h(\kappa x_i \cdot x_j + c)$

Gaussian radial basis function: $k(x_i, x_j) = \exp(-\gamma \|x_i - x_j\|^2)$, for $\gamma > 0$.

The major innovations of the parametric classification 266 include convolutional feature training 300, metric learning 298 for SVM 292, and active learning 296 for SVM 292.

Most parametric classification methods must represent data samples as feature vectors of the same dimension. Because the data samples for action sequences, such as a golf club swing, may have different time durations or lengths, it is not trivial to represent them in a vector space. A conventional solution is to extract a fixed number of features for baseline comparison. However, such ad hoc manually-tuned features may only be viable for attributes that can be roughly defined by the swing sensory data, like one-plane/two-plane attributes. Unfortunately, most of the attributes may not have this luxury.

Convolutional feature computing 300 is used to create the baseline action sequences, such as for golf swings, in the described embodiment. The basic idea is to select a set of N action exemplars, annotated or not, as the baselines. For an action, one computes the affinity of this action to every action exemplar. Each affinity is registered as a number. Then, by stacking the numbers, one gets an N-dimensional feature vector for the action.

The design of ad hoc, manually-tuned features not only needs knowledge of the data, but also knowledge of the existence of such features. It can be very difficult, if not impossible, to design such features. Thus, one must use a universal way for feature extraction. The feature extraction means used in the described embodiments involves convolutional feature computing 300, which is described as follows.

Suppose one can find a set of N swings to serve as the basis swings, denoted by $\{\beta_1, \ldots, \beta_n\}$. One can call this set of basis swings a dictionary. For each input swing X, one may compute its affinity to each of the basis swings:

$$y_i = \exp(-\text{distance}(X, B_i)) \forall i.$$

Then the collection of such distances to all basis swings gives a N-dimensional feature vector:

$$y = [y_1, \ldots, y_N]^T.$$

Here, only the distance between two swings is needed. When using DTW distance, the two swings do not have to be of the same length.

Such a convolutional feature vector actually gives the affinity of the input swing to all basis swings. Thus, the input swing can be implicitly represented by a dictionary of basis swings. This gives a universal feature representation. Naturally, the quality of the basis dictionary matters, but in practice learning an optimal dictionary can be very difficult, because it involves an NP-hard combinatorial problem.

In sum, regarding parametric recognizers, one may draw a number of conclusions. Parametric recognizers are generally compact and are not memory demanding. Once they are trained, their training data are not needed anymore. But their adaptation is not easy because they need to be re-trained. Each individual attribute is treated independently, and a binary classifier is dedicated to each attribute. In real situations, this parametric approach can be quite suitable for an end user stand-alone local application. For a golf swing recorded in the local mobile device, it is not necessary to transmit the swing data to a remote cloud; the attribute recognition task can be done on the local device. Finding good features is always desirable for classification. For some attributes, one may be able to design ad hoc features, e.g., the one-plane/two-plane attributes. But for most attributes, it can be very difficult to find effective ad hoc features. A good solution is to use the method of convolutional features. This method designates a set of swings as the dictionary of basis. Each swing is represented by its affinity to this set of basis swings. The performance of the recognition method using convolutional features may depend on the quality of the basis dictionary. In theory, finding an optimal basis dictionary should be very difficult, if not impossible, because it is an NP-hard combinatorial selection problem. In practice, heuristics may be used to obtain sub-optimal solutions, e.g., via swing basis pursuit.

Metric learning 298 for SVM 292 is used because different features may have different units, or be associated with different physical meanings, and thus, they play different roles in classification. It is desirable to find and to assign the weight factors for different features. This is done via metric learning 298 as described before with respect to metric learning 286 and the SKDB.

Active learning 296 for SVM 292 is used with human 294 because the training of the SVM-based parametric classification 266 demands a large set of annotated, or labeled, training cases, such as action data and its associated attributes. However, annotating such training cases is expensive and time consuming. This is the same difficulty mentioned for the non-parametric classification. Thus, the same technique used for active learning 282 with non-parametric classification 264 and human 280 is used for active learning 296 with parametric classification 266 and human 294.

Note that one support vector machine 292 must be trained per attribute. An SVM 292 tells whether or not a particular attribute is present in the queried action data. Once the SVM 292 classifier is trained, for a query action input, the set of a trained SVM 292 is applied to the action input, and the attributes are detected.

As described above, the motion attribute recognition system has two parallel channels for attribute classification, namely the SKDB 276 based non-parametric classification 264, and the SVM 292 based parametric classification 266. These two classification components can be singly used or integrated for more robust and reliable classification.

To integrate the two classifications, a component called classification fusion 268 is used to fuse the classification results from the two classifiers. The approach is based on linear weighting. For each action attribute, suppose the nonparametric classifier gives a nonparametric classification 264 (or detection) confidence as $x_{np}$, and the parametric classifier's confidence is $x_p$. Then the combined confidence is modeled as:

$$y = w_{np} x_{np} + w_p x_p$$

where the weights $w_{np} > 0$, $w_p > 0$ and $w_{np} + w_p = 1$.

The two weights may be manually specified in practice based on subjective assessment on the confidences, or preferences, or the prior results from the two classifiers. If one has no preference, one may use $w_{np} = w_p = \frac{1}{2}$.

The following shows a learning method to learn $w_{np}$ and $w_p$ via linear programming:

$$(w_{np}, w_p)^* = \arg\min_{(w_{np}, w_p)} \sum_{k=1}^{N} w_{np} x_{np}^k + w_p x_p^k = w_{np} \sum_{k=1}^{K} x_{np}^k + w_p \sum_{k=1}^{K} x_p^k.$$

$$s.t. \quad w_{np} + w_p = 1$$

$$w_{np} > 0, w_p > 0$$

where $x_{np}$ to the power of k and $x_p$ to the power of k are the classification confidences for the nonparametric classification 264 and the parametric classification 266 for the $k^{th}$ training sample, respectively. It can be easily solved.

The described embodiment provides both options for classification fusion 268 in the defined systems and methods.

The above described systems and methods provide an engine for analyzing golf swing motion data, for finding faults in a player's swing by detecting swing attributes deviated from baseline measurements, and for ranking the detected attributes based on commonness and statistical confidence level. Naturally, a computer application may provide an interface between the engine and the player who wishes to improve his or her golf swing and act as a virtual coach.

Figure 25B:
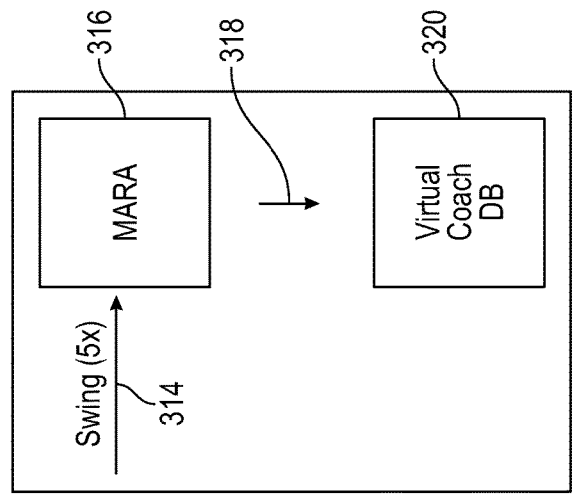
FIG. 25B shows a diagram of golf club swing data flow.
Figure 25A:
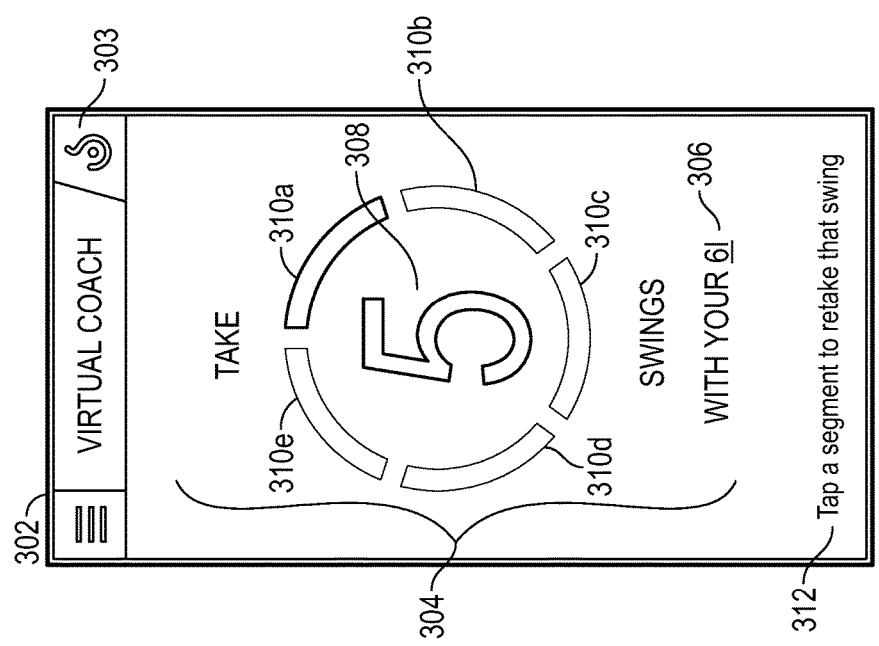
FIG. 25A shows a screen shot on a mobile electronic device of a virtual coach directing a user to swing the golf club.

FIG. 25A shows a screen shot on a mobile electronic device of a virtual coach directing a user to swing the golf club. When a player initiates the virtual coach on the mobile electronic device 302, the interface will present the player with a virtual coach instruction 304 telling the player what to do. In this example, the player is instructed to choose a 6 iron as the golf club 306 to swing and that the number of swings 308 that the player must take is 5. Before the player takes the first swing, the player may change the golf club 306 by selecting the area designating the golf club 306 on the screen. The virtual coach instruction 304 also includes swing selectors 310a-e. Swing selector 310a is shown highlighted to indicate that the player may tap the swing selector 310a to make the virtual coach wait for the player to swing a golf club and provide motion data for the engine to analyze. If the player does not like the swing chosen by swing selector 310a, then the retake message 312 lets the player know that the player may retake the swing by tapping swing selector 310a. This concept works for the other swing selectors 310b-e. In this example, once the player has taken five satisfactory swings, the swing data may be analyzed. The genius button 303 may be used to analyze a single swing instead of the average of the number of swings that the virtual coach tells the golfer to take.

FIG. 25B shows a diagram of golf club swing data flow. After the player takes five swings, the swing data 314 produced gets sent to an engine as described above, which may be referred to as a motion attribute recognition algorithms engine 316, or MARA 316. Once MARA 316 produces analyzed data 318, MARA sends the analyzed data 318 to a virtual coach database 320. In the described example, the individual swing data 314 for each of the five swings gets uploaded from the electronic device 302 and processed through MARA 316. The analyzed data 318 from each swing get stored in a virtual coach database 320 until all five swings are processed. Each result from the motion attribute recognition algorithms engine 316 consists of a set of faults, with the confidence level for each fault provided as a probability value between 0.0 and 1.0.

Once all the swings and faults are processed, the virtual coach will present a lesson plan to the player. FIG. 25C shows a screen shot on a mobile electronic device of a lesson plan for correcting top faults in the golf club swings. In this figure, the lesson plan title 322 is shown as "MY LESSON PLAN (6I)" to show the player that he or she is viewing a lesson plan based on swings of a 6 iron. While the lesson plan may include several lessons to improve the detected faults, screen space is limited, and only a limited number of lessons may be shown at a time. In FIG. 25C, each lesson in the lesson plan has a lesson number 324a-c. The top lesson number 234a is designated "LESSON 1". The middle lesson number 234b is designated "LESSON 2". The bottom lesson number 234c is designated "LESSON 3". Each lesson number 324a-c in the lesson with lesson plan title 322 displays a portion of a fault message 325a-c that indicates the detected faults to the player. Lesson number 324a, or "LESSON 1" shows a partial fault message 325a stating, "Your right elbow is leading and . . . ". This message discloses that the player's fault involves the attribute of leading with the right elbow. Lesson number 324b, or "LESSON 2" shows a partial fault message 325b stating, "You are raising your spine and t . . . ". This message discloses that the player's fault involves the attribute of raising the spine. Lesson number 324c, or "LESSON 3" shows a partial fault message 325c stating, "Your arms are swinging down t . . . ". This message discloses that the player's fault involves the attribute of swinging one's arms. The numbered lessons have lesson option buttons 326a-c that allow the player to see a lesson summary pertaining to that particular lesson and to access other options, such as video drills. The video drills associated with each lesson may be accessed using the drill video selectors 332a-c. The lesson plan also shows the swing score 330 as "50" for the set of swings associated with the shown lesson plan.

In the lesson plan shown for the described embodiments, the top faults are listed in order. Top faults are determined by first filtering their confidence scores to ignore faults with a confidence level below a certain threshold. For example, faults that have a confidence level below 0.5 are ignored. The remaining faults are then sorted and shown in a scroll-down fashion first sorted by part of swing in the following order: 1) impact & follow-through; 2) downswing faults; 3) backswing faults; and 4) address faults. Within each part of swing, the lessons are sorted by decreasing confidence level. In some embodiments, the number of lessons that a player may scroll through in a lesson plan may be limited. In the described embodiment, only the first N faults are shown and these are considered to be the top faults. In the described embodiment, N equals 5.

Selecting a fault from the lesson plan screen presents the fault view. The fault view presents a text and video description of the fault and a list of drills that can be used to improve the swings.

FIG. 25D shows a screen shot on a mobile electronic device of a lesson summary in text form and interchangeable with a lesson summary in video form. The mobile electronic device 302 shows the fault 333 listed at the top and a lesson summary 334 associated with the lesson selected within the lesson plan from the virtual coach. Once the player reads the lesson summary 334, the player may switch to the video drills screen 337 by pressing the screen swap button 336, where the player may watch videos to see how the swing may improve. Optionally, the player may also press the work on fault button 338 to reach a feedback screen that measures progress.

Figures 25E, 25F:
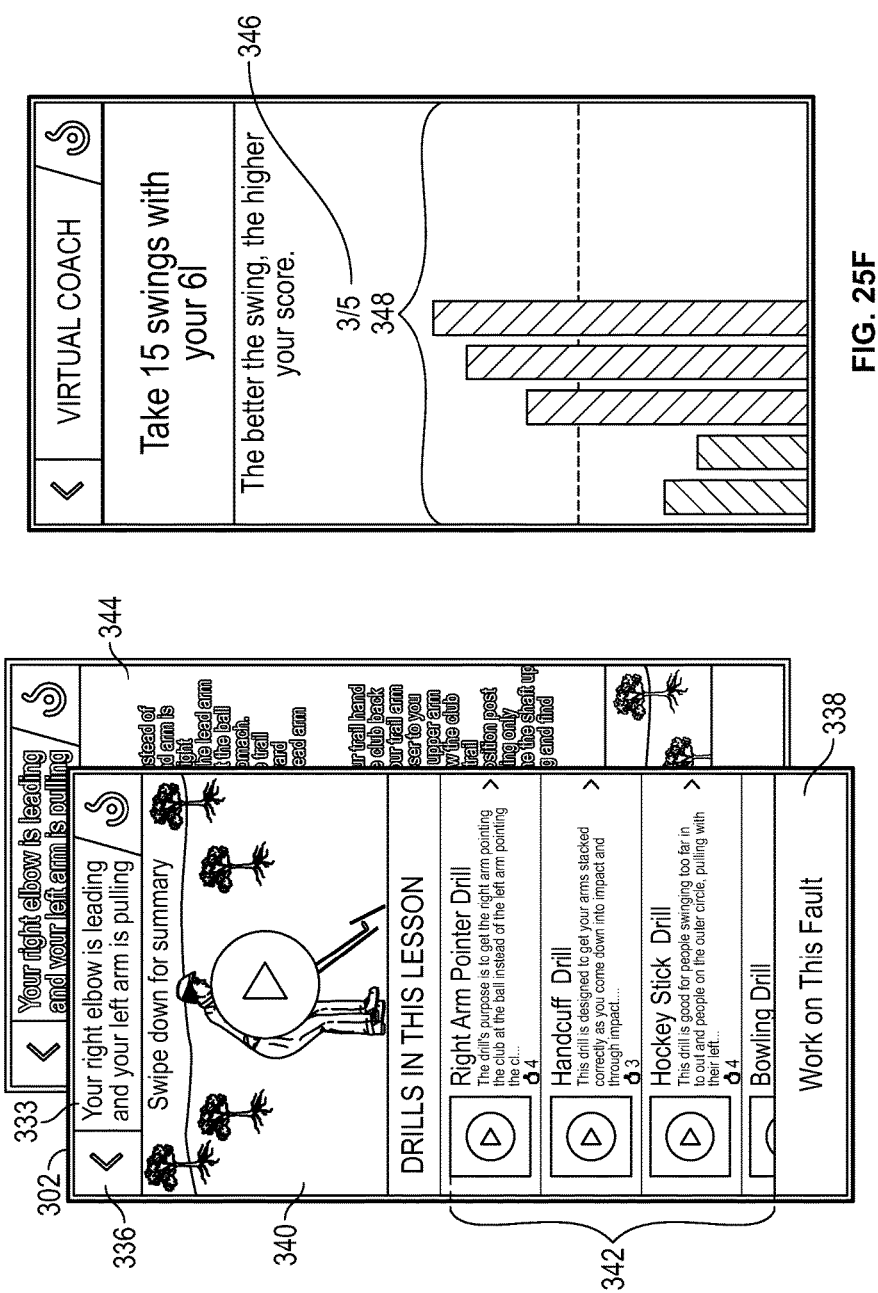
FIG. 25E shows a screen shot on a mobile electronic device of a lesson summary in video form and interchangeable with a lesson summary in text form.
FIG. 25F shows a fault progress view.

FIG. 25E shows a screen shot on a mobile electronic device of a lesson summary in video form and interchangeable with a lesson summary in text form. The mobile electronic device 302 shows the fault 333 listed at the top with a video display 340 directly below the listed fault 333. The video drill list 342 directly below the video display 340 provides a scrollable list of selectable videos for the player to watch on the video display 340 to improve his or her swing. The player may press the screen swap button 336 to switch back to the lesson summary screen 344, which is the screen shown in FIG. 25D. Also as in the screen shown in FIG. 25D, the player may press the work on fault button 338 to reach a feedback screen that measures progress.

FIG. 25F shows a fault progress view. Selecting "work on this fault" from the previous screen puts the user in a feedback screen. Each swing taken generates a bar, the height of which is determined by how much improvement is present against a fault. Improvement is determined as follows: 1) the main swing characteristics of face, path, angle of attack, lean, loft of the original 5 swings are averaged and recorded; 2) each fault has associated with it a ball flight that it generates; 3) each ball flight has associated with it a parameter and directional change that improves or worsens it; 4) the numerical change in those parameters relative to the 5 swing baseline determines the score, and the score is biased to 50 as no change, and constrained to [0, 100]. FIG. 25F shows that the player worsened after the first five swings but then increasingly improved. The improvement indicator 346 shows that the player improved during 3 of 5 swinging sessions. The bar graph 348 displays a level of achievement over a period of time.

Figure 25G:
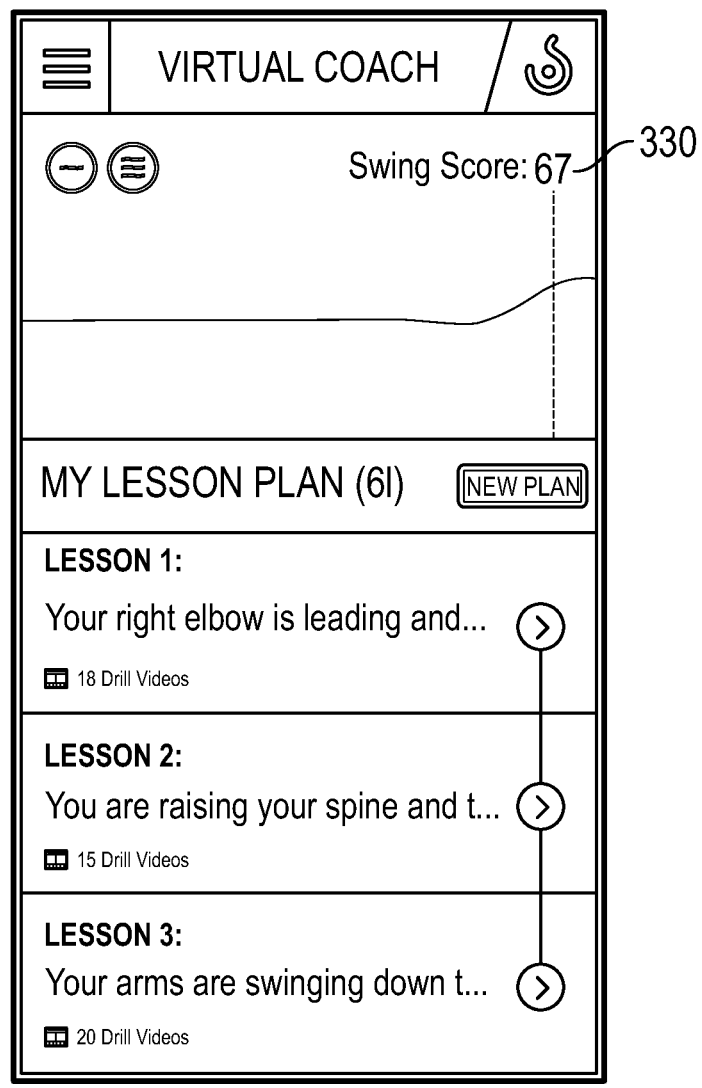
FIG. 25G shows a screen shot on a mobile electronic device of an improved score while following the lesson plan.

FIG. 25G shows a screen shot on a mobile electronic device of an improved score while following the lesson plan. In FIG. 25C, the player's swing score 330 was shown as 50, and now, after lessons, FIG. 25G shows the player's swing score 330 as 67. The player has thus received value from the lessons.

Figure 26:
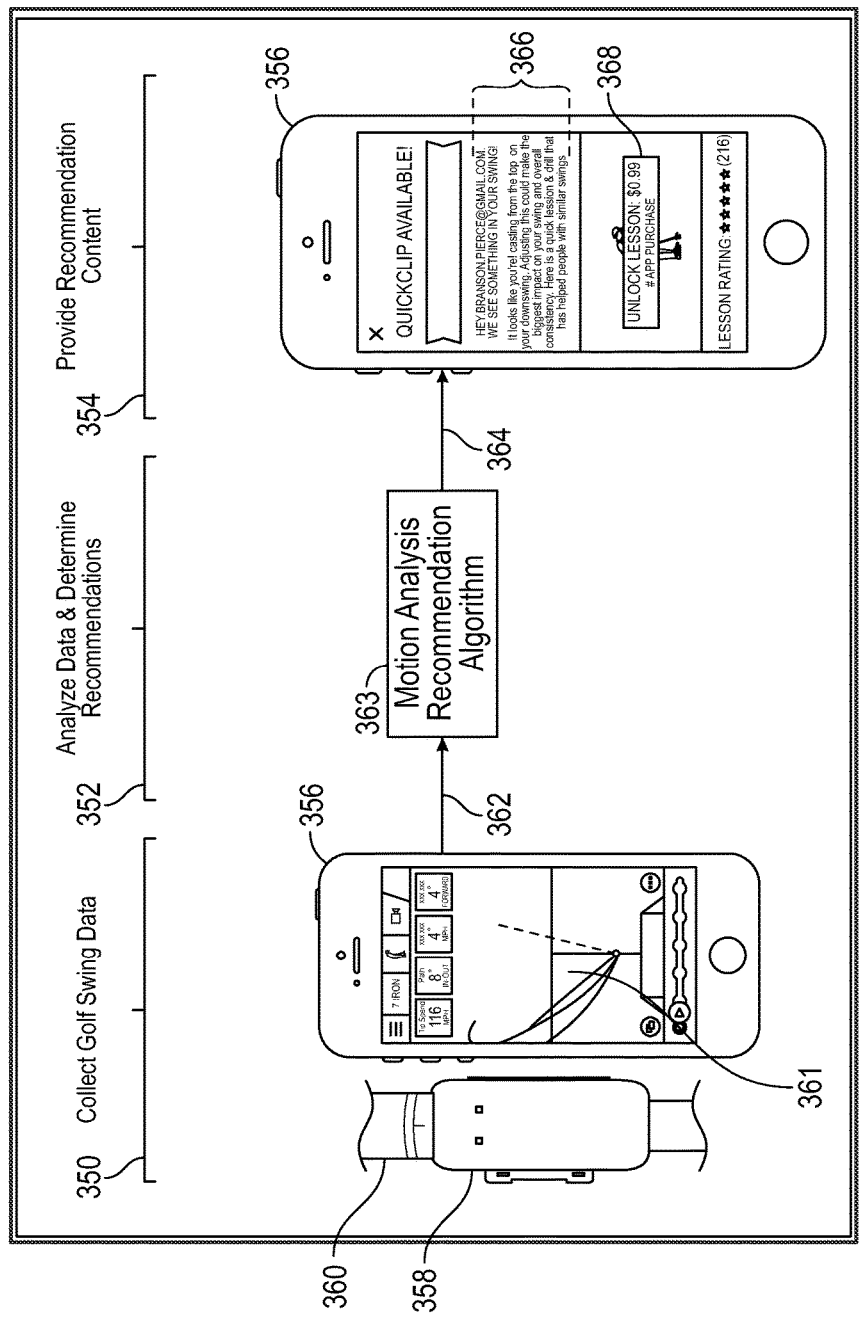
FIG. 26 shows how analyzing swing data may be used to market lessons.

FIG. 26 shows how analyzing swing data may be used to market lessons. This figure shows a three step process where first, the player uses the motion measurement device 358 to collect golf swing data in step 350; second, the player uses the motion data analyzer 363 to analyze data and determine recommendations in step 352; and third, the player receives an ad for a service to provide recommended content in step 354. In step 350, the player swings a golf club, which has the motion measurement device 358 attached to the golf club shaft 360. The mobile electronic device 356 collects the golf swing data and shows the animated swing 361 on the display. Next, the data transfer 362 sends the data from the swing motion to the motion data analyzer 363 so that the motion data analyzer 363 can analyze the data and determine recommendations, and then, the data transfer 364 sends the processed data back to the mobile electronic device 356. Lastly, in step 354, the mobile electronic device 356 is provided the recommendation content, which is shown on the display as a personalized message 366 and a lesson promotion 368.

Figure 27:
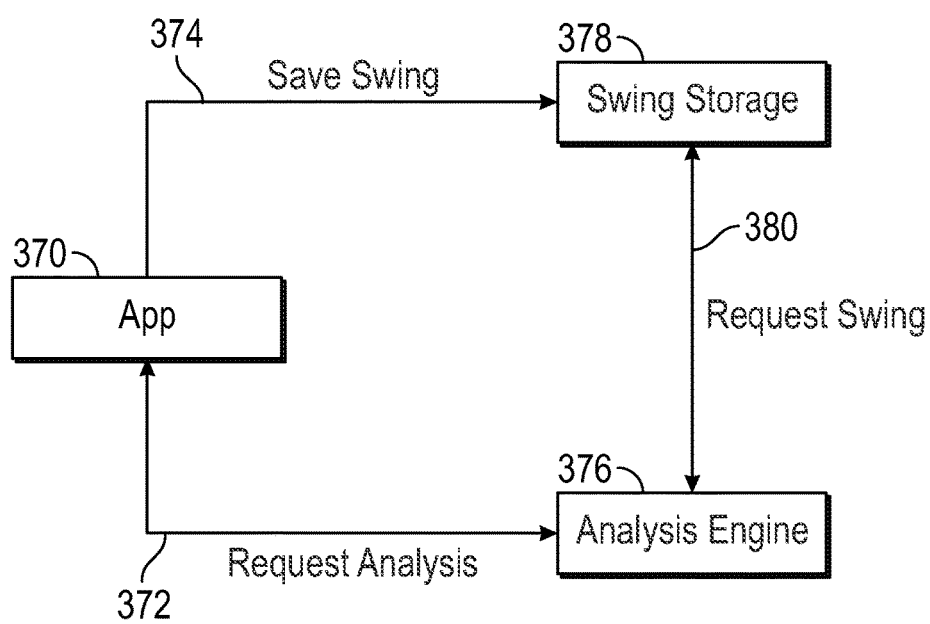
FIG. 27 shows a swing sent for present analysis and to storage for future analysis.

FIG. 27 shows a swing sent for present analysis and to storage for future analysis. In this figure, an application 370 running on an electronic device gathers data and does two things. One, the application 370 requests analysis of the motion data in sending a request analysis 372 message to the analysis engine 376, and two, the application 370 requests that the motion data be sent to swing storage 378 with a save swing 374 request. Meanwhile, the analysis engine 376 makes a request swing 380 message to the swing storage 378 so that the swing storage 378 will send comparison swing data to the analysis engine 376 to compare with the motion data sent from the application 370. The motion data sent from the application 370 with the save swing 374 request may be used for later comparisons when the analysis engine 376 later sends a request swing 380 message to the swing storage 378.

Figure 28A:
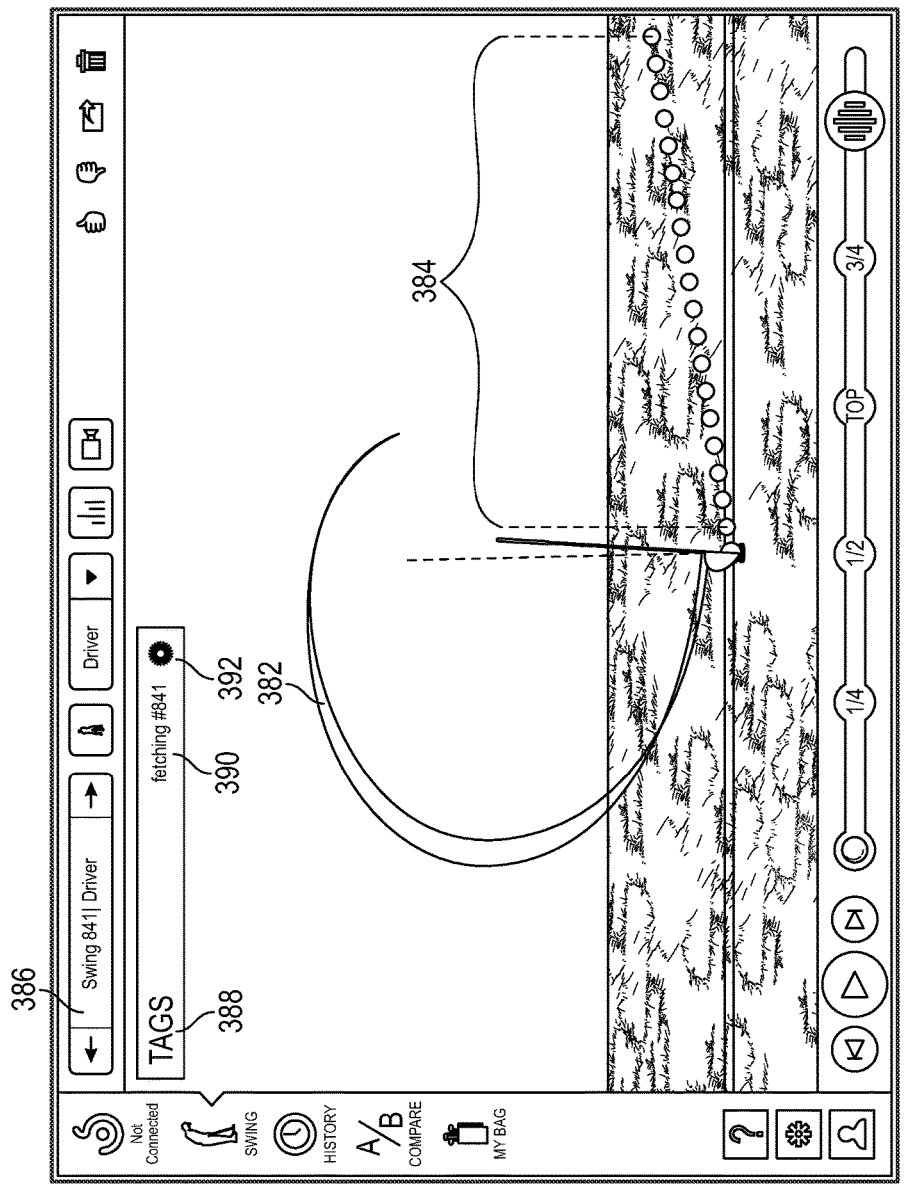
FIG. 28A shows animation for a stored swing with the system fetching faults.
Figure 28B:
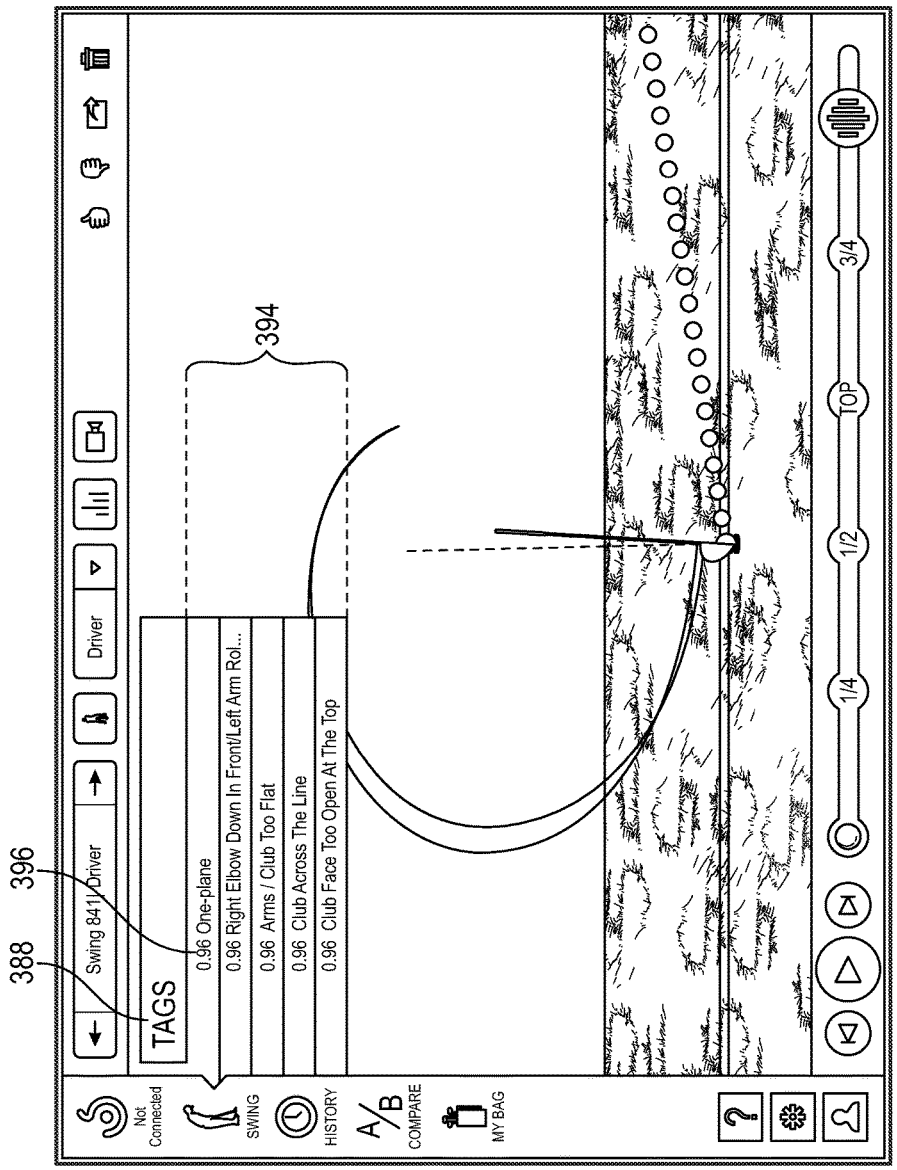
FIG. 28B shows animation for the stored swing of FIG. 28A with the fetched faults.

FIG. 28A shows animation for a stored swing with the system fetching faults. The animated swing 382 is shown on the display along with the simulated ball flight 384. The animated swing 382 may represent an old, saved swing or a swing that the player just took but that has been saved and given a swing number 392. The swing status bar 386 shows that the subject swing is currently swing number 841, which used a driver. The tags bar 388 shows that current data status 390, which informs the player that data is being fetched for swing #841 as shown in the swing number 392. FIG. 28B shows animation for the stored swing of FIG. 28A with the fetched faults. The tags bar 388 no longer shows data fetching and instead shows a drop-down list of swing faults 394 that includes the first five detected swing faults 394 in swing number 841. Note that the confidence level 398 is shown preceding the swing fault 394 designation.

Figure 28C:
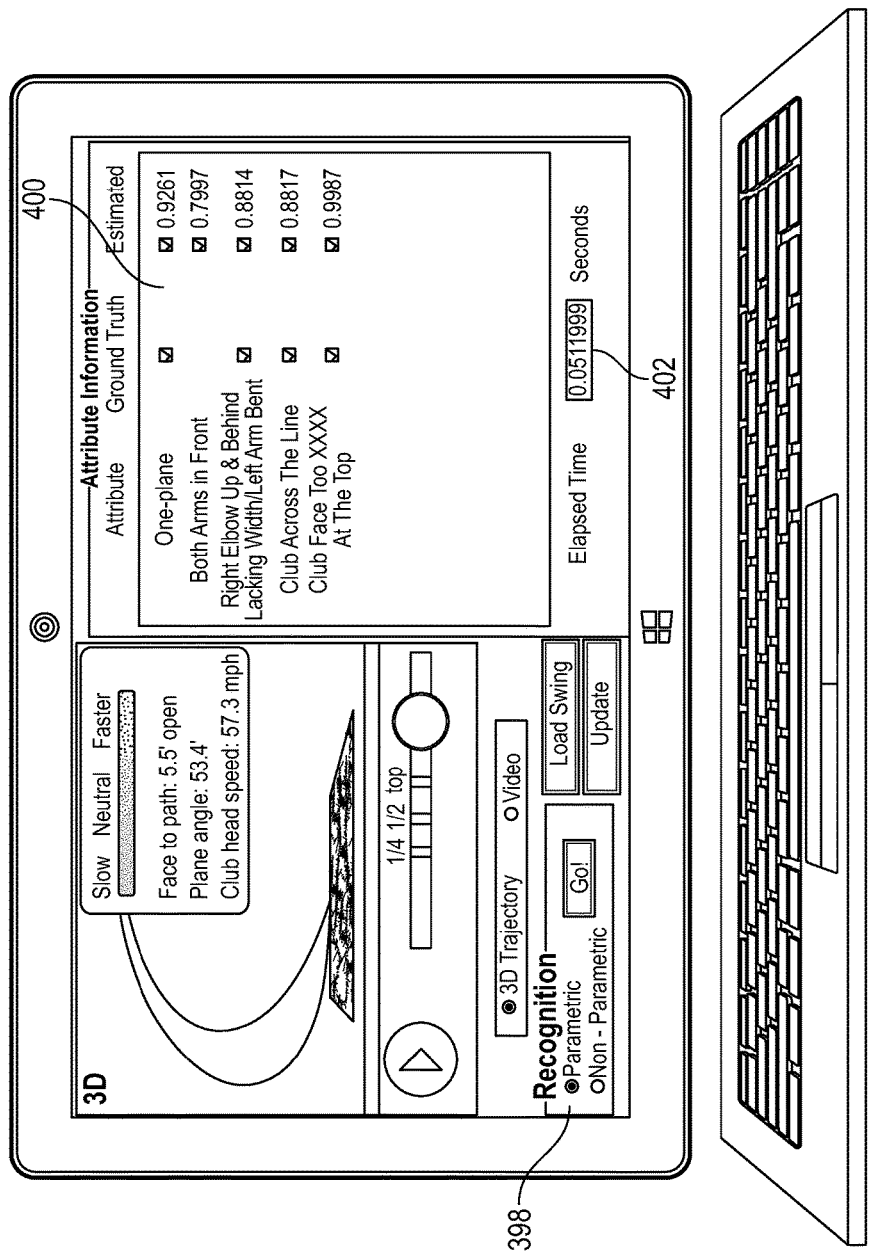
FIG. 28C shows a screen shot of a sample layout for the virtual coach to present a swing with 3D animation and fault information using parametric classification.

FIG. 28C shows a screen shot of a sample layout for the virtual coach to present a swing with 3D animation and fault information using parametric classification. In this layout, a recognition classification box 398 shows that parametric classification was used to detect the faults in the sample golf swing. The attribute information box 400 shows the top five faults and notes which fault detections match ground truth measurements estimated with a confidence level. That is, the ground truth measurement indicates that a human has analyzed the swing shown and that, based on the stored data in the system, which includes ground truth measurements from other humans, there is a 92.61% confidence level that the presence of the attribute is correct. For example, the motion attribute recognition algorithms characterization of the shown swing as a one-plane swing is made at a 92.61% confidence level. In described embodiments, this screen will be used to provide feedback during the parametric training process.

Another interesting thing shown in the attribute information box 400 is that the fault, or attribute, of "Right Elbow Up & Behind Lacking Width/Left Arm Bent" indicates that the described systems and methods can identify faults of the body using only data produced by the golf club. Also note that the elapsed time indicator 402 shows that the parametric search for the shown attributes took very little time.

Figure 28D:
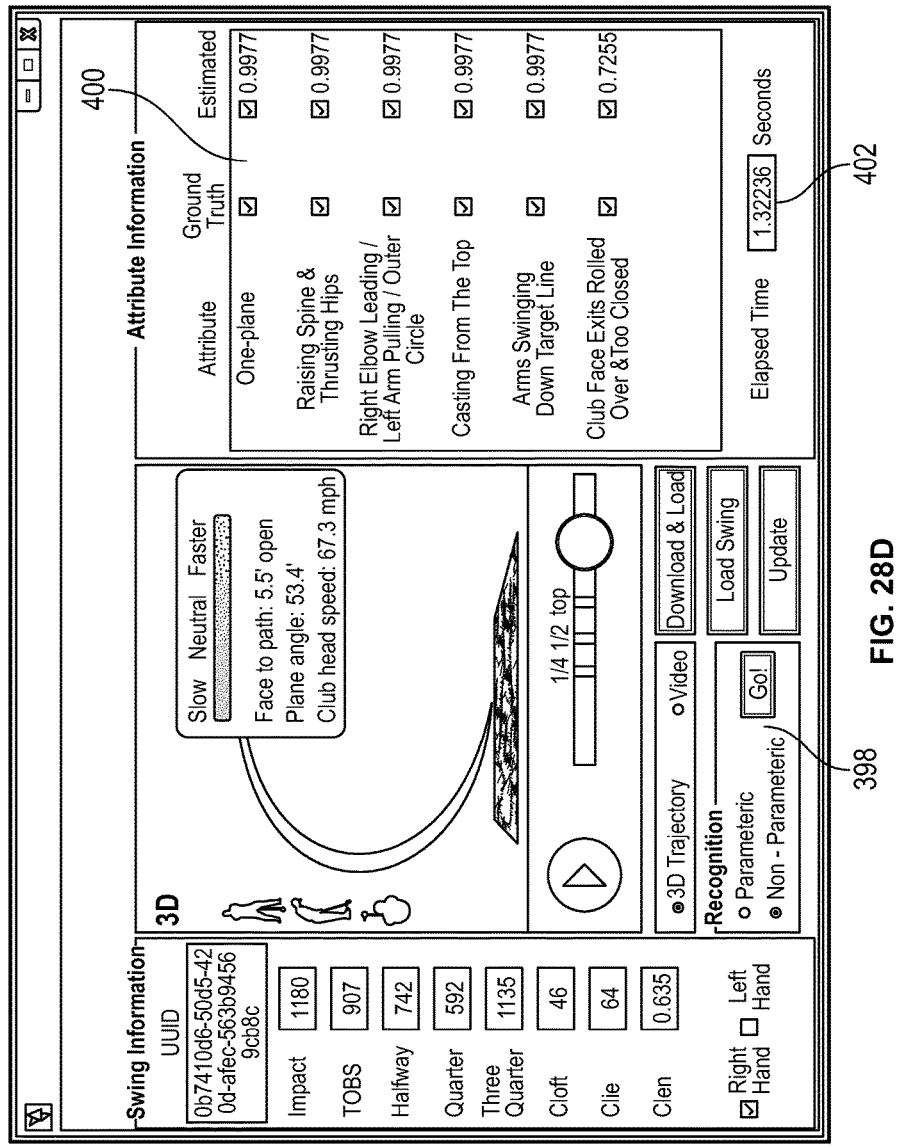
FIG. 28D shows a screen shot when using non-parametric classification and a 3D trajectory animation.

FIG. 28D shows a screen shot of a sample layout for the virtual coach to present a swing with 3D animation and fault information using non-parametric classification. In this figure the recognition classification box shows that non-parametric classification was used to detect the faults in the sample golf swing. The attribute information box 400 shows greater confidence levels for the non-parametric classification, and the elapsed time indicator 402 shows a greater time needed to detect the listed faults.

Figure 28E:
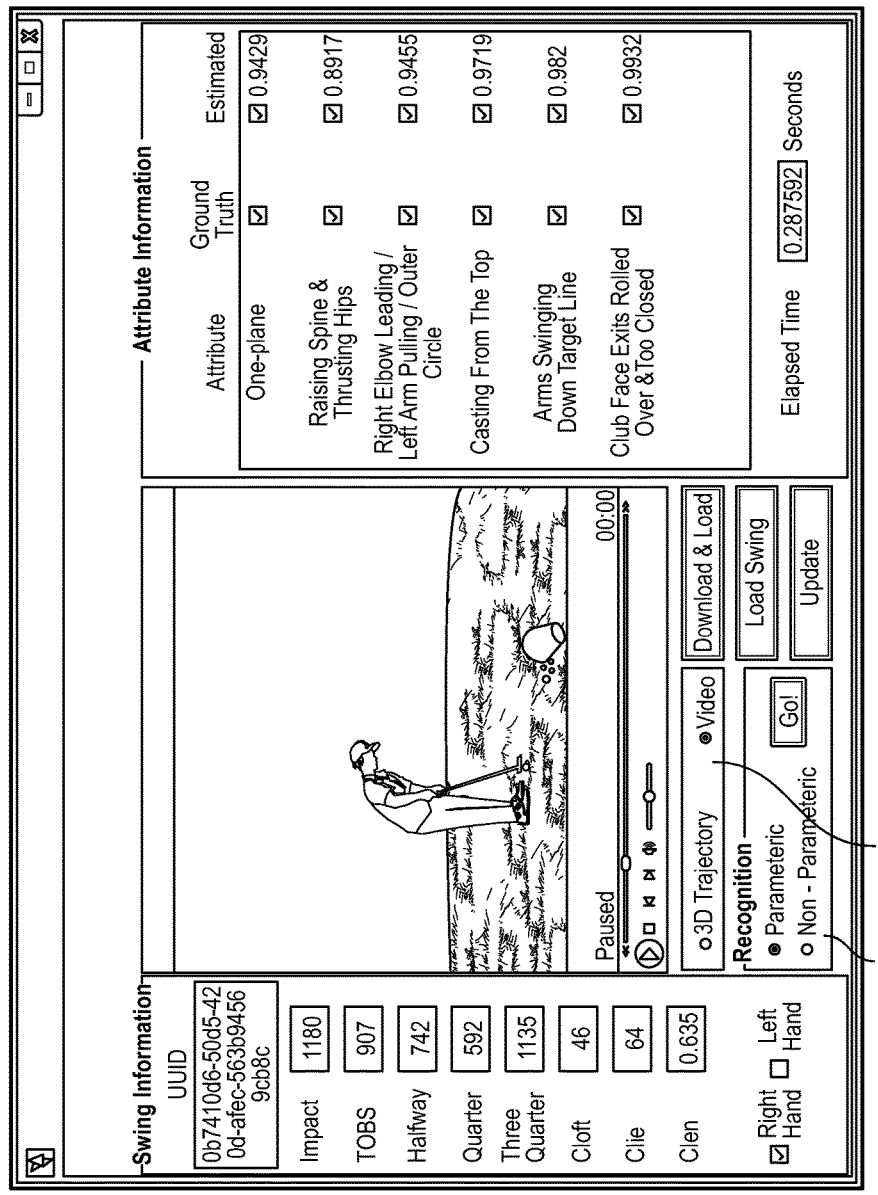
FIG. 28E shows a screen shot using parametric classification and a video reached by making selected changes to the screen in FIG. 28D.

FIG. 28E shows a screen shot using parametric classification and a video reached by making selected changes to the screen in FIG. 28D. This figure shows the flexibility of the shown interface where the player may switch back and forth between different views and different classifications simply by making a click selection in the recognition classification box 398 or the swing view selection box. This flexibility may help the player see the indicated faults in the video and correlate the fault with a part of the animation.

Figure 28F:
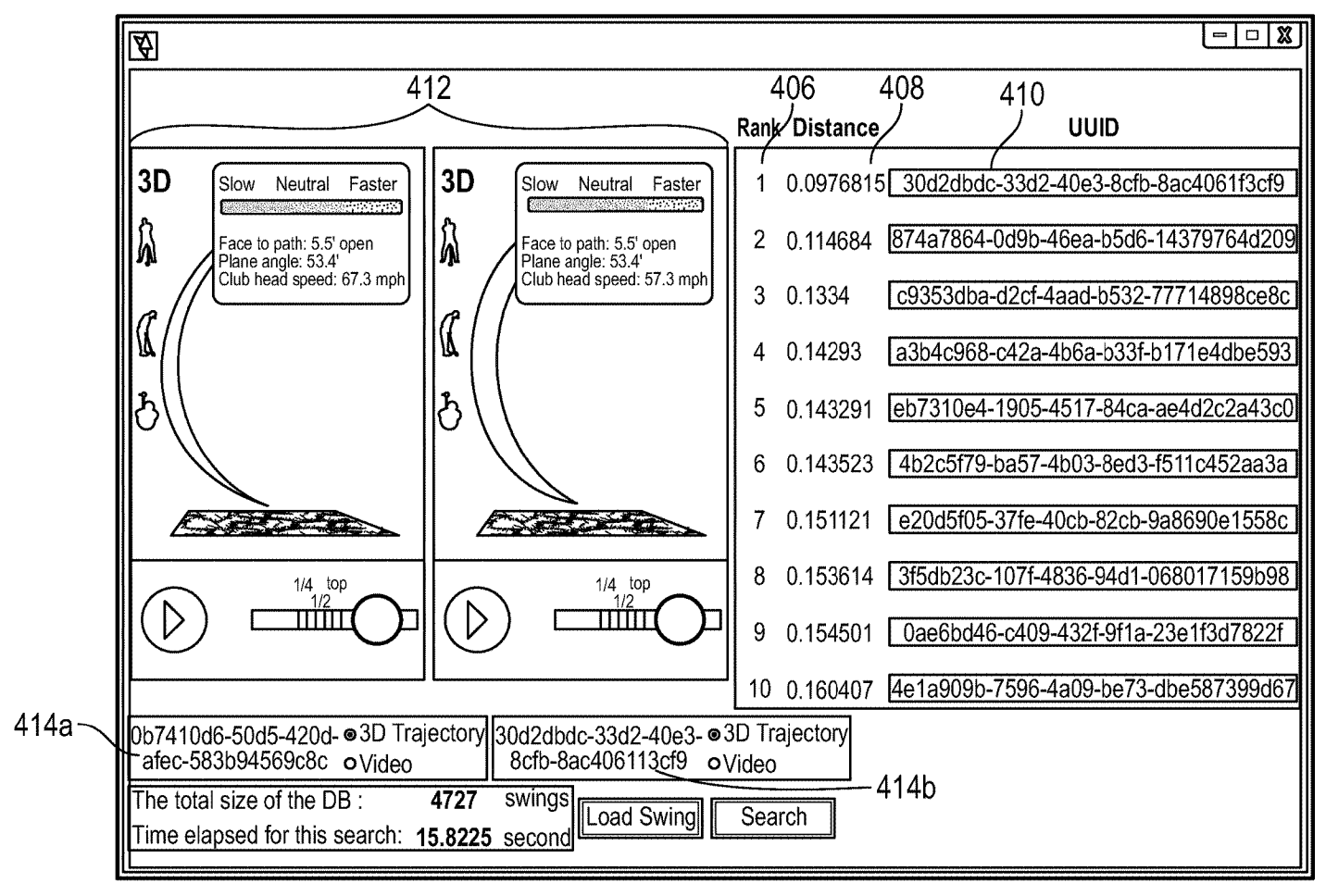

FIG. 28F shows a screen shot for showing a swing animation and the top ten matches from the stored swings database. The top ten matches are listed according to rank 406 of the distance 408 between the swing just recorded and the matched swing, calculated via DTW as described above or some other similar calculation. The swing ID number 410 is shown and selectable to compare one of the matched swings with the swing just recorded in a side by side double window view 412. In FIG. 28F, the side by side comparison is shown as a 3D animation. Note that the swing just recorded is shown on the left and the swing with rank 406 number 1 show the same statistics, except for the club head speed. A player may also compare the detected faults of similar swings for information that may help with improvement. The ID of the recent swing 414a is shown below the animation box showing the recent swing animation, and the ID of the compared swing 414b is shown below the animation box showing the compared swing animation.

Figure 28G:
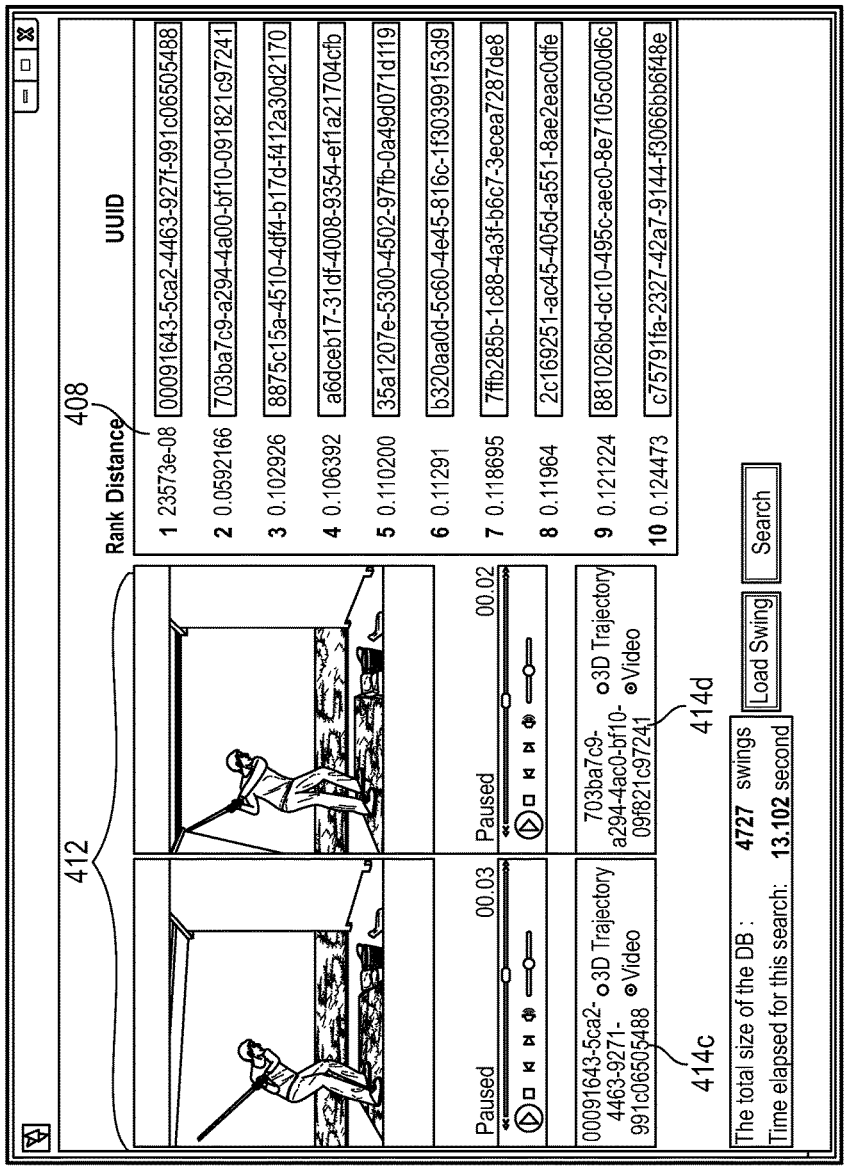
FIG. 28G shows a screen shot for showing a swing video and the top ten matches from the stored swings database.

FIG. 28G shows a screen shot for showing a swing video and the top ten matches from the stored swings database. In this figure, the player has changed from animation view to video view in the double window view 412 and video relating to the ID of the first stored swing 414c is now compared with the video relating to the second stored swing 414d. Note that the distance 408 of the swing on the left to itself is virtually 0.

The following table shows sample rules for fault improvement progress:

|  | loft | face: path | lean |
|---|---|---|---|
| high steep |  |  |  |
| high shallow | decreasing 0.15 |  | increasing 0.15 |
| low shallow |  |  |  |
| low trap | increasing 0.4 |  | decreasing 0.4 |
| hook |  | increasing 0.2 |  |
| Pull |  |  |  |
| push |  |  |  |
| slice |  | decreasing 0.2 |  |
| heel/shank |  |  |  |
| chop, chunk & pop-up |  |  |  |
| fat & thin |  |  |  |
| steep top |  |  |  |
| shallow top |  |  |  |
| missed radius top |  |  |  |

|  | aoa | path | lie/shaft angle |
|---|---|---|---|
| high steep | decreasing 0.7 |  | decreasing 0.3 |
| high shallow | increasing 0.35 | decreasing 0.35 |  |
| low shallow | increasing 0.5 | decreasing 0.5 |  |
| low trap | decreasing 0.2 |  |  |
| hook |  | decreasing 0.8 |  |
| pull |  | increasing 1 |  |
| push |  | decreasing 1 |  |
| slice |  | increasing 0.8 |  |
| heel/shank |  | decreasing 0.2 | decreasing 0.8 |
| chop, chunk & pop-up | decreasing 0.8 | increasing 0.2 |  |
| fat & thin | increasing 0.2 | decreasing 0.8 |  |
| steep top | decreasing 0.8 | increasing 0.2 |  |
| shallow top | increasing 0.2 | decreasing 0.8 |  |
| missed radius top |  |  | increasing 1 |

For each ball flight listed, each column shows what direction the given parameter must move to constitute an improvement. For example, "high steep" ball flights want angle of attack (aoa) to decrease and lie/shaft angle to decrease to constitute an improvement. The numbers in the thin columns are weights given to each parameter. If a characteristic in one column is more important that a characteristic in another column for the same row, then the weight of the more important characteristic will be greater than the weight of the other characteristic. Thus, the formula for "high steep" is 0.7*(angle of attack decreasing) and 0.3*(lie angle decreasing).

While the present inventions have been illustrated by a description of various embodiments and while these embodiments have been set forth in considerable detail, it is intended that the scope of the inventions be defined by the appended claims. It will be appreciated by those skilled in the art that modifications to the foregoing preferred embodiments may be made in various aspects. It is deemed that the spirit and scope of the inventions encompass such variations to be preferred embodiments as would be apparent to one of ordinary skill in the art and familiar with the teachings of the present application.

What is claimed is:

1. A motion attribute recognition system comprising:
   a pre-processing component configured to receive a data stream including motion data and to output action exemplars comprising:
   an orientation matrix conversion process configured to transform raw motion data into a quaternion suitable to measure the distance between two rotations by comparing the quaternion of a one rotation with the quaternion of the other rotation;
   a spatial alignment process configured to align the starting plane of the motion data; and
   a temporal segmentation process configured to locate the actual segment of the motion data within the data stream;
   a non-parametric classification recognition component in communication with the pre-processing component comprising:
   a database of stored action exemplars searchable to and configured to output motion attributes from a query comprising the motion data;
   a database search engine configured to search the database of action exemplars for comparison with a received action exemplar from the pre-processing component; and
   a non-parametric classification recognition process configured to receive action exemplars from the pre-processing component and the database search engine and to output attributes of the action exemplar received from the pre-processing component; and
   a parametric classification recognition component in communication with the pre-processing component comprising:
   one or more support vector machines wherein each support vector machine is configured to find one of the presence and absence of an attribute in an action exemplar received from the pre-processing component; and
   a parametric classification recognition process configured to receive an action exemplar from the pre-processing component and to query the one or more support vector machines for the presence of an attribute in the action exemplar and to output one of the presence and absence of an attribute in the action exemplar;
   a display; and
   an user interface in communication with the database and the display and configured to receive the motion data, to query the database with the motion data, to receive attributes from the database in response to the query, and to output attribute information on the display in order to present a virtual coach.

2. The motion attribute recognition system of claim 1, further comprising a classification fusion process to integrate the non-parametric classification recognition process and the parametric classification recognition process by fusing the results from the classification recognition processes based on linear weighting.

3. The motion attribute recognition system of claim 1, wherein the non-parametric classification recognition process further comprises the database search engine configured to compare the received action exemplar from the pre-processing component with the action exemplars in the database of stored action exemplars by measuring the distance between the two action exemplars with dynamic time warping based matching.

4. The motion attribute recognition system of claim 3, further comprising a metric learning component configured to optimize the distance between the two action exemplars.

5. The motion attribute recognition system of claim 1, further comprising an active learning component configured to receive human annotations marking attributes tagged to the stored action exemplars and in communication with the database search engine and further configured to spot inconsistencies in the human annotation tags marking attributes, to identify typical patterns in stored action exemplars with data clustering and to identify stored action exemplars at data cluster boundaries to suggest for further annotation tagging.

6. The motion attribute recognition system of claim 1, further comprising the database search engine configured to use lower bound estimation to estimate the lower bound distance for all exemplars with respect to the received action exemplar and to safely skip searching the database for action exemplars with lower bounds larger than the current estimated the lower bound distance met in the searching process.

7. The motion attribute recognition system of claim 6, further comprising the database search engine configured to use branch bound and bound based sub-linear searching.

8. The motion attribute recognition system of claim 1, further comprising an active learning component configured to receive human annotations marking attributes in parametric training case data and in communication with the parametric classification recognition process and the one or more support vector machines respectively, to receive parametric training case data, to add human annotations, to save the annotated training case data, and to spot inconsistencies in the human annotations.

9. The motion attribute recognition system of claim 1, further comprising a metric learning component configured to find and to assign different weight factors for different attributes present in the support vector machines.

10. The motion attribute recognition system of claim 1, further comprising a convolutional feature computing process in communication with the one or more support vector machines and the parametric classification recognition process and configured to extract attributes from action exemplars using convolutional feature computing.

11. A virtual golf coaching system comprising:
a first electronic device attachable to a golf club that transmits motion data from a swinging golf club describing the golf club movement; and
a second electronic device comprising:
a display;
a motion attribute recognition system comprising a database of stored golf swing exemplars searchable to and configured to output golf swing attributes from a query comprising the motion data; and
an application in communication with the first electronic device, the database and the display and configured to receive the motion data transmitted from the first electronic device, to query the database with the motion data, to receive attributes from the database in response to the query, and to output attribute information on the display;
a pre-processing component configured to receive a data stream including the motion data and to output golf swing exemplars comprising:
an orientation matrix conversion process configured to transform raw motion data into a quaternion suitable to measure the distance between two rotations by comparing the quaternion of a one rotation with the quaternion of the other rotation;
a spatial alignment process configured to align the starting plane of the motion data; and
a temporal segmentation process configured to locate the actual segment of the motion data within the data stream;
a non-parametric classification recognition component in communication with the pre-processing component comprising:
the database of stored golf swing exemplars;
a database search engine configured to search the database of stored golf swing exemplars for comparison with a received golf swing exemplar from the pre-processing component; and
a non-parametric classification recognition process configured to receive golf swing exemplars from the pre-processing component and the database search engine and to output attributes of the golf swing exemplar received from the pre-processing component; and
a parametric classification recognition component in communication with the pre-processing component comprising:
one or more support vector machines wherein each support vector machine is configured to find one of the presence and absence of an attribute in a golf swing exemplar received from the pre-processing component; and
a parametric classification recognition process configured to receive a golf swing exemplar from the pre-processing component and to query the one or more support vector machines for the presence of an attribute in the golf swing exemplar and to output one of the presence and absence of an attribute in the golf swing exemplar.

12. The virtual golf coaching system of claim 11, further comprising a classification fusion process to integrate the non-parametric classification recognition process and the parametric classification recognition process by fusing the results from the classification recognition processes based on linear weighting.

13. The virtual golf coaching system of claim 11, further comprising:
the non-parametric classification recognition process further comprising the database search engine configured to compare the received golf swing exemplar from the pre-processing component with the golf swing exemplars in the database of stored golf swing exemplars by measuring the distance between the two golf swing exemplars with dynamic time warping based matching;
a metric learning component configured to optimize the distance between the two golf swing exemplars; and
an active learning component configured to receive human annotations marking attributes tagged to the stored golf swing exemplars and in communication with the database search engine and further configured to spot inconsistencies in the human annotation tags marking attributes, to identify typical patterns in stored golf swing exemplars with data clustering and to identify stored golf swing exemplars at data cluster boundaries to suggest further annotation tagging.

14. The virtual golf coaching system of claim 11, further comprising the database search engine configured to use lower bound estimation to estimate the lower bound distance for all exemplars with respect to the received golf swing exemplar and to safely skip searching the database for golf swing exemplars with lower bounds larger than the current estimated the lower bound distance met in the searching process.

15. The virtual golf coaching system of claim 14, further comprising the database search engine configured to use branch bound and bound based sub-linear searching.

16. The virtual golf coaching system of claim 11, further comprising an active learning component configured to receive human annotations marking attributes in parametric training case data and in communication with the parametric classification recognition process and the one or more support vector machines respectively, to receive parametric training case data, to add human annotations, to save the annotated training case data, and to spot inconsistencies in the human annotations.

17. The virtual golf coaching system of claim 11, further comprising a metric learning component configured to find and to assign different weight factors for different attributes present in the support vector machines.

18. The virtual golf coaching system of claim 11, further comprising a metric learning component configured to find and to assign different weight factors for different attributes present in the support vector machines.

19. A method for virtual golf coaching comprising:
attaching a first electronic device to a golf club that transmits motion data from a swinging golf club describing the golf club movement;
swinging the golf club;
providing a second electronic device comprising:
  providing a display;
  providing a database of stored golf swing exemplars searchable to and configured to output golf swing attributes from a query comprising the motion data; and
  providing a motion attribute recognition system comprising:
    pre-processing a received a data stream including the motion data and outputting golf swing exemplars comprising:
      transforming raw motion data into a quaternion suitable to measure the distance between two rotations by comparing the quaternion of a one rotation with the quaternion of the other rotation using an orientation matrix conversion process;
      aligning the starting plane of the motion data using a spatial alignment process; and
      locating the actual segment of the motion data within the data stream using a temporal segmentation process;
    providing a non-parametric classification recognition component in communication with the pre-processing component comprising:
      storing golf swing exemplars in the database;
      searching the database of stored golf swing exemplars for comparison with a received golf swing exemplar from the pre-processing component using a database search engine; and
      receiving golf swing exemplars from the pre-processing component and the database search engine and outputting attributes of the golf swing exemplar received from the pre-processing component using a non-parametric classification recognition process; and
    providing a parametric classification recognition component in communication with the pre-processing component comprising:
      finding one of the presence and absence of an attribute in a golf swing exemplar received from the pre-processing component using one or more support vector machines; and
      receiving a golf swing exemplar from the pre-processing component and querying the one or more support vector machines for the presence of an attribute in the golf swing exemplar and outputting one of the presence and absence of an attribute in the golf swing exemplar using a parametric classification recognition process; and
configuring an application in communication with the first electronic device, the database and the display to receive the motion data transmitted from the first electronic device, to query the database with the motion data, to receive attributes from the database in response to the query, and to output attribute information on the display.

* * * * *